(12) United States Patent
Tasker et al.

(10) Patent No.: US 8,101,612 B2
(45) Date of Patent: *Jan. 24, 2012

(54) PHTHALAZINE COMPOUNDS AND METHODS OF USE

(75) Inventors: Andrew Tasker, Simi Valley, CA (US); Dawei Zhang, Thousand Oaks, CA (US); Liping H. Pettus, Thousand Oaks, CA (US); Rob M. Rzasa, Ventura, CA (US); Kelvin K. C. Sham, Thousand Oaks, CA (US); Shimin Xu, Newbury Park, CA (US); Partha Chakrabarti, Nagpur (IN)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/899,363

(22) Filed: Sep. 4, 2007

(65) Prior Publication Data

US 2008/0119468 A1 May 22, 2008

Related U.S. Application Data

(60) Provisional application No. 60/842,466, filed on Sep. 5, 2006.

(51) Int. Cl.
| | |
|---|---|
| C07D 237/30 | (2006.01) |
| C07D 413/04 | (2006.01) |
| A61K 31/502 | (2006.01) |
| A61K 31/5355 | (2006.01) |
| A61P 29/00 | (2006.01) |
| A61P 19/02 | (2006.01) |
| A61P 19/10 | (2006.01) |
| A61P 17/06 | (2006.01) |
| A61P 17/00 | (2006.01) |
| A61P 31/00 | (2006.01) |
| A61P 31/16 | (2006.01) |
| A61P 31/22 | (2006.01) |
| A61P 37/08 | (2006.01) |
| A61P 21/00 | (2006.01) |
| A61P 3/10 | (2006.01) |
| A61P 9/10 | (2006.01) |
| A61P 33/06 | (2006.01) |

(52) U.S. Cl. ...... 514/248; 544/237; 544/116; 514/234.5
(58) Field of Classification Search ............... 514/234.5, 514/241, 240, 248; 544/237, 212, 219, 180, 544/116
See application file for complete search history.

(56) References Cited

U.S. PATENT DOCUMENTS

| 6,635,644 B2 | 10/2003 | Salituro |
| 6,794,380 B2 | 9/2004 | Brown |
| 2006/0035897 A1 | 2/2006 | Caravatti |
| 2006/0199817 A1 | 9/2006 | Tasker |

FOREIGN PATENT DOCUMENTS

| WO | 9716442 A1 | 5/1997 |
| WO | 2004010995 A1 | 2/2004 |
| WO | 2005009937 A1 | 2/2005 |
| WO | WO 2006094187 | * 3/2005 |
| WO | 2006094187 A1 | 9/2006 |

OTHER PUBLICATIONS

Schreiber, et al., Clin. Gastroenterol. Hepatol., Mar. 2006, 4(3): 325-334 (PubMed abstract).*
Newton, et al., Drug Discovery Today: Disease Mechanisms, 2006, pp. 53-61.*
Feldmann, Nature Immunol., vol. 2, #9, Sep. 2001, pp. 771-773.*
Hashimoto, et al., J. PHarma col. & Experim. Therap., vol. 293 #2, pp. 370-375, 2000.*
Hensley, et al., J. Neurochem. vol. 5, 1999, pp. 2053-2058.*
Johnson, et al., Science, vol. 298, Dec. 6, 2002, 1911-1912.*
Hideshima, et al., Oncogene (2004) 23, 8766-8776.*
Shohami et al., J. Cereb. Blood Flow Metab. 14:615 (1994).
Feurstein et al., Neurosci. Lett. 164:125 (1993).
Feurstein, Stroke 25:1481 (1994).
Clouse et al., J. Immunol. 142:431 (1989).
Lahdevirta et al., (Am. J. Med. 85:289 (1988).
Abraham, Lancet, 351:929 (1998).

(Continued)

*Primary Examiner* — James O Wilson
*Assistant Examiner* — Cecilia M Jaisle
(74) *Attorney, Agent, or Firm* — G. Prabhakar Reddy

(57) ABSTRACT

The present invention comprises a new class of compounds useful for the prophylaxis and treatment of p38 kinase mediated diseases and related inflammatory conditions. The compounds have a general Formula II

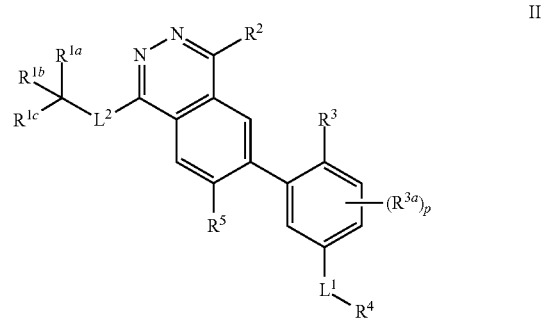

wherein $L^1$, $L^2$, $R^{1a}$, $R^{1b}$, $R^{1c}$, $R^2$, $R^3$, $R^{3a}$, $R^4$, $R^5$ and p are defined herein. The invention also comprises pharmaceutical compositions including one or more compounds of Formula I, uses of such compounds and compositions for treatment of p38 kinase mediated diseases including rheumatoid arthritis, psoriasis and other inflammation disorders, as well as intermediates and processes useful for the preparation of compounds of Formula I.

10 Claims, No Drawings

OTHER PUBLICATIONS

Couriel, Curr. Opinion Oncology, 12:582 (2000).
Labiache, Rheumatology, 43:531 (2004).
Ruan, Cytokine GF Review, 14:447 (2003).
Roberts, Chest, 124:2028 (2003).
WGET, New England J. Med., 352:351 (2005).
Sugano et al, Mol. Cell Bioch., 266:127 (2004).
Chandrasekhar et al., Clinical Immunol Immunopathol., 55:382 (1990).
Firestein, Am. J. Pathol., 140:1309 (1992).
Dinarello, Eur. Cytokine Netw., 5:517-531 (1994).
Folks et al., J. Immunol., 136:40 (1986).
Beutler et al. (J. Immunol., 135:3969 (1985).
Baracos et al. (New Eng. J. Med., 308:553 (1983).
Brahn et al., Lymphokine Cytokine Res. 11:253 (1992).
Cooper, Clin. Exp. Immunol., 898:244 (1992).
Feldmann et al., Immunological Reviews, pp. 195-223 (1995).
Berge et al., J. Pharm. Sci., 66, 1 (1977).
J. Org. Chem. 2005, 70, pp. 5721-5724.
C. A. Winter et al., Proc. Soc. Exp. Biol. Med., 111:544 (1962).
D. E. Trentham et al., J. Exp. Med., 146:857 (1977).
J. S. Courtenay, Nature (New Biol.), 283:666 (1980).

* cited by examiner

PHTHALAZINE COMPOUNDS AND METHODS OF USE

This application claims the benefit of U.S. Provisional Application No. 60/842,466, filed Sep. 5, 2006, now expired, which is hereby incorporated herein by reference in its entirety.

FIELD OF THE INVENTION

The invention relates generally to the field of pharmaceutical agents and, more specifically, to pharmaceutically active compounds, pharmaceutical compositions and methods of use thereof, to treat various disorders, including TNF-α, IL-1β, IL-6 and/or IL-8 mediated diseases and other maladies, such as inflammation and pain. The invention also relates to intermediates and processes useful in the preparation of such compounds.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating inflammatory cytokine production via various pathways. Uncontrolled or excessive cytokine production has been observed in many disease states, and particularly in those related to inflammation. The p38 protein kinase has been reported to be involved in the regulation of pro-inflammatory cytokines, including, interleukin-1 (IL-1) and Tumor Necrosis Factor α (TNF-α), which are secreted by a variety of cells, such as monocytes and macrophages, in response to many inflammatory stimuli (e.g., lipopolysaccharide—LPS) or external cellular stress (e.g., osmotic shock and peroxide).

Elevated levels of TNF-α over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

TNF-α has been reported to play a role in head trauma, stroke, and ischemia. For instance, in animal models of head trauma (rat), TNF-α levels increased in the contused hemisphere (Shohami et al., J. Cereb. Blood Flow Metab. 14:615 (1994)). In a rat model of ischemia wherein the middle cerebral artery was occluded, the levels of TNF-α mRNA of TNF-α increased (Feurstein et al., Neurosci. Lett. 164:125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, Stroke 25:1481 (1994)).

TNF-α appears to play a role in promoting certain viral life cycles and disease states associated therewith. For instance, TNF-α secreted by monocytes induced elevated levels of HIV expression in a chronically infected T cell clone (Clouse et al., J. Immunol. 142:431 (1989)). Lahdevirta et al., (Am. J. Med. 85:289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8. Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

Antagonism of TNF-α has been reported to be beneficial for treating uveitis (Reiff et al, A&R 44:141-145 (2001)); Sepsis (Abraham, Lancet, 351:929 (1998)); Systemic Lupus Erythrematosis (SLE) (Aringer, A&R, 50:3161 (2004)); Graft vs Host Disease (Couriel, Curr. Opinion Oncology, 12:582 (2000)); Polymyositis and Dermatomyositis (Labiache, Rheumatology, 43:531 (2004)); Type II diabetes (Ruan, Cytokine GF Review, 14:447 (2003)); Sjogren's disease (Marriette, A&R, 50:1270 (2004)), Sarcoidosis (Roberts, Chest, 124:2028 (2003)); Wegener's granulomatosis (WGET, New England J. Med., 352:351 (2005)) and post MI cardiac dysfunction (Sugano et al, Mol. Cell. Bioch., 266:127 (2004)). In addition, TNF-α has been reported to play a role in SAPHO, periodic fever, relapsing polychondritis, multicentric reticulohistiocytosis, macrophage activation syndrome, Hyper IgD syndrome, familial Hibernian fever, Pyoderma gangrenosum, Cochleovestibular disorders, Cicatrical pemphigoid, Herniated intervertebral disc diseases, amyloidosis, CINCA syndrome, myelodysplastic syndrome, alcoholic hepatitis, and endometriosis. Finally, indications which have already been approved for an agent which modulates TNF-α levels in the plasma, and/or other pro-inflammatory cytokines, include without limitation, inflammatory bowel disease (IBD), psoriatis arthritis, ankylosing spondylitis and juvenile RA.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., Clinical Immunol Immunopathol., 55:382 (1990)). In studies using cultured rheumatoid synovial cells, IL-1 is a more potent inducer of stromelysin than is TNF-α (Firestein, Am. J. Pathol., 140: 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokine Netw., 5:517-531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., J. Immunol., 136:40 (1986)). Beutler et al. (J. Immunol., 135:3969 (1985)) discussed the role of IL-1 in cachexia. Baracos et al. (New Eng. J. Med., 308:553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., Lymphokine Cytokine Res. 11:253 (1992); and Cooper, Clin. Exp. Immunol., 898:244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195-223 (1995)). These approaches block the effects of TNF-α and IL-1 by either protein sequestration or receptor antagonism.

Yet another approach to block the effect of TNF-α has been to modulate the activity of the p38 kinase enzyme. For example, the PCT publication, WO 04/010995, published on Feb. 5, 2004, describes fused heteroaryl derivatives for use as P38 kinase inhibitors in the treatment of I.A. rheumatoid arthritis; PCT publication, WO 2005/009937, published on Feb. 3, 2005, describes 5-membered heterocycle-based P38 kinase inhibitors; U.S. Pat. No. 6,635,644, issued Oct. 21, 2003, describes fused nitrogen-containing bicyclic ring systems as P38 inhibitors; and U.S. Pat. No. 6,794,380, issued Sep. 21, 2004, describes amide derivatives as P38 inhibitors.

BRIEF DESCRIPTION OF THE INVENTION

The present invention provides a new class of compounds useful in regulating the activity of p38, and accordingly, useful in the prophylaxis and treatment of related diseases, such as TNF-α, IL-1β, IL-6 and/or IL-8 mediated diseases and other maladies. The invention further provides pharmaceutical compositions comprising the compounds of the invention, methods for the prophylaxis and treatment of TNF-α, IL-1β, IL-6 and/or IL-8 mediated diseases, including inflammation, pain and diabetes, as well as intermediates and processes or methods useful for the preparation of the compounds of the invention.

The compounds of the present invention, including stereoisomers, tautomers, solvates, pharmaceutically acceptable salts, derivatives or prodrugs thereof, are defined generally by Formula I

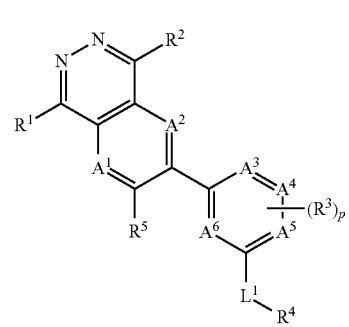

wherein $A^1$, $A^2$, $A^3$, $A^4$, $A^5$, $A^6$, $L^1$, $R^1$, $R^2$, $R^3$, $R^4$ and $R^5$ are as described herein below. These compounds are capable of modulating the activity of the p38 kinase enzyme. To this end, the invention also provides use of these compounds to attenuate, alleviate, or treat disorders, therapeutically, prophylactically, acutely and/or chronically mediated by the activity of p38, such as those described herein. For example, and in one embodiment, the invention provides a pharmaceutical composition comprising an effective dosage amount of a compound of Formula I in association with a least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts or prodrugs thereof, are defined by general Formula I:

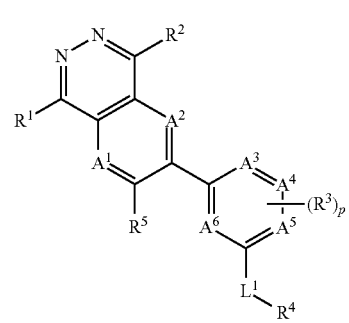

wherein
each of $A^1, A^2, A^3, A^4, A^5$ and $A^6$, independently, is $CR^3$ or N, provided that no more than two of $A^3, A^4, A^5$ and $A^6$ is N;

$L^1$ is —C(O)NR$^6$—, —NR$^6$C(O)—, —NR$^6$C(O)NR$^6$—, —S(O)$_2$NR$^6$—, —NR$^6$S(O)$_2$NR$^6$— or —NR$^6$S(O)$_2$—, wherein $R^6$ is H or $C_{1-4}$-alkyl;

$R^1$ is —CR$^7$R$^7$)$_n$X wherein X is $C_{1-10}$-alkyl, $C_{3-6}$-cycloalkyl, OC$_{1-10}$-alkyl, NHC$_{1-10}$-alkyl, N(C$_{1-10}$-alkyl)$_2$ or SC$_{1-10}$-alkyl and n is 0, 1 or 2, the $C_{1-10}$-alkyl moiety in each and cycloalkyl optionally substituted with 1-5 substituents of halo, haloalkyl, CN, OH, NO$_2$, NH$_2$, NR$^7$R$^7$, NR$^7$R$^8$, OR$^7$, SR$^7$, OR$^8$, SR$^8$, C(O)R$^7$, C(O)R$^8$, C(O)NR$^7$R$^7$, NR$^7$C(O)R$^7$, NR$^7$C(O)NR$^7$R$^7$, C(O)NR$^7$R$^8$, NR$^7$C(O)R$^8$, NR$^7$C(O)NR$^7$R$^8$, S(O)$_2$R$^7$, S(O)$_2$NR$^7$R$^7$, NR$^7$S(O)$_2$NR$^7$R$^7$, NR$^7$S(O)$_2$R$^7$, S(O)$_2$R$^8$, S(O)$_2$NR$^7$R$^8$, NR$^7$S(O)$_2$NR$^7$R$^8$, NR$^7$S(O)$_2$R$^8$ or a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^7$, $R^8$ or $R^9$;

$R^2$ is H, halo, haloalkyl, NO$_2$, CN, $C_{1-10}$-alkyl, OC$_{1-10}$-alkyl, SC$_{1-10}$-alkyl, NHC$_{1-10}$-alkyl, C(O)C$_{1-10}$-alkyl;

each $R^3$, independently, is H, halo, haloalkyl, NO$_2$, CN, $C_{1-10}$-alkyl, OC$_{1-10}$-alkyl, SC$_{1-10}$-alkyl, NHC$_{1-10}$-alkyl, C(O)C$_{1-10}$-alkyl;

$R^4$ is a partially or fully saturated or unsaturated 3-8 membered monocyclic or 6-12 membered bicyclic ring system, said ring system formed of carbon atoms optionally including 1-4 heteroatoms if monocyclic or 1-6 heteroatoms if bicyclic, said heteroatoms selected from O, N, or S, wherein said ring system is optionally substituted independently with one or more additional substituents of $R^7$, $R^8$, $R^9$, NR$^7$R$^7$, NR$^7$R$^8$, OR$^7$, SR$^7$, OR$^8$, SR$^8$, C(O)R$^7$, C(O)R$^8$, C(O)NR$^7$R$^7$, C(O)NR$^7$R$^8$, OC(O)NR$^7$R$^8$, NR$^7$C(O)R$^7$, NR$^7$C(O)R$^8$, NR$^7$C(O)NR$^7$R$^7$, NR$^7$C(O)NR$^7$R$^8$, NR$^7$(COOR$^7$), NR$^7$(COOR$^8$), S(O)$_2$R$^7$, S(O)$_2$R$^8$, S(O)$_2$NR$^7$R$^8$, S(O)$_2$NR$^7$R$^8$, NR$^7$S(O)$_2$NR$^7$R$^8$, NR$^7$S(O)$_2$R$^7$ or NR$^7$S(O)$_2$R$^8$;

$R^5$ is H, halo, haloalkyl, NO$_2$, CN, $C_{1-10}$alkyl, OC$_{1-10}$-alkyl, SC$_{1-10}$-alkyl, NHC$_{1-10}$-alkyl, C(O)C$_{1-10}$-alkyl;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of NR$^8$R$^9$, NR$^9$R$^9$, OR$^8$, SR$^8$, OR$^9$, SR$^9$, C(O)R$^8$, OC(O)R$^8$, COOR$^8$, C(O)R$^9$, OC(O)R$^9$, COOR$^9$, C(O)NR$^8$R$^9$, C(O)NR$^9$R$^9$, NR$^9$C(O)R$^8$, NR$^9$C(O)R$^9$, NR$^9$C(O)NR$^8$R$^9$, NR$^9$C(O)NR$^9$R$^9$, NR$^9$(COOR$^8$), NR$^9$(COOR$^9$), OC(O)NR$^8$R$^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$, $R^8$ or $R^9$;

$R^8$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, NR$^9$R$^9$, OR$^9$, SR$^9$, C(O)R$^9$, COOR$^9$, C(O)NR$^9$R$^9$, NR$^9$C(O)R$^9$, NR$^9$C(O)NR$^9$R$^9$, OC(O)NR$^9$R$^9$, S(O)$_2$R$^9$, S(O)$_2$NR$^9$R$^9$, NR$^9$S(O)$_2$R$^9$, or a partially or fully saturated or unsaturated 5-6 membered ring of carbon atoms optionally including 1-3 heteroatoms selected from O, N, or S, and optionally substituted independently with 1-5 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of $R^9$;

$R^9$ is H, halo, haloalkyl, CN, OH, NO$_2$, NH$_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl; and p is 0, 1, 2 or 3.

In another embodiment, Formula I includes compounds, or a stereoisomer or pharmaceutically acceptable salts thereof wherein each of $A^1$ is $CR^3$, in conjunction with any of the above or below embodiments.

In another embodiment, Formula I includes compounds, or a stereoisomer or pharmaceutically acceptable salts thereof wherein each of $A^1$ is CH, in conjunction with any of the above or below embodiments.

In another embodiment, Formula I includes compounds, or a stereoisomer or pharmaceutically acceptable salts thereof wherein each of $A^1$ is N, in conjunction with any of the above or below embodiments.

In another embodiment, Formula I includes compounds, or a stereoisomer or pharmaceutically acceptable salts thereof wherein each of $A^2$ is $CR^3$, in conjunction with any of the above or below embodiments.

In another embodiment, Formula I includes compounds, or a stereoisomer or pharmaceutically acceptable salts thereof wherein each of $A^2$ is CH, in conjunction with any of the above or below embodiments.

In another embodiment, Formula I includes compounds, or a stereoisomer or pharmaceutically acceptable salts thereof wherein each of $A^2$ is N, in conjunction with any of the above or below embodiments.

In another embodiment, Formula I includes compounds, or a stereoisomer or pharmaceutically acceptable salts thereof wherein each of $A^3$ is $CR^3$, in conjunction with any of the above or below embodiments.

In another embodiment, Formula I includes compounds, or a stereoisomer or pharmaceutically acceptable salts thereof wherein each of $A^3$ is CH, in conjunction with any of the above or below embodiments.

In another embodiment, Formula I includes compounds, or a stereoisomer or pharmaceutically acceptable salts thereof wherein each of $A^3$ is N, in conjunction with any of the above or below embodiments.

In another embodiment, Formula I includes compounds, or a stereoisomer or pharmaceutically acceptable salts thereof wherein each of $A^4$ is $CR^3$, in conjunction with any of the above or below embodiments.

In another embodiment, Formula I includes compounds, or a stereoisomer or pharmaceutically acceptable salts thereof wherein each of $A^4$ is CH, in conjunction with any of the above or below embodiments.

In another embodiment, Formula I includes compounds, or a stereoisomer or pharmaceutically acceptable salts thereof wherein each of $A^4$ is N, in conjunction with any of the above or below embodiments.

In another embodiment, Formula I includes compounds, or a stereoisomer or pharmaceutically acceptable salts thereof wherein each of $A^5$ is $CR^3$, in conjunction with any of the above or below embodiments.

In another embodiment, Formula I includes compounds, or a stereoisomer or pharmaceutically acceptable salts thereof wherein each of $A^5$ is CH, in conjunction with any of the above or below embodiments.

In another embodiment, Formula I includes compounds, or a stereoisomer or pharmaceutically acceptable salts thereof wherein each of $A^5$ is N, in conjunction with any of the above or below embodiments.

In another embodiment, Formula I includes compounds, or a stereoisomer or pharmaceutically acceptable salts thereof wherein each of $A^6$ is $CR^3$, in conjunction with any of the above or below embodiments.

In another embodiment, Formula I includes compounds, or a stereoisomer or pharmaceutically acceptable salts thereof wherein each of $A^6$ is CH, in conjunction with any of the above or below embodiments.

In another embodiment, Formula I includes compounds, or a stereoisomer or pharmaceutically acceptable salts thereof wherein each of $A^6$ is N, in conjunction with any of the above or below embodiments.

In another embodiment, Formula I includes compounds, or a stereoisomer or pharmaceutically acceptable salts thereof wherein each of $A^1$ and $A^2$ is $CR^3$, and one of $A^3$, $A^4$, $A^5$ and $A^6$, independently, is N and the other three of $A^3$, $A^4$, $A^5$ and $A^6$ is $CR^3$, in conjunction with any of the above or below embodiments.

In another embodiment, Formula I includes compounds, or a stereoisomer or pharmaceutically acceptable salts thereof wherein each of $A^1$ and $A^2$ is $CR^3$, and two of $A^3$, $A^4$, $A^5$ and $A^6$, independently, is N and the other two of $A^3$, $A^4$, $A^5$ and $A^6$ is $CR^3$, in conjunction with any of the above or below embodiments.

In another embodiment, Formula I includes compounds, or a stereoisomer or pharmaceutically acceptable salts thereof wherein each of $A^1$ and $A^2$ is N, and each of $A^3$, $A^4$, $A^5$ and $A^6$, independently, is $CR^3$, in conjunction with any of the above or below embodiments.

In another embodiment, Formula I includes compounds, or a stereoisomer or pharmaceutically acceptable salts thereof wherein each one of $A^1$ and $A^2$ is N and the other of $A^1$ and $A^2$ is $CR^3$, and each of $A^3$, $A^4$, $A^5$ and $A^6$, independently, is $CR^3$, in conjunction with any of the above or below embodiments.

In another embodiment, Formula I includes compounds, or a stereoisomer or pharmaceutically acceptable salts thereof wherein each of $A^1$, $A^2$, $A^3$, $A^4$, $A^5$ and $A^6$, independently, is $CR^3$, in conjunction with any of the above or below embodiments.

In another embodiment, Formula I includes compounds, or a stereoisomer or pharmaceutically acceptable salts thereof wherein each of $A^1$, $A^2$, $A^5$ and $A^6$, independently, is CH and each of $A^3$ and $A^4$, independently, is $CR^3$, in conjunction with any of the above or below embodiments.

In another embodiment, Formula I includes compounds, or a stereoisomer or pharmaceutically acceptable salts thereof wherein $R^1$ is —$CR^7R^7)_nX$ wherein X is optionally substituted $C_{1-10}$-alkyl or $C_{3-6}$cycloalkyl and n is 0, 1 or 2, in conjunction with any of the above or below embodiments.

In another embodiment, Formula I includes compounds, or a stereoisomer or pharmaceutically acceptable salts thereof wherein $R^1$ is —$(CR^7R^7)$ X wherein X is optionally substituted $OC_{1-10}$-alkyl and n is 0, 1 or 2, in conjunction with any of the above or below embodiments.

In another embodiment, Formula I includes compounds, or a stereoisomer or pharmaceutically acceptable salts thereof wherein $R^1$ is —$(CR^7R^7)_nX$ wherein X is optionally substituted $SC_{1-10}$-alkyl and n is 0, 1 or 2, in conjunction with any of the above or below embodiments.

In another embodiment, Formula I includes compounds, or a stereoisomer or pharmaceutically acceptable salts thereof wherein $R^1$ is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^7$, $R^8$ or $R^9$, in conjunction with any of the above or below embodiments.

In another embodiment, Formula I includes compounds, or a stereoisomer or pharmaceutically acceptable salts thereof wherein $R^1$ is phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, thiadiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$, in conjunction with any of the above or below embodiments.

In another embodiment, Formula I includes compounds, or a stereoisomer or pharmaceutically acceptable salts thereof wherein each of $A^3$, $A^4$, $A^5$ and $A^6$, independently, is $CR^3$; and $R^4$ is a ring selected from cyclopropyl, cyclobutyl, cyclopentyl, cyclohexyl, phenyl, pyridine, pyrimidine, triazine, thiophene, furan, pyrrole, pyrazole, imidazole, triazole, thiazole, isothiazole, thiadiazole, oxazole, isoxazole, pyrrolidine, tetrahydrofuran, tetrahydropyrrole, piperidine, piperizine, morpholine or pyran, each ring of which is optionally substituted independently with 1-5 substituent of $R^9$, in conjunction with any of the above or below embodiments.

In another embodiment, Formula I includes compounds, or a stereoisomer or pharmaceutically acceptable salts thereof wherein $A^1$ is $CR^3$;

$A^2$ is $CR^3$;

$L^1$ is —$C(O)NR^6$—, —$NR^6C(O)$—, —$S(O)_2NR^6$— or —$NR^6S(O)_2$—, wherein $R^6$ is H or $C_{1-4}$-alkyl;

$R^1$ is —$C_{1-10}$-alkyl, $C_{3-6}$cycloalkyl or $OC_{1-10}$-alkyl, the $C_{1-10}$-alkyl moiety in each and cycloalkyl optionally substituted with 1-5 substituents of halo, haloalkyl, CN, OH, $NO_2$, $NH_2$, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine;

$R^2$ is H or $C_{1-10}$-alkyl; and $R^4$ is a ring selected from cyclopropyl, cyclobutyl, cyclopentyl, cyclohexyl, phenyl, pyridine, pyrimidine, triazine, thiophene, furan, pyrrole, pyrazole, imidazole, triazole, thiazole, isothiazole, thiadiazole, oxazole, isoxazole, pyrrolidine, tetrahydrofuran, tetrahydropyrrole, piperidine, piperizine, morpholine or pyran, each ring of which is optionally substituted independently with 1-5 substituent of $R^9$;

$R^5$ is H or $C_{1-10}$-alkyl;

$R^7$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, thiadiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-3 substituents of $R^9$; and $R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl, in conjunction with any of the above or below embodiments.

In another embodiment, Formula I includes compounds, or a stereoisomer or pharmaceutically acceptable salts thereof wherein each of $A^3$, $A^4$, $A^5$ and $A^6$, independently, is $CR^3$, and $R^4$ is a cyclopropyl, cyclopentyl, imidazole, pyrazole, triazole, oxazole, isoxazole, thiazole, isothiazole or thiadiazole, each of which is optionally substituted independently with 1-5 substituents of $R^9$, in conjunction with any of the above or below embodiments.

In one embodiment of the invention, the compounds, including stereoisomers, tautomers, solvates, pharmaceutically acceptable salts or prodrugs thereof, are defined by general Formula II

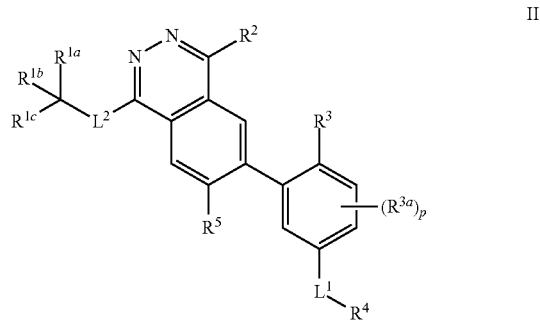

II wherein $L^1$ is $—C(O)NR^6—$, $—NR^6C(O)—$, $—S(O)_2NR^6—$ or $—NR^6S(O)_2—$, wherein $R^6$ is H or $C_{1-4}$-alkyl;

$L^2$ is $—O(CH_2)_n—$ or $—CH_2)_nO—$ wherein n is 0, 1 or 2;

each of $R^{1a}$, $R^{1b}$ and $R^{1c}$, independently, is H, halo, haloalkyl, CN, OH, $NO_2$, $NH_2$, $C_{1-10}$-alkyl, optionally comprising 1-3 heteroatoms of N, O or S, $NR^7R^7$, $NR^7R^8$, $OR^7$, $SR^7$, $OR^8$, $SR^8$, $C(O)R^7$, $C(O)R^8$, $C(O)NR^7R^7$, $NR^7C(O)R^7$, $NR^7C(O)NR^7R^7$, $C(O)NR^7R^8$, $NR^7C(O)R^8$, $NR^7C(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$, $NR^7S(O)_2R^8$ or a 3-6 membered monocyclic ring formed of carbon atoms optionally including 1-3 heteroatoms selected from O, N, or S, and optionally substituted independently with 1-5 substituents of $R^9$, alternatively, any two of $R^{1a}$, $R^{1b}$ and $R^{1c}$ taken together with the carbon atom to which it is attached form a $C_{3-6}$cycloalkyl ring, optionally substituted with 1-3 substituents of $R^9$;

$R^2$ is H;

$R^3$ is H, halo, haloalkyl, CN, OH, $NO_2$, $NH_2$, $C_{1-4}$-alkyl, $OC_{1-4}$-alkyl or $OC_{1-4}$-haloalkyl;

each $R^{3a}$, independently, is H, halo, $CF_3$, $OCF_3$, CN, OH, $NO_2$, $NH_2$, methyl, ethyl, methoxyl or ethoxyl; and $R^4$ is a cyclopropyl, cyclopubtyl, cyclopentyl, cyclohexyl, phenyl, pyridine, pyrimidine, triazine, thiophene, furan, pyrrole, pyrazole, imidazole, triazole, thiazole, isothiazole, thiadiazole, oxazole, isoxazole, pyrrolidine, tetrahydrofuran, tetrahydropyrrole, piperidine, piperizine, morpholine or pyran, each of which is optionally substituted independently with 1-5 substituents of halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

$R^5$ is H; and p is 0, 1 or 2.

In another embodiment, Formula II includes compounds, or a stereoisomer or pharmaceutically acceptable salts thereof wherein $L^2$ is —O($CH_2$)$_n$— wherein n is 0, 1 or 2, in conjunction with any of the above or below embodiments.

In another embodiment, Formula II includes compounds, or a stereoisomer or pharmaceutically acceptable salts thereof wherein $L^2$ is —$CH_2$)$_n$O— wherein n is 0, 1 or 2, in conjunction with any of the above or below embodiments.

In another embodiment, Formula II includes compounds, or a stereoisomer or pharmaceutically acceptable salts thereof wherein each of $R^{1a}$, $R^{1b}$ and $R^{1c}$, independently, is H, halo, haloalkyl, CN, OH, $NO_2$, $NH_2$, $C_{1-10}$-alkyl, optionally comprising 1-3 heteroatoms of N, O or S, or a 3-6 membered monocyclic ring formed of carbon atoms optionally including 1-3 heteroatoms selected from O, N, or S, and optionally substituted independently with 1-5 substituents of $R^9$, in conjunction with any of the above or below embodiments.

In another embodiment, Formula II includes compounds, or a stereoisomer or pharmaceutically acceptable salts thereof wherein one or two of $R^{1a}$, $R^{1b}$ and $R^{1c}$, independently, is H, halo, haloalkyl, CN, OH, $NO_2$, $NH_2$, $C_{1-10}$-alkyl, optionally comprising 1-3 heteroatoms of N, O or S, or a 3-6 membered monocyclic ring formed of carbon atoms optionally including 1-3 heteroatoms selected from O, N, or S, and optionally substituted independently with 1-5 substituents of $R^9$ and the other of $R^{1a}$, $R^{1b}$ and $R^{1c}$, independently, is H, halo or haloalkyl, in conjunction with any of the above or below embodiments.

In another embodiment, Formula II includes compounds, or a stereoisomer or pharmaceutically acceptable salts thereof wherein one of $R^{1a}$, $R^{1b}$ and $R^{1c}$, independently, is H, halo, haloalkyl, CN, OH, $NO_2$, $NH_2$, $C_{1-10}$-alkyl, optionally comprising 1-3 heteroatoms of N, O or S, or a 3-6 membered monocyclic ring formed of carbon atoms optionally including 1-3 heteroatoms selected from O, N, or S, and optionally substituted independently with 1-5 substituents of $R^9$ and the other two of $R^{1a}$, $R^{1b}$ and $R^{1c}$, independently, is H, halo or haloalkyl in conjunction with any of the above or below embodiments.

In another embodiment, Formula II includes compounds, or a stereoisomer or pharmaceutically acceptable salts thereof wherein any two of $R^{1a}$, $R^{1b}$ and $R^{1c}$ taken together with the carbon to which it is attached form a $C_{3-6}$cycloalkyl ring, optionally substituted with 1-3 substituents of $R^9$, in conjunction with any of the above or below embodiments.

In another embodiment, Formula II includes compounds, or a stereoisomer or pharmaceutically acceptable salts thereof wherein $R^{1a}$ and $R^{1b}$ taken together with the carbon to which it is attached form a cyclopropyl ring, optionally substituted with 1-3 substituents of $R^9$, in conjunction with any of the above or below embodiments.

In another embodiment, Formula II includes compounds, or a stereoisomer or pharmaceutically acceptable salts thereof wherein $L^1$ is —C(O)$NR^6$— or —S(O)$_2NR^6$—, wherein $R^6$ is H or $C_{1-4}$-alkyl, and $L^2$ is —O—, in conjunction with any of the above or below embodiments.

In another embodiment, Formula II includes compounds, or a stereoisomer or pharmaceutically acceptable salts thereof wherein each $R^{3a}$, independently, is H, halo, $CF_3$, $OCF_3$, CN, OH, $NO_2$, $NH_2$, methyl, ethyl, methoxyl or ethoxyl and p is 0 or 1, in conjunction with any of the above or below embodiments.

In another embodiment, Formula II includes compounds, or a stereoisomer or pharmaceutically acceptable salts thereof wherein $L^1$ is —C(O)$NR^6$— or —S(O)$_2NR^6$—, wherein $R^6$ is H or $C_{1-4}$-alkyl;

$L^2$ is —O—;

each of $R^{1a}$, $R^{1b}$ and $R^{1c}$, independently, is H, halo, haloalkyl, CN, OH, $NO_2$, $NH_2$, $C_{1-10}$-alkyl, optionally comprising 1-3 heteroatoms of N, O or S, or a 3-6 membered monocyclic ring formed of carbon atoms optionally including 1-3 heteroatoms selected from O, N, or S, and optionally substituted independently with 1-5 substituents of $R^9$, alternatively $R^{1a}$ and $R^{1b}$ taken together with the carbon atom to which it is attached form a cyclopropyl ring, optionally substituted with 1-3 substituents of $R^9$, in conjunction with any of the above or below embodiments.

$R^2$ is H;

$R^3$ is H, halo, $CF_3$, $OCF_3$, CN, OH, $NO_2$, $NH_2$, methyl, ethyl, methoxyl or ethoxyl;

each $R^{3a}$, independently, is H, halo, $CF_3$, $OCF_3$, CN, OH, $NO_2$, $NH_2$, methyl, ethyl, methoxyl or ethoxyl; and $R^4$ is a cyclopropyl, cyclopentyl, imidazole, pyrazole, triazole, oxazole, isoxazole, thiazole, isothiazole or thiadiazole, each of which is optionally substituted independently with 1-5 substituents of halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

$R^5$ is H;

p is 0 or 1; and $R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl.

In another embodiment, Formula I or II includes compounds, or a stereoisomer or pharmaceutically acceptable salts thereof wherein $L^1$ is —C(O)$NR^6$—, —$NR^6$C(O)—, —$NR^6$C(O)$NR^6$—, —S(O)$_2NR^6$—, —$NR^6$S(O)$_2NR^6$— or —$NR^6$S(O)$_2$—, wherein $R^6$ is H or $C_{1-4}$-alkyl, in conjunction with any of the above or below embodiments.

In another embodiment, Formula I or II includes compounds, or a stereoisomer or pharmaceutically acceptable salts thereof wherein $L^1$ is —C(O)NR$^6$—, —NR$^6$C(O)—, —S(O)$_2$NR$^6$—, or —NR$^6$S(O)$_2$—, wherein R$^6$ is H or C$_{1-4}$-alkyl, in conjunction with any of the above or below embodiments.

In another embodiment, Formula I or II includes compounds, or a stereoisomer or pharmaceutically acceptable salts thereof wherein $L^1$ is —C(O)NR$^6$— or —S(O)$_2$NR$^6$—, wherein R$^6$ is H or C$_{1-4}$-alkyl, in conjunction with any of the above or below embodiments.

In another embodiment, Formula I or II includes compounds, or a stereoisomer or pharmaceutically acceptable salts thereof wherein $L^1$ is —C(O)NR$^6$—, wherein R$^6$ is H or C$_{1-4}$-alkyl, in conjunction with any of the above or below embodiments.

In another embodiment, Formula I or II includes compounds, or a stereoisomer or pharmaceutically acceptable salts thereof wherein R$^4$ is a ring selected from cyclopropyl, cyclobutyl, cyclopentyl, cyclohexyl, phenyl, pyridine, pyrimidine, pyridazine, triazine, thiophene, furan, pyrrole, pyrazole, imidazole, triazole, thiazole, isothiazole, thiadiazole, oxazole, isoxazole, pyrrolidine, tetrahydrofuran, tetrahydropyrrole, piperidine, piperizine, morpholine or pyran, each ring of which is optionally substituted independently with 1-5 substituent of R$^9$, in conjunction with any of the above or below embodiments.

In another embodiment, Formula I or II includes compounds, or a stereoisomer or pharmaceutically acceptable salts thereof wherein R$^4$ is a ring selected from cyclopropyl, cyclobutyl, cyclopentyl, cyclohexyl, phenyl, pyridine, pyrimidine, thiophene, furan, pyrrole, pyrazole, imidazole, triazole, thiazole, isothiazole, thiadiazole, oxazole, isoxazole, each ring of which is optionally substituted independently with 1-5 substituent of R$^9$, in conjunction with any of the above or below embodiments.

In another embodiment, the compounds provided herewith, or stereoisomers, tautomers, solvates, pharmaceutically acceptable salts, derivatives or prodrugs thereof, are generally defined by Formula III

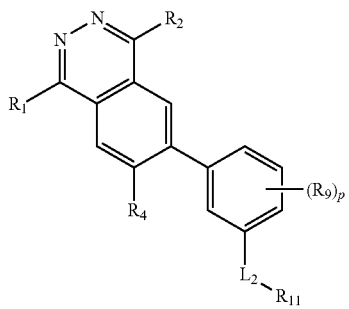

III wherein
R$^1$ is —C$_{1-6}$alkyl, cyclopropyl, —OC$_{1-6}$-alkyl, phenyl, pyridyl, pyrimidyl, tetrahydrofuranyl, tetrahydropyrrolyl or pyrrolidinyl, each of which is optionally substituted independently with 1-5 substituents of halo, haloalkyl, CN, OH, NO$_2$, NH$_2$, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, phenyl or cyclopropyl;
R$^2$ is H;
R$^4$ is H;

R$^9$ is halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine or acetyl;

R$^{11}$ is a cyclopropyl, imidazole, pyrazole or thiadiazole, wherein said pyrazole or thiadiazole is optionally substituted independently with 1-5 substituents of halo, haloalkyl, CN, OH, NO$_2$, NH$_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

$L^2$ is —C(O)NH—, —NHC(O)—, —NHC(O)NH—, —S(O)$_2$NH—, —NHS(O)$_2$NH— or —NHS(O)$_2$—; and
p is 0, 1, 2 or 3.

In yet another embodiment, the compounds provided herewith, or stereoisomers, tautomers, solvates, pharmaceutically acceptable salts, derivatives or prodrugs thereof, are generally defined by Formula IV

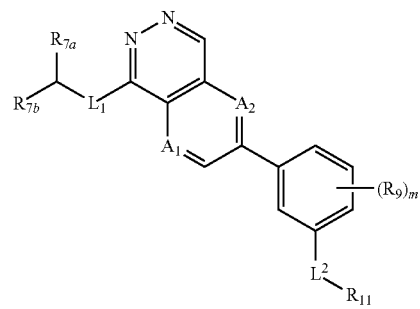

IV wherein
each of A$^1$ and A$^2$, independently, is CH or N;
$L^1$ is —O— or absent;
$L^2$ is —C(O)NH—, —NHC(O)—, —NHC(O)NH—, —S(O)$_2$NH—, —NHS(O)$_2$NH— or —NHS(O)$_2$—;
R$^{7a}$ is H or C$_{1-10}$-alkyl;
R$^{7b}$ is C$_{1-10}$-alkyl or CF$_3$;
R$^9$ is halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine or acetyl;
R$^{11}$ is a phenyl, naphthyl, pyridyl, pyrimidyl, quinolinyl, isoquinolinyl, quinazolinyl, thiophenyl, furyl, pyrrolyl, pyrazolyl, imidazolyl, triazolyl, thiazolyl, thiadiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-5 substituents of halo, haloalkyl, CN, OH, NO$_2$, NH$_2$, OH, oxo, methyl, methoxyl, ethyl, ethoxyl, propyl, propoxyl, isopropyl, cyclopropyl, butyl, isobutyl, tert-butyl, pentyl, hexyl, methylamino, dimethylamino, ethylamino, diethylamino, isopropylamino, acetyl, benzyl, or phenyl; and m is 0, 1, 2 or 3.

In another embodiment, the compounds of Formula I or III include compounds wherein $R^1$ is $OR^7$ and $R^7$ is $C_{1-10}$-alkyl optionally substituted with 1-4 substituents of $R^9$, in conjunction with any of the above or below embodiments.

In another embodiment, the compounds of Formula I or III include compounds wherein $R^1$ is —$C_{1-6}$alkyl, —$OC_{1-6}$-alkyl, phenyl, pyridyl, pyrimidyl, tetrahydrofuranyl, tetrahydropyrrolyl or pyrrolidinyl, each of which is optionally substituted independently with 1-5 substituents of halo, haloalkyl, CN, OH, $NO_2$, $NH_2$, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, phenyl or cyclopropyl, in conjunction with any of the above or below embodiments.

In another embodiment, Formulas I, II or III include compounds wherein $R^2$ is H, halo or $C_{1-10}$alkyl, in conjunction with any of the above or below embodiments.

In another embodiment, the invention provides compounds of Formulas I-III wherein $R^4$ is a pyrazole, thiadiazole or tetrahydropyrrole, said pyrazole, thiadiazole or tetrahydropyrrole being optionally substituted independently with 1-5 substituents of $R^9$, in conjunction with any of the above or below embodiments described herein.

In yet another embodiment, the compounds of Formula I include the examples described hereinbelow.

In yet another embodiment, the compounds of Formulas I or II include a compound, or a pharmaceutically acceptable salt form thereof, selected from: N-3-isoxazolyl-4-methyl-3-(1-((1-methylethyl)oxy)-6-phthalazinyl)benzamide;
N-(1-ethyl-1H-pyrazol-5-yl)-4-methyl-3-(1-((1-methylethyl)oxy)-6-phthalazinyl)benzamide;
4-methyl-3-(1-((1-methylethyl)oxy)-6-phthalazinyl)-N-(1-methyl-1H-pyrazol-5-yl)benzamide;
N-cyclopropyl-3-(1-(ethyloxy)-6-phthalazinyl)-4-methylbenzamide;
4-methyl-N-(1-methyl-1H-pyrazol-5-yl)-3-(1-((2,2,2-trifluoro-1-methylethyl)oxy)-6-phthalazinyl)benzamide;
4-chloro-N-(1-methylethyl)-3-(1-((1-methylethyl)oxy)-6-phthalazinyl)benzamide;
4-methyl-N-(1-methylethyl)-3-(1-((2,2,2-trifluoro-1-methylethyl)oxy)-6-phthalazinyl)benzamide;
4-methyl-N-(1-methylethyl)-3-(1-(2-methylpropyl)-6-phthalazinyl)benzamide;
4-methyl-N-(1-methyl-1H-pyrazol-5-yl)-3-(1-(((1S)-2,2,2-trifluoro-1-methylethyl)oxy)-6-phthalazinyl)benzamide;
4-methyl-N-(1-methyl-1H-pyrazol-5-yl)-3-(1-(((1R)-2,2,2-trifluoro-1-methylethyl)oxy)-6-phthalazinyl)benzamide;
N-cyclopropyl-4-methyl-3-(1-((2,2,2-trifluoro-1-methylethyl)oxy)-6-phthalazinyl)benzamide;
4-methyl-N-(4-methyl-1,3-oxazol-2-yl)-3-(1-((2,2,2-trifluoro-1-methylethyl)oxy)-6-phthalazinyl)benzamide;
4-methyl-N-(1-methylethyl)-3-(1-(((1S)-2,2,2-trifluoro-1-methylethyl)oxy)-6-phthalazinyl)benzamide;
4-methyl-N-(1-methylethyl)-3-(1-(((1R)-2,2,2-trifluoro-1-methylethyl)oxy)-6-phthalazinyl)benzamide;
4-methyl-3-(1-(((1S)-2,2,2-trifluoro-1-methylethyl)oxy)-6-phthalazinyl)benzamide;
4-methyl-3-(1-(((1R)-2,2,2-trifluoro-1-methylethyl)oxy)-6-phthalazinyl)benzamide;
N-(1,1-dimethylethyl)-4-methyl-3-(1-(((1S)-2,2,2-trifluoro-1-methylethyl)oxy)-6-phthalazinyl)benzamide;
4-methyl-N-(1-methyl-1H-pyrazol-3-yl)-3-(1-(((1R)-2,2,2-trifluoro-1-methylethyl)oxy)-6-phthalazinyl)benzamide;
3-(1-((2-fluoro-1-(fluoromethyl)ethyl)oxy)-6-phthalazinyl)-4-methyl-N-(1-methyl-1H-pyrazol-5-yl)benzamide;
N-cyclopropyl-3-(1-((2-fluoro-1-(fluoromethyl)ethyl)oxy)-6-phthalazinyl)-4-methylbenzamide;
4-methyl-3-(1-(1-methylpropyl)-6-phthalazinyl)benzamide;
4-methyl-3-(1-(1-methylethyl)-6-phthalazinyl)-N-(2,2,2-trifluoroethyl)benzamide;
N-cyclopropyl-4-methyl-3-(1-(((1S)-2,2,2-trifluoro-1-methylethyl)oxy)-6-phthalazinyl)benzamide;
N-cyclopropyl-4-methyl-3-(1-(((1R)-2,2,2-trifluoro-1-methylethyl)oxy)-6-phthalazinyl)benzamide;
4-methyl-3-(1-(1-methylethyl)-6-phthalazinyl)benzamide;
4-methyl-N-(1-methylcyclopropyl)-3-(1-(((1S)-2,2,2-trifluoro-1-methylethyl)oxy)-6-phthalazinyl)benzamide;
3-(1-(1,1-dimethylethyl)-6-phthalazinyl)-4-methyl-N-(1-methylethyl)benzamide;
4-methyl-N-(1-methylcyclopropyl)-3-(1-((2S)-2-methyl-1-pyrrolidinyl)-6-phthalazinyl)benzamide;
4-methyl-N-(1-methylcyclopropyl)-3-(1-(((1S)-2,2,2-trifluoro-1-methylethyl)oxy)-6-phthalazinyl)benzamide;
4-methyl-N-(1-methylcyclopropyl)-3-(1-(((1R)-2,2,2-trifluoro-1-methylethyl)oxy)-6-phthalazinyl)benzamide;
4-methyl-N-(1-methylcyclopropyl)-3-(1-(1-methylethyl)-6-phthalazinyl)benzamide;
N-cyclopropyl-3-(1-(1,1-dimethylethyl)-6-phthalazinyl)-4-methylbenzamide;
4-methyl-N-(1-methyl-1H-pyrazol-3-yl)-3-(1-(((1R)-2,2,2-trifluoro-1-methylethyl)oxy)-6-phthalazinyl)benzamide;
4-methyl-N-(1-methyl-1H-pyrazol-3-yl)-3-(1-(((1S)-2,2,2-trifluoro-1-methylethyl)oxy)-6-phthalazinyl)benzamide;
4-methyl-N-(2,2,2-trifluoroethyl)-3-(1-(((1R)-2,2,2-trifluoro-1-methylethyl)oxy)-6-phthalazinyl)benzamide;
4-methyl-N-(2,2,2-trifluoroethyl)-3-(1-(((1S)-2,2,2-trifluoro-1-methylethyl)oxy)-6-phthalazinyl)benzamide;
N-cyclopropyl-3-(1-(2,2-dimethylpropyl)-6-phthalazinyl)-4-methylbenzamide;
3-(1-(2,2-dimethylpropyl)-6-phthalazinyl)-4-methyl-N-(1-methylcyclopropyl)benzamide;
3-(1-(2,2-dimethylpropyl)-6-phthalazinyl)-4-methyl-N-(2,2,2-trifluoroethyl)benzamide;
4-methyl-N-(2,2,2-trifluoroethyl)-3-(1-(((1R)-2,2,2-trifluoro-1-methylethyl)oxy)-6-phthalazinyl)benzamide;
4-methyl-N-(2,2,2-trifluoroethyl)-3-(1-(((1S)-2,2,2-trifluoro-1-methylethyl)oxy)-6-phthalazinyl)benzamide;
3-(1-(1,1-dimethylethyl)-6-phthalazinyl)-4-methyl-N-(1-methyl-1H-pyrazol-5-yl)benzamide;
3-(1-(1,1-dimethylethyl)-6-phthalazinyl)-4-methyl-N-(2,2,2-trifluoroethyl)benzamide;
4-methyl-N-1,3,4-thiadiazol-2-yl-3-(1-(((1R)-2,2,2-trifluoro-1-methylethyl)oxy)-6-phthalazinyl)benzamide;
4-methyl-N-1,3,4-thiadiazol-2-yl-3-(1-(((1S)-2,2,2-trifluoro-1-methylethyl)oxy)-6-phthalazinyl)benzamide;
4-methyl-N-1,3-thiazol-2-yl-3-(1-(((1S)-2,2,2-trifluoro-1-methylethyl)oxy)-6-phthalazinyl)benzamide;
4-methyl-N-1,3-thiazol-2-yl-3-(1-(((1R)-2,2,2-trifluoro-1-methylethyl)oxy)-6-phthalazinyl)benzamide;
3-(1-(1,1-dimethylethyl)-6-phthalazinyl)-4-methyl-N-(1-methylcyclopropyl)benzamide;
N-cyclopropyl-4-methyl-3-(1-((1S)-2,2,2-trifluoro-1-methylethyl)-6-phthalazinyl)benzamide;
N-cyclopropyl-4-methyl-3-(1-((1 S)-2,2,2-trifluoro-1-methylethyl)-6-phthalazinyl)benzamide;
N-cyclopropyl-4-methyl-3-(1-(1-(trifluoromethyl)ethenyl)-6-phthalazinyl)benzamide;

4-methyl-N-(1-methyl-1H-pyrazol-5-yl)-3-(1-((1R)-2,2,2-trifluoro-1-methylethyl)-6-phthalazinyl)benzamide;

4-methyl-N-(1-methyl-1H-pyrazol-5-yl)-3-(1-((1S)-2,2,2-trifluoro-1-methylethyl)-6-phthalazinyl)benzamide;

4-methyl-N-(1-methyl-1H-pyrazol-5-yl)-3-(1-(2,2,2-trifluoro-1-hydroxy-1-methylethyl)-6-phthalazinyl)benzamide;

N-cyclopropyl-4-methyl-3-(1-(1-(trifluoromethyl)cyclopropyl)-6-phthalazinyl)benzamide;

4-methyl-N-(1-methyl-1H-pyrazol-5-yl)-3-(1-(R)-2,2,2-trifluoro-1-methylethyl)-6-phthalazinyl)benzamide;

4-methyl-N-(1-methyl-1H-pyrazol-5-yl)-3-(1-(S)-2,2,2-trifluoro-1-methylethyl)-6-phthalazinyl)benzamide;

N-cyclopropyl-4-methyl-3-(1-((1R)-2,2,2-trifluoro-1-methylethyl)-6-phthalazinyl)benzamide;

N-cyclopropyl-4-methyl-3-(1-((1S)-2,2,2-trifluoro-1-methylethyl)-6-phthalazinyl)benzamide;

N-cyclopropyl-4-methyl-3-(1-(2,2,2-trifluoro-1-hydroxy-1-methylethyl)-6-phthalazinyl)benzamide;

3-(1-(1-fluoro-1-methyl-6-phthalazinyl)-4-methyl-N-(1-methyl-1H-pyrazol-5-yl)benzamide;

4-methyl-N-(1-methyl-1H-pyrazol-5-yl)-3-(1-((1R)-2,2,2-trifluoro-1-hydroxy-1-methylethyl)-6-phthalazinyl)benzamide;

N-cyclopropyl-3-fluoro-4-methyl-5-(1-(((1R)-2,2,2-trifluoro-1-methylethyl)oxy)-6-phthalazinyl)benzamide;

N-cyclopropyl-3-fluoro-4-methyl-5-(1-(((1S)-2,2,2-trifluoro-1-methylethyl)oxy)-6-phthalazinyl)benzamide;

N-ethyl-4-methyl-3-(1-(((1S)-2,2,2-trifluoro-1-methylethyl)oxy)-6-phthalazinyl)benzamide; and N,4-dimethyl-3-(1-(((1S)-2,2,2-trifluoro-1-methylethyl)oxy)-6-phthalazinyl)benzamide.

DEFINITIONS

The following definitions should assist in understanding the invention described herein.

The term "comprising" is meant to be open ended, including the indicated component(s), but not excluding other elements.

The term "$C_{\alpha\text{-}\beta}$alkyl", when used either alone or within other terms such as "haloalkyl" and "alkylamino", embraces linear or branched radicals having $\alpha$ to $\beta$ number of carbon atoms (such as $C_1$-$C_{10}$). The term "alkyl" radicals include "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. The term alkoxy radicals include "lower alkoxy" radicals having one to six carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. Unless otherwise specified, the "aryl" group may be subsitituted, such as with 1 to 5 substituents including lower alkyl, hydroxyl, halo, haloalkyl, nitro, cyano, alkoxy and lower alkylamino, and the like. Phenyl substituted with —O—$CH_2$—O— or —O—$CH_2$—$CH_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 8-membered monocyclic groups such as cyclopropane, cyclobutane, cyclopentane and cyclohexane and partially saturated monocyclic groups such as cyclopentene, cyclohexene or cyclohexadiene. The partially saturated groups are also encompassed in the term "cycloalkenyl" as defined below.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms and, for example, lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heteroaryl" also embraces bicyclic radicals wherein 5- or 6-membered heteroaryl radicals are fused/condensed with aryl radicals or unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydrobenzo[1,4]dioxinyl and dihydrobenzofuryl]. Examples of heterocyclic radicals include five to ten membered fused or unfused radicals.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "alkylthio" and "thioalkoxyl" embrace radicals containing a linear or branched alkyl radical, of one to ten carbon atoms, attached to a divalent sulfur atom. An example of "alkylthio" is methylthio, ($CH_3S$—).

The term "Formula I" includes any sub formulas, such as Formula II. Similarly, the terms "Formula III" and "Formula IV" includes any sub formulas.

The term "pharmaceutically-acceptable" when used with reference to a compound of Formulas I-IV is intended to refer to a form of the compound that is safe for administration. For example, a free base, a salt form, a solvate, a hydrate, a prodrug or derivative form of a compound of Formulas I, II, III or of Formula IV, which has been approved for mammalian use, via oral ingestion or any other route of administration, by a governing body or regulatory agency, such as the Food and Drug Administration (FDA) of the United States, is pharmaceutically acceptable.

Included in the compounds of Formulas I-IV are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I, II, III and IV may be prepared from an inorganic acid or from an organic acid. Examples of such inorganic acids are hydrochloric, hydrobromic, hydroiodic, hydrofluoric, nitric, carbonic, sulfonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I, II, III and IV include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, II, III or IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative, which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formulas I, II, III or IV. A "pharmaceutically-acceptable prodrug" as used herein, denotes a prodrug, which is pharmaceutically acceptable. Pharmaceutically acceptable modifications to the compounds of Formulas I-IV are readily appreciated by those of ordinary skill in the art.

The compound(s) of Formula I, II, m and IV may be used to treat a subject by administering the compound(s) as a pharmaceutical composition. To this end, the compound(s) can be combined with one or more carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies.

The term "leaving groups" (also denoted as "LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I, II, III and IV. The compounds of Formulas I-IV can be synthesized according to the procedures described in the following Schemes 1-4, wherein the substituents are as defined for Formulas I-IV, above, except where further noted. The synthetic methods described below are merely exemplary, and the compounds of the invention may also be synthesized by alternate routes as appreciated by persons of ordinary skill in the art.

The following list of abbreviations used throughout the specification represent the following and should assist in understanding the invention:
ACN, MeCN-acetonitrile
$AgNO_3$-silver nitrate
BSA-bovine serum albumin
BOP-benzotriazol-1-yl-oxy hexafluorophosphate
CDI-carbonyldiimidazole
$Cs_2CO_3$-cesium carbonate
$CHCl_3$-chloroform
$CH_2Cl_2$, DCM-dichloromethane, methylene chloride
DCC-dicyclohexylcarbodiimide
DIC-1,3-diisopropylcarbodiimide
DEEA,$(iPr)_2NEt$-diisopropylethylamine
DME-dimethoxyethane
DMF-dimethylformamide
DMAP-4-dimethylaminopyridine
DMSO-dimethylsulfoxide
EDC-1-(3-dimethylaminopropyl)-3-ethylcarbodiimide
$Et_2O$-diethyl ether
EtOAc-ethyl acetate
FBS-fetal bovine serum
G, gm-gram
h, hr-hour
$H_2$-hydrogen
$H_2O$-water
HATU-O-(7-azabenzotriazol-1-yl)-N,N,N',N'-tetramethyluroniumhexafluorophosphate
HBr-hydrobromic acid
HCl-hydrochloric acid
HOBt-1-hydroxybenzotriazole hydrate
HOAc-acetic acid
HPLC-high pressure liquid chromatography
IPA, IpOH-isopropyl alcohol
$K_2CO_3$-potassium carbonate
KI-potassium iodide
LG-leaving group
$MgSO_4$-magnesium sulfate
MS-mass spectrum
MeOH-methanol
$N_2$-nitrogen
$NaCNBH_3$-sodium cyanoborohydride
$Na_2CO_3$-sodium carbonate
$NaHCO_3$-sodium bicarbonate
NaH-sodium hydride
$NaOCH_3$-sodium methoxide
NaOH-sodium hydroxide
$Na_2SO_4$-sodium sulfate
NBS-N-bromosuccinimide
$NH_4Cl$-ammonium chloride
$NH_4OH$-ammonium hydroxide
NMP-N-methylpyrrolidinone
$P(t-bu)_3$-tri(tert-butyl)phosphine
PBS-phospate buffered saline
Pd/C-palladium on carbon
$Pd(PPh_3)_4$-palladium(0)triphenylphosphine tetrakis
$Pd(dppf)Cl_2$-palladium(1,1-bisdiphenylphosphinoferrocene) II chloride
$Pd(PhCN)_2Cl_2$-palladium di-cyanophenyl dichloride
$Pd(OAc)_2$-palladium acetate
$Pd_2(dba)_3$-tris(dibenzylideneacetone) dipalladium
PyBop-benzotriazol-1-yl-oxy-tripyrrolidino-phosphonium hexafluorophosphate
RT-room temperature
TBTU-O-benzotriazol-1-yl-N,N,N',N'-tetramethyluronium tetrafluoroborate
TEA, $Et_3N$-triethylamine
TFA-trifluoroacetic acid
THF-tetrahydrofuran
UV-ultraviolet light Scheme 1

A 1-chloro-6-halo (X=halogen such as Br, I, Cl or F) substituted phthalazine 5, (where both $A_1$ and $A_2$ are each carbon) or aza-phthalazine 5 (where one of $A_1$ or $A_2$ is nitrogen), or diaza-phthalazine 5 (where both A₁ and A₂ are each nitrogen), and which are generally referred to herein as the C-D ring portion of the compounds of Formulas I-IV, can be prepared according to the method generally described in Scheme 1. As shown, a 4-halo-2-methyl cyanobenzene 1 can be treated with a source of bromine under suitable conditions, such as N-bromosuccinimide (commonly referred to as NBS) in the presence of UV light, for a time period to form 2,2-dibromomethyl adduct 2. The 4-cyano-3-dibromo methylphenyl intermediate 2 can be reacted with silver nitrate, in the presence of a suitable solvent such as acetonitrile, to form the 6-halo-hydroxybenzenesuccinimide compound 3. Formation of compound 3 may require heat, up to and including reflux temperatures depending on the particular solvent and concentration, as appreciated by those skilled in the art. Compound 3 can then be treated with hydrazine to form the corresponding 6-halo-1-hydroxyphthalazine 4. This reaction generally produces reasonable yields of product 4 at RT when allowed to react for a prolonged period of time, such as about 24 hours. 4-Hydroxyphthalazine 4 can then be reacted with a suitable chloride source, such as phosphorus oxychloride, in the presence of a suitable solvent, to convert the 2-hydroxy group to the corresponding 1-chloride phthalazine 5. 6-Halo-substituted phthalazine 5 is a useful intermediate for coupling the R³ ring system, with or without a "B" linker, as illustrated in Formulas I-IV (R³ is a phenyl ring in Formulas II and IV).

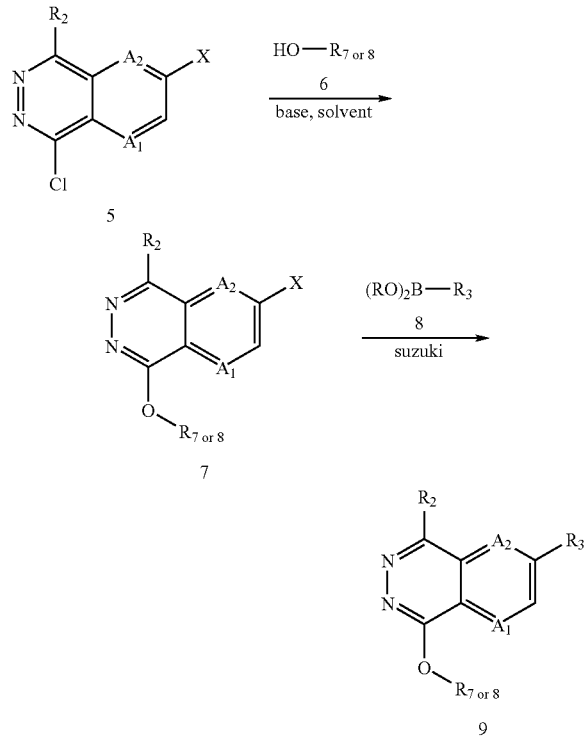

Scheme 2

A compound 9 of Formulas I-IV can be prepared according to the method generally described in Scheme 2. As shown, 6-halo-substituted phthalazine 5 (see scheme 1 above) can be treated with an R¹ group having a suitable nucleophilic species, such as a hydroxyl-R₁ compound 6 as shown (R¹=—OR⁷ or OR⁸) or thio-compound (R¹=—SR⁷ or —SR⁸; not shown), in the presence of a suitable base capable of deprotonating the hydroxyl group, such as sodium hydride, in the presence of a solvent to afford the desired 3-OR⁷ ᵒʳ ⁸ substituted phthalazine 7 (see also example 2 below). The nucleophile (R¹) may alternatively be a nitrogen nucleophile (R¹=—NR⁷ ᵒʳ ⁸), which can displace the chloride of the phthalazine in the presence of a suitable base by conventional methods, as appreciated by those skilled in the art. Heat may or may not be required to effect the transformation depending upon the particular substrates involved. Methods to make similar intermediate compounds are also described in co-pending U.S. patent application Ser. No. 11/367,123, which disclosure is herein incorporated by reference in its entirety.

A desired 1-ether-substituted-6-halo-phthalazine 7 can be reacted with a desired R³-substituted boronic acid 8 in a Suzuki-type or Buchwald-type coupling reaction to afford the desired 3-OR⁷ ᵒʳ ⁸-6-R³ substituted phthlazines 9. Note: R3 as shown in scheme 2 above is a 6-membered aryl or heteroaryl ring as depicted in Formulas I, II, III and IV. The Suzuki method is a reaction using a borane reagent, such as a dioxaborolane intermediate 8 (also described in scheme 3 below as a borane B-A intermediate 8), and a suitable leaving group containing reagent, such as the 6-X-phthalazine 5 (X is a leaving group "LG", which may be an I or Br). As appreciated to one of ordinary skill in the art, Suzuki reactions also utilize a palladium catalyst. Suitable palladium catalysts include Pd(PPh₃)₄, Pd(OAc)₂ or Pd(dppf)Cl₂. Where LG is a halide, the halide may be an iodide, a bromide or even a chloride (chloro-pyridyl or chloro-picolinyl B rings undergo Suzuki reactions in the presence of Pd(OAc)₂). Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular phthalazine 7 and/or boronic acid 8, as appreciated by those skilled in the art. In addition, where R³ is an aromatic moiety, such as phenyl, the reaction may be complete in a short period of time with heat.

Further, the boronic acid 8 may be any suitable desired boronic acid having the general formula (RO)₂B—R³ (where "B" is a direct bond) or (RO)₂B-"B"-R³, (where "B" is a spacer such as an —(CR⁵R⁶)₀₋₂—, —C(=O)—, —N(R⁶)—, —O— or —S(=O)₀₋₂—) as defined in Formulas I-IV. The boronic acid may also be a cyclic boronate (not shown). In this fashion, desired R¹ groups, such as amino or ether R¹ groups, and R³ groups such as aryl or heteroaryl R³ groups, can be installed into the phthalazine core 7. The desired boronic acid compounds 8 may generally be made as illustrated in scheme 3 below. Other known metal coupling chemistry, such Stille, Kumada, Negishi coupling methods, and the like, may be employed to couple phthalazines 5 or 7 to desired cyclic R³-substituted moieties.

Alternatively, the boronic acid use in scheme 2 may be of the formula (RO)₂B—R³ wherein R³ is a phenyl or 6-membered heteroaryl (see Formulas I, II and III herein) substituted also with carboxylic acid (not shown), such as a desireably substituted benzoic acid. The acid may be masked, and isolated, as an ester, salt or other conventional protected form, for use during the Suzuki reaction. The ester or salt may then be deprotected, and the free acid may be coupled to an amine, or other desired nucleophile, utilizing conventional coupling methods known in the art to build linker L¹. In this fashion, a desired R⁴ groups, such as an amino-substituted R⁴ may be used to couple to the free acid to afford the desired amide adduct (where L¹ is an amide linker). Scheme 3 below further described methods of preparing amide, carbamate, urea, and other L¹ linkers defined herein.

Alternatively, the coupling method described in Scheme 2 may also be used to couple a C-D ring (phthalazine) to a desired R¹ group, such as a B ring, without having an A ring (or an $R^{10}$ or $R^{11}$ substitution) in place (see scheme 3 and Example 2 below). Halo-substituted-NH$_2$-B rings may be coupled via a Suzuki reaction to a dioxaborolane phthalazine 5 or 7, and the amine group may then be converted to an isocyanate, for example, or any other desired group for coupling the A ring (or an $R^{10}$ or $R^{11}$ substitution) via the desired linker.

Scheme 3

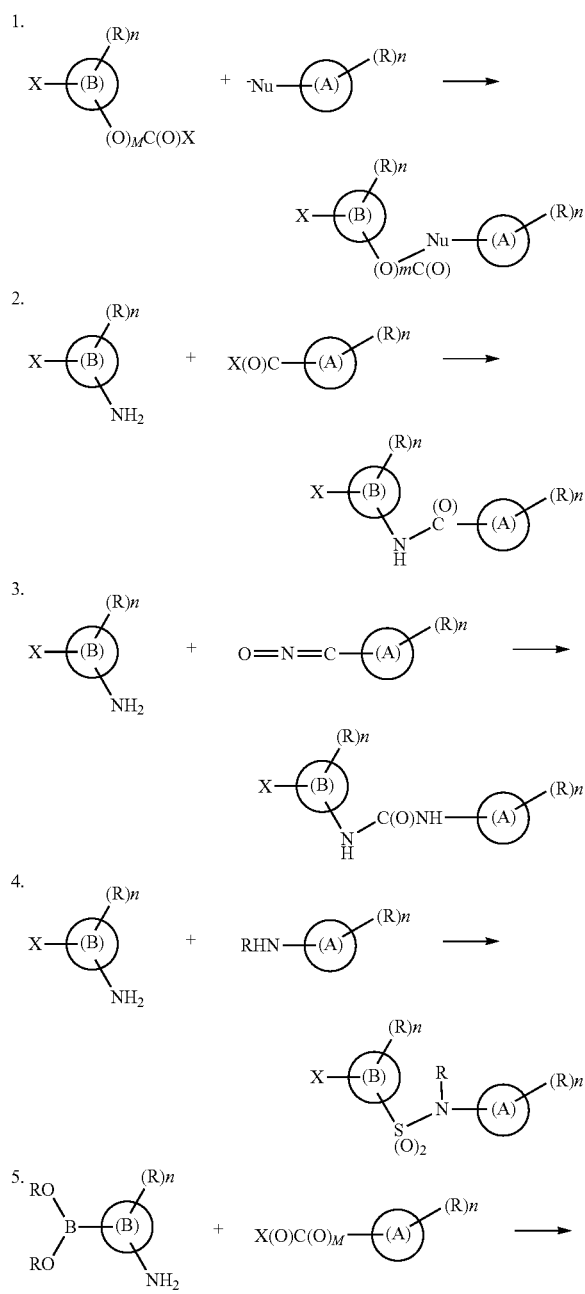

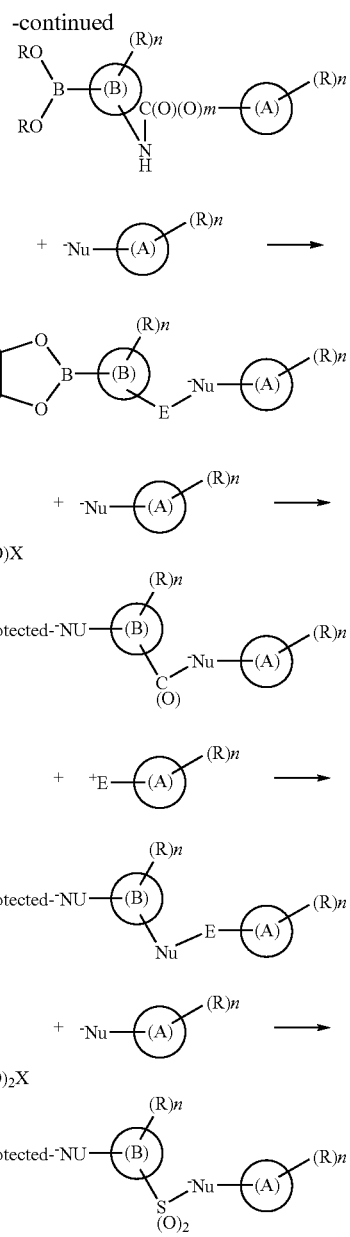

$R^3$ ring systems, generally designated and referred to in Scheme 3, and throughout the specification, as the "B ring" may be substituted with various substitutions as specified herein. For example, the substitution may be a linker, such as amino, carboxyl, sulfonyl, amido, and urea linker as defined herein in Formulas I, II, II and IV (designated generally as $L^1$), connecting various substitutions, including $R^4$ groups and $R^{11}$ rings (generally designated and referred to in Scheme 3, and throughout the specification, as the "A" group or "A" ring) to the $R^3$ ring (aryl or heteraryl in Formulas I-IV) ("B ring"). This linker may be attached by various coupling methods as described in Scheme 3. Each of the nine sub-schemes, numbered 1-9 above and described below, utilize the following meanings for $(R)_n$, X, Nu⁻, E⁺ and m: $(R)_n$ refers to n number of $R^{10}$, $R^{11}$, $R^{15}$ and $R^{16}$ substitutions wherein n is an integer from 0-9; X refers generally to a "leaving group" such as a halide (bromine, chlorine, iodine or fluorine), alkylsulfonate and other known groups (also see definitions herein); Nu⁻ refers generally to a nucleophilic species such as a primary or secondary amine, an oxygen, a sulfur or a anionic carbon species—examples of nucleophiles include, without limitation, amines, hydroxides, alkoxides and the like; $E^+$ refers generally to an electrophilic species, such as the carbon atom of a carbonyl, which is susceptible to nucleophilic attack or readily eliminates—examples of suitable electrophilic carbonyl species include, without limitation, acid halides, mixed anhydrides, aldehydes, carbamoyl-chlorides, sulfonyl chlorides, acids activated with activating reagents such as TBTU, HBTU, HATU, HOBT, BOP, PyBOP and carbodiimides (DCC, EDC, CDI and the like), and other electrophilic species including halides, isocyanates, daizonium ions and the like; and m is either 0 or 1.

The coupling of ring B to A, as shown as products in sub-schemes 1-9, can be brought about using various conventional methods to link ring B and A together. For example, an amide or a sulfonamide linkage, as shown in sub-schemes 2 and 4, and 7 and 9 where the Nu− is an amine, respectively, can be made utilizing an amine on either the B or A groups and an acid chloride or sulfonyl chloride on the other of either the B or A groups. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates as illustrated in sub-schemes 5 and 1 where Nu− is an amine, anhydrides as illustrated in sub-scheme 1 where Nu− is an oxygen, reverse amides as generally illustrated in sub-scheme 8 where Nu− is an amine and E+ is an acid chloride, ureas as illustrated in sub-scheme 3, thioamides and thioureas where the respective carbonyl oxygen is a sulfur, thiocarbamates where the respective carbonyl oxygen and/or carbamate oxygen is a sulfur, and the like. While the above methods are so described, they are not exhaustive, and other methods for linking groups A and B together may be utilized as appreciated by those skilled in the art.

Although sub-schemes 1-9 are illustrated as having the nucleophilic and electrophilic coupling groups, such as the amino group and acid chloride groups illustrated in sub-scheme 2, directly attached to the substrate, either the A group or B ring, in question, the invention is not so limited. It is contemplated herein that these nucleophilic and/or electrophilic coupling groups may be tethered from their respective ring. For example, the amine group on the B ring, and/or the acid halide group on the A group or ring, as illustrated in sub-scheme 2, may be removed from direct attachment to the ring by a one or more atom spacer, such as by a methylene, ethylene spacer or the like. As appreciated by those skilled in the art, such spacer may or may not affect the coupling reactions described above, and accordingly, such reaction conditions may need to be modified to effect the desired transformation.

The coupling methods described in sub-schemes 1-9 of scheme 3 are also applicable for coupling desired A groups or rings to desired DC-B intermediates, such as to substituted phthalazine benzoic acids or substituted aza- or diazaphthalazine benzoic acids (not shown), to synthesize desired compounds of Formulas I-IV. For example, a desirably substituted phthalazine benzoic acid maybe reacted with a desirably substituted primary or secondary amine, such as an $NHR^{10}R^{10}$ or $NHR^{10}R^{11}$ group in the presence of a suitable solvent and a known coupling reagent, such as TBTU, HATU, CDI or others, to prepare the desired A-BCD amide bond, and the final compound of Formulas I-IV.

Note that the B-A moiety is connected through a linker "$L^1$". "$L^1$" may be any linker generally defined by the $R^4$ substitutions in Formulas I-IV, and particularly, it includes, without limitation, an amide, a urea, a thiourea, a thioamide, a carbamate, an anhydride, a sulfonamide and the like, as described in Scheme 3 above.

Further, the amine may be protected (not shown), such as with BOC—ON, while further substituents are coupled to the B ring, prior to or after coupling the B ring to an A ring or A group to form the desired $R^3$ group.

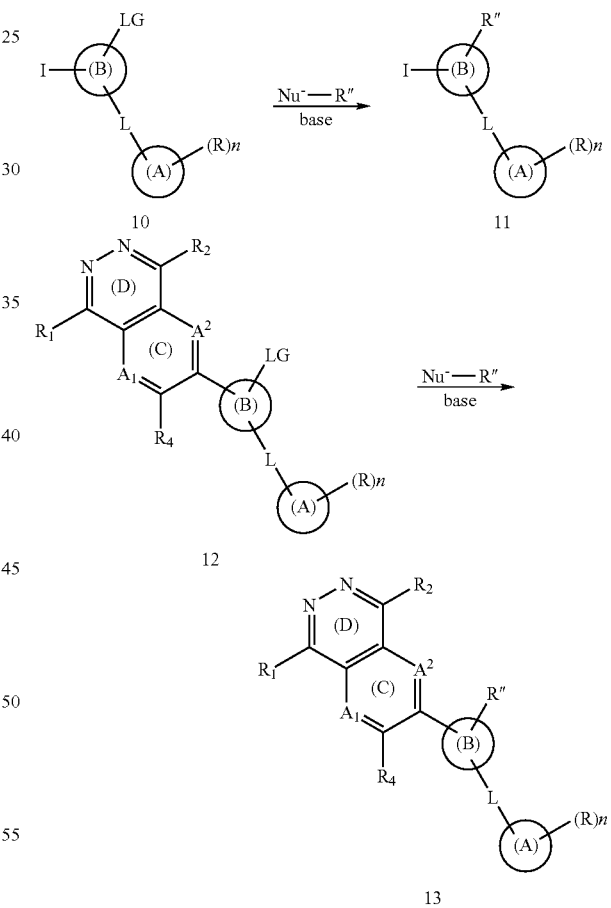

Scheme 4

Various $R^3$ and $R^{3a}$ substitutions (designated generally as R" groups in compounds 11 and 13) can be installed on the B ring of Formulas I-IV, with or without the C-D ring system attached, as described in Scheme 4. For instance, compounds II and 13 may be made by the method described in Scheme 4. As shown, iodinated aryl B ring compounds 10 and compounds 12 may contain suitable leaving groups, such as a fluoride, at a desired position for substitution. These intermediates (compounds 10 and 12) may be reacted with desirable nucleophilic R" groups, such as alkoxides, amines and the like, in the presence of a suitable base, such as a hydride or borohydride, to covalently bind the R" group to the B ring. Alternatively, the B ring may have a nucleophile, such as a hydroxide or an amine, which may be further functionalized as desired via standard chemical methodology, as appreciated by those skilled in the art.

Scheme 5 (Method F)

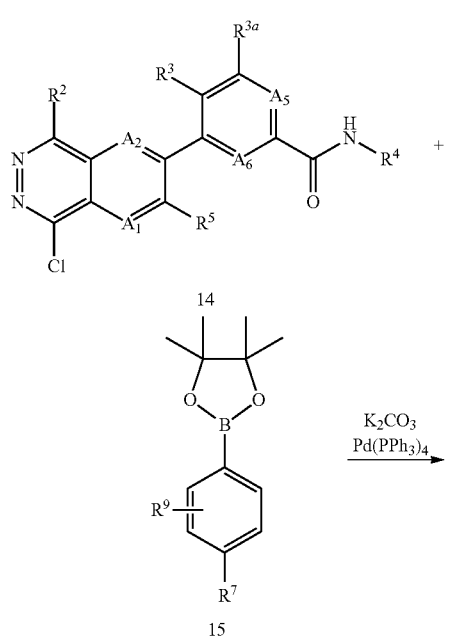

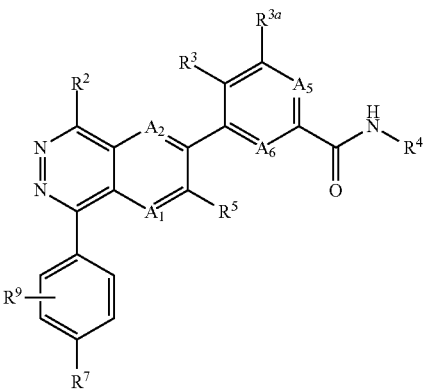

Various $R^1$ substitutions (where $R^1$ is an aromatic group as shown in compounds 15 and 16) can be installed on the phthalazine ring of Formulas I and III, with or without the aryl/heteroaryl B ring attached, as described in Scheme 5, designated as Method F. As shown, a boronate compound 15 may be reacted with a chloro phthalazine 14 in a Suzuki or Suzuki-like reaction, with a suitable base, such as those described herein, to afford desired compounds 16

Scheme 6 (Method H)

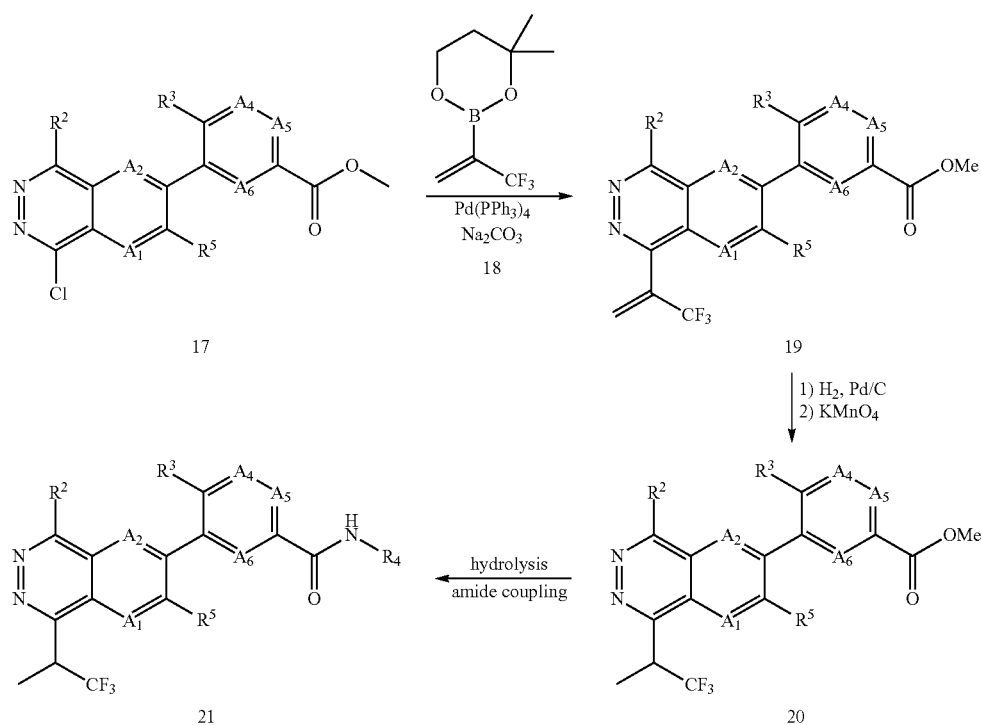

Various $R^1$ substitutions (where $R^1$ is linear hydrocarbon group as shown in compounds 20 and 21) can be installed on the phthalazine ring of Formulas I and III, with or without the aryl/heteroaryl B ring attached, as described in Scheme 6, designated as Method H. As shown, a boronate compound 18 may be reacted with a chloro phthalazine 17 in a Suzuki or Suzuki-like reaction, with a suitable base, such as those described herein, to afford desired adduct compound 19. Compound 19, may then be further functionalized, such as reduced as shown above, to the corresponding desired compound 20 above. The protective ester of intermediate 20 can be hydrolyzed to the corresponding acid using conventional, known methods, and the acid (not shown) can be converted to the corresponding desired $L^1$ linker (amide as shown above) using known conventional methods, such as those described in scheme 3 herein above.

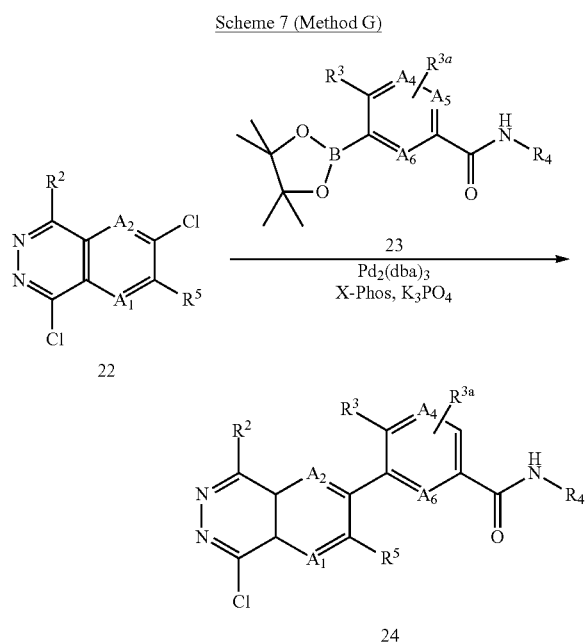

Alternatively, various desired compounds 24, of Formulas I-IV, may be made by building the bond between the phthalazine ring and B ring as shown in scheme 7 above, designated as Method G. As shown, a desired $L^1$-$R^1$ substituted aromatic boronate compound 23 may be reacted with a desired $R^1$ substituted chloro phthalazine 22 using a palladium catalyst, with a suitable base, such as those described herein, to afford desired adduct compound 24.

To enhance the understanding and appreciation of the present invention, the following specific examples (starting reagents, intermediates and compounds of Formulas I-IV) are set forth. It should be appreciated that the above general methods and specific examples below are merely for illustrative purposes only and are not to be construed as limiting the scope of this invention in any manner. The following analytical methods were used to purify and/or characterize the compounds, and intermediates, described in the examples below.

Analytical Methods:

Unless otherwise indicated, all HPLC analyses were run on a Agilent Model 1100 system with an Agilent Technologies Zorbax SB-$C_8$ (5µ) reverse phase column (4.6×150 mm; Part no. 883975-906) run at 30° C. with a flow rate of about 1.50 mL/min. The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Agilent Technologies XDB-$C_8$ (3.5µ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation utilizing one of the following two columns and methods:

(A) Using a 50×100 mm column (Waters, Exterra, C18, 5 microns) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 minute gradient from 40% to 100% solvent B followed by a 5 minute flow of 100% solvent B. The gradient was followed by a 2 min return to 40% solvent B.

(B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1H$ NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

Example 1

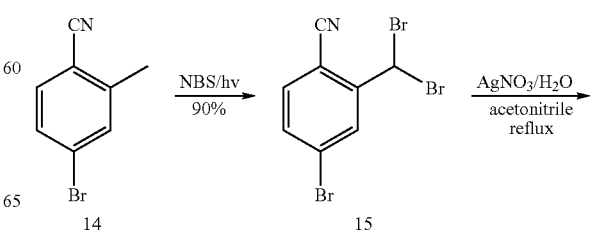

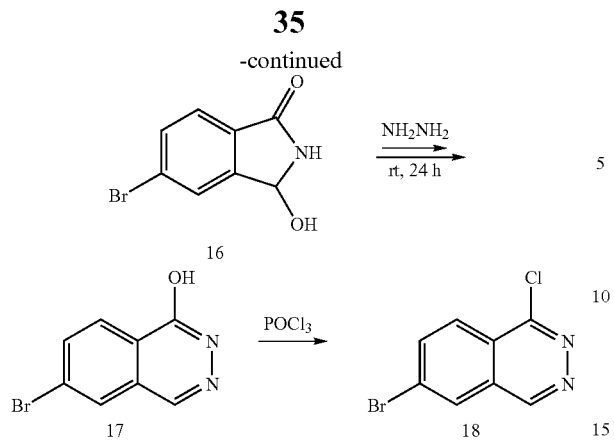

Synthesis of 6-bromo-1-chlorophthalazine (18)

Step A: A mixture of 4-bromo-2-methylbenzonitrile (14, 22 g, 112 mmol), benzoyl peroxide (2.7 g, 11 mmol) in 400 mL carbon tetrachloride was treated with n-bromosuccimide (21 mL, 247 mmol) at RT, then warmed up to 90° C. and stirred for 15 h. After 15 h of reaction, another 20 g of NBS was added and the reaction was stirred at 90° C. for another 10 h. Thin layer chromatography (TLC) revealed that all the starting material had been consumed. The reaction was cooled down to RT, filtered, and washed with hexane (100 mL). The filtrate was concentrated in vacuo, and the crude product was purified via flash chromatography (silica gel) eluting with a gradient of 4/1 hexanes/EtOAc to 2/1 hexanes/EtOAc, to give as a white solid, 4-bromo-2-(dibromomethyl)benzonitrile 15, 29.6 g. Found MS (ES+): 354 (M+H)$^+$.

Step B: To a solution of silver nitrate (AgNO$_3$, 6.86 mL, 176 mmol) in water (200 mL) refluxed under nitrogen was added 4-bromo-2-(dibromomethyl)benzonitrile (15, 29.6 g, 83.7 mmol) in 750 mL acetonitrile through a dropping funnel slowly in 1 h. The resulting mixture was refluxed under nitrogen and followed by MS periodically for 15 h (M+1=226, 228). As a TLC of the reaction showed some starting material was left, 10 g AgNO$_3$ and 50 mL H$_2$O was added and the reaction was refluxed for 96 h, after which all the starting material was consumed. The mixture was cooled down to room temperature, filtered and the filter cake was washed with 100 mL ethyl acetate. The filtrate was concentrated and neutralized with 1 N NaOH to a pH of about 7. The mixture was extracted with ethyl acetate (3×100 mL). The combined organics were washed with 50 mL brine, dried over anhydrous Na$_2$SO$_4$ and concentrated under reduced pressure. The crude product was purified via flash chromatography (silica gel) eluting with a gradient of 4/1 hexanes/EtOAc to 1/1 hexanes/EtOAc and 10% methanol to give a white solid, 5-bromo-3-hydroxyisoindolin-1-one 16, 17.6 g. Found MS (ES+): 228, 330 (M+H)$^+$.

Step C: A mixture of 5-bromo-3-hydroxyisoindolin-1-one (16, 17.0 g, 75 mmol), and hydrazine, monohydrate (60 mL, 1193 mmol) was stirred at room temperature for 15 h, after which a white solid precipitated out (M+1=225, 227). The mixture was diluted with 100 mL H$_2$O, neutralized with conc. HCl to a PH of about 7. The precipitate was filtrated and washed with 100 mL H$_2$O. The solid was collected, azeotropically dried with toluene (3×50 mL) and further dried in a vacuum oven at 45° C. for 15 h, to yield 6-bromophthalazin-1-ol 17 (16.1 g). Found MS (ES+): 225, 227 (M+H)$^+$.

Step D: A mixture of 6-bromophthalazin-1(2H)-one (17, 2.6 g, 12 mmol) in phosphorous oxychloride (11 mL, 116 mmol) was treated with diisopropylethylamine (2.0 mL, 12 mmol). The mixture was stirred at room temperature for 30 min, then warmed up to a temperature of between about 95-100° C. and stirred under nitrogen. The suspension (reaction) became a deep brown solution in about 30 min, then a yellow solid precipitated out. After about 3 h, all of the starting material was converted, as appeared by TLC, to product (M+1=243, 245). After the mixture was cooled down to room temperature, it was diluted with 50 mL CHCl$_3$ and cooled down to 0° C. The precipitate was filtrated, washed with 10 mL ice cool CHCl$_3$, collected and dried under vacuum, to afford 1.96 g of 6-bromo-1-chlorophthalazine 18, as yellow solid. Found MS (ES+): 243, 245 (M+H)$^+$.

Example 2

Method A

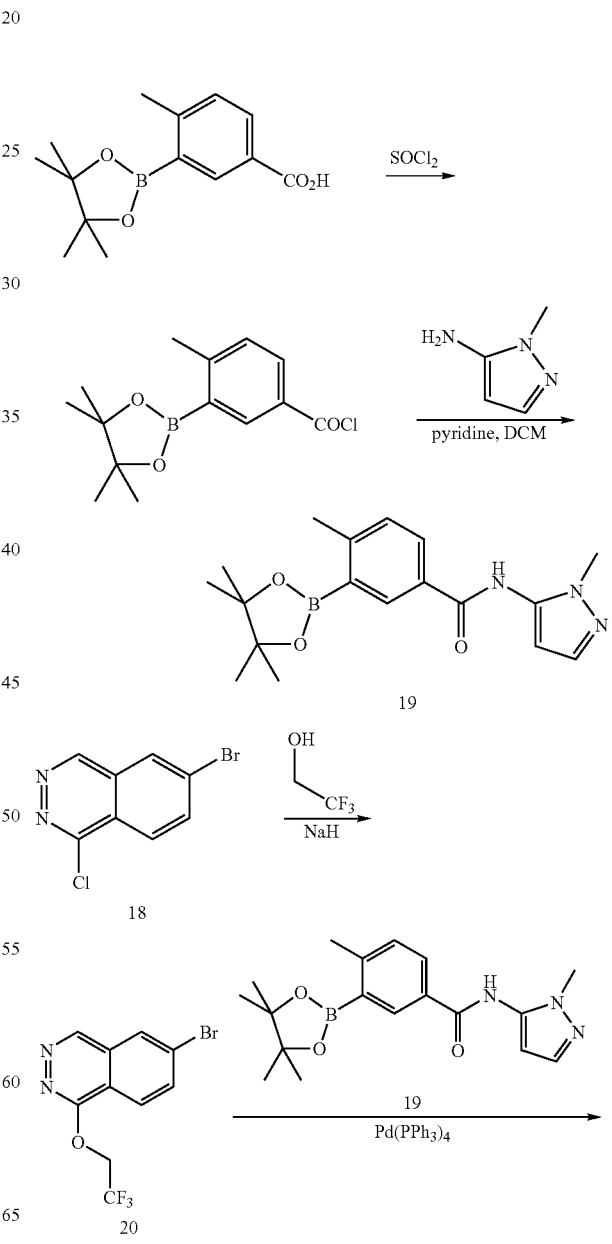

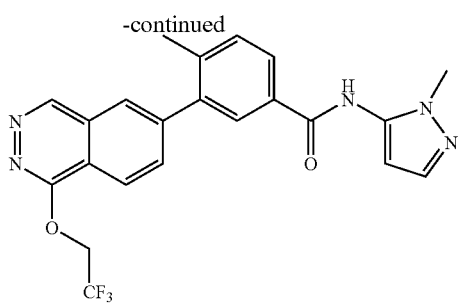

21

Example 2a

Synthesis of 4-Methyl-N-(1-methyl-1H-pyrazol-5-yl)-3-(4,4,5,5-tetramethyl-1,3,2-dioxaborolan-2-yl)benzamide (19)

To a 50 mL round-bottomed flask was added 4-methyl-3-(4,4,5,5-tetramethyl-1,3,2-dioxaborolan-2-yl)benzoic acid (2.0 g, 7.6 mmol) and thionyl chloride (14 ml, 191 mmol) and the reaction mixture was stirred at RT for 1 h. Excess thionyl chloride was evaporated under vacuum and the remaining trace amount was removed azeotropically by addition of toluene (5 mL) and repeated concentration under reduced pressure. To the resulting residue was added DCM (10 mL) followed by 1-methyl-1H-pyrazol-5-amine (1.1 g, 11 mmol) and pyridine (1.2 ml, 15 mmol). The reaction was stirred at reflux for 1 h then cooled to RT. The mixture was diluted with DCM, washed with water followed by sat. NaHCO₃, dried over MgSO₄, filtered and concentrated in vacuo. The brown residue was loaded on an ISCO 40 g column (eluted with 25-65% EtOAc in Hexanes) and purified to provide the title compound as an off-white amorphous solid. MS (ESI, pos. ion) m/z: 342.2 (M+1).

Example 2b

Synthesis of 6-Bromo-1-(2,2,2-trifluoroethoxy)phthalazine (20)

A solution of 2,2,2-trifluoroethanol (329 mg, 3.28 mmol) in 3.0 mL of THF and 3.0 mL of DMF at 0° C. was treated with sodium hydride (60% wt) (131 mg, 3.28 mmol) and the resulting mixture was stirred for 10 min, then solid 6-bromo-1-chlorophthalazine (400 mg, 1.64 mmol) was added in one portion. The mixture was stirred at RT for 1 h, poured into iced-cold saturated NH₄Cl solution, and extracted with EtOAc twice. The combined organic layers were dried over sodium sulfate, concentrated under vacuum. The residue was put on an ISCO 40 g column (eluted with 20-70% EtOAc in Hexanes) and purified to give title compound as a tan amorphous solid. MS (ESI, pos. ion) m/z: 309.0 (M+1).

Example 2c

Synthesis of 4-Methyl-N-(1-methyl-1H-pyrazol-5-yl)-3-(1-(2,2,2-trifluoroethoxy)phthalazin-6-yl)benzamide (21)

A mixture of 4-methyl-N-(1-methyl-1H-pyrazol-5-yl)-3-(4,4,5,5-tetramethyl-1,3,2-dioxaborolan-2-yl)benzamide (19, 143 mg, 0.42 mmol), 6-bromo-1-(2,2,2-trifluoroethoxy)phthalazine (20, 117 mg, 0.38 mmol), tetrakis(triphenylphosphine)palladium (22.0 mg, 0.019 mmol) in 2 mL of Dioxane and 0.5 mL of 2 N aqueous solution of Na₂CO₃ in a sealed glass tube was heated at 120° C. for 20 min in a Personal Chemistry microwave. The mixture was treated with 3 mL of 1 N NaOH and extracted with EtOAc (2×10 mL). The combined EtOAc layers were dried and concentrated. Purification of the residue on a 24 g ISCO column (eluted 75-100% EtOAc in Hexanes) provided the title compound 21 as an off-white solid. MS (ESI, pos. ion) m/z: 442.1 (M+1).

Example 3

Method B

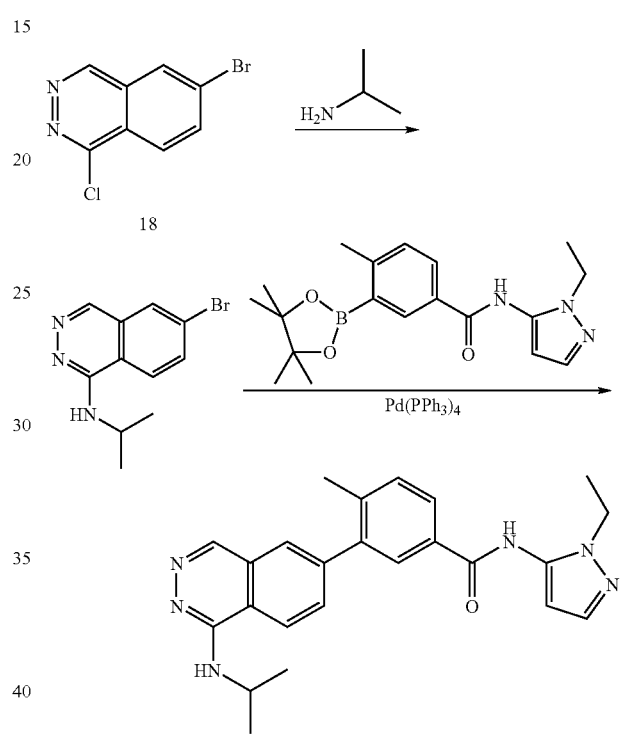

Example 3a

Synthesis of 6-Bromo-N-isopropylphthalazin-1-amine

In a sealed glass tube, a mixture of 6-bromo-1-chlorophthalazine (18, 0.40 g, 1.64 mmol), isopropyl amine (0.420 mL, 4.92 mmol) in NMP (2.0 mL) was heated in a microwave at 125° C. for 15 minutes. The resulting brown mixture was loaded on a 40 g ISCO column (eluted with 35-100% EtOAc in Hexanes) and purified to provide the title compound a light yellow crystalline solid. MS (ESI, pos. ion) m/z: 266.9 (M+1).

Example 3b

Synthesis of N-(1-Ethyl-1H-pyrazol-5-yl)-3-(1-(isopropylamino)phthalazin-6-yl)-4-methylbenzamide (22)

This compound was prepared according to the procedure described in Example 2c using the following starting materials: 6-Bromo-N-isopropylphthalazin-1-amine, tetrakis(triphenylphosphine)palladium and N-(1-ethyl-1H-pyrazol-5-yl)-4-methyl-3-(4,4,5,5-tetramethyl-1,3,2-dioxaborolan-2-yl)benzamide. MS (ESI, pos. ion) m/z: 415.2 (M+1).

Example 4

Method C

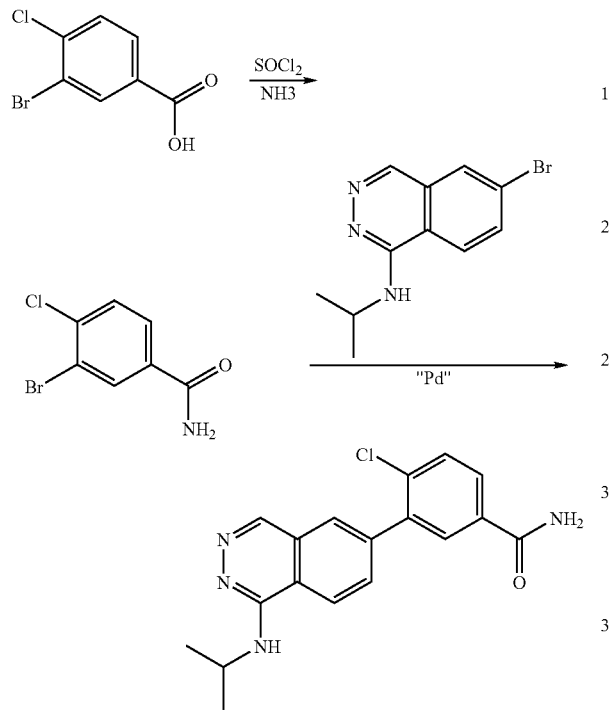

23

Example 4a

Synthesis of 3-Bromo-4-chlorobenzamide

To a mixture of 3-bromo-4-chlorobenzoic acid (5.07 g, 22 mmol, Alfa Aesar) and thionyl chloride (15 ml, 206 mmol) was added 1 drop of DMF and the reaction was heated at 80° C. After 2 h the excess $SOCl_2$ was removed in vacuo and the residue was azeotroped with toluene (2×). The residue was dissolved in 40 mL of $CH_2Cl_2$ and cooled to 0° C. Ammonia was bubbled into the reaction for 30 min. The mixture was diluted with 200 mL of $CH_2Cl_2$ and washed with saturated $NaHCO_3$. The aqueous layer was extracted with $CH_2Cl_2$ (3×) and the combined organic layers were washed with $H_2O$ and dried over $Na_2SO_4$ to give 3.81 g (75%) of a white amorphous solid. MS-m/z: 233.9, 235.9 [M+1].

Example 4b

Synthesis of 4-Chloro-3-(1-(isopropylamino)phthalazin-6-yl)benzamide (23)

A mixture of 6-bromo-N-isopropylphthalazin-1-amine (0.196 g, 0.74 mmol), bis(pinacolato)diboron (0.266 g, 1.0 mmol), potassium acetate (0.160 g, 1.6 mmol) and dichloro[1,1'-bis(diphenylphosphino)ferrocene]palladium (II) dichloromethane adduct (0.055 g, 0.075 mmol) in 4 mL of dioxane was heated at 125° C. for 20 min in the microwave (Emrys by Personal Chemistry). To the mixture was added 3-bromo-4-chlorobenzamide (0.241 g, 1.0 mmol), potassium carbonate (0.410 g, 3.0 mmol), tetrakis(triphenylphosphine)palladium (0) (0.077 g, 0.067 mmol), $H_2O$ (3 mL), EtOH (2 mL) and DME (3 mL). The reaction was resealed and heated at 80° C. After 4 h another portion of 3-bromo-4-chlorobenzamide (0.240 g) was added and the reaction was continued to be heated at 80° C. The reaction mixture was cooled to rt and the solvent was removed in vacuo. The residue was dissolved in MeOH and purified by reverse-phase HPLC (Gilson; Phenomenex Synergi, 4u MAX-RP, 150×21 20 mm) eluting with 0.1% TFA-$H_2O$:0.1% TFA $CH_3CN$ (9:1→1:9) to give the title compound 23 as a white amorphous solid. MS-m/z: 341.1 [M+1].

Example 5

Method D

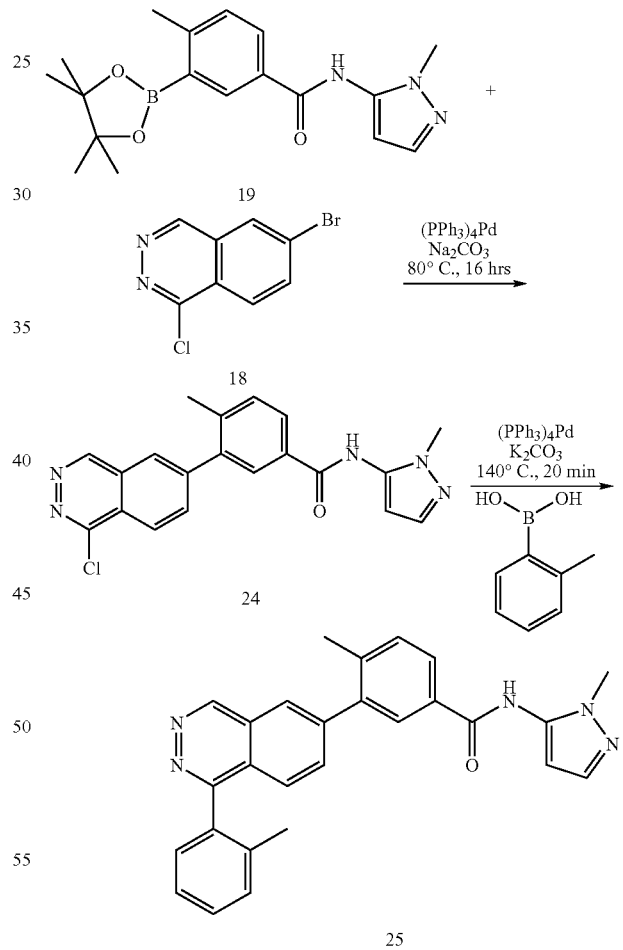

Example 5a

Synthesis of 3-(1-chlorophthalazin-6-yl)-4-methyl-N-(1-methyl-1H-pyrazol-5-yl)benzamide (24)

To a 150 mL round-bottomed flask was added 6-bromo-1-chlorophthalazine (18, 357 mg, 1465 μmol), tetrakis(triphenylphosphine)palladium (84.7 mg, 73.3 μmol), 4-methyl-N-(1-methyl-1H-pyrazol-5-yl)-3-(4,4,5,5-tetramethyl-1,3,2-dioxaborolan-2-yl)benzamide (500 mg, 1465 μmol), sodium carbonate (466 mg, 4396 μmol). The reagents were dissolved in DME:water mixture (15 mL, 4:1). The reaction mixture was stirred at 80° C. for 16 hours. The reaction mixture was evaporated and residue dissolved in ethyl acetate (20 mL) and washed with water (2×20 mL) and dried over MgSO$_4$ and rotovaped to yield the title compound 24 as a crude product. The crude product 24 was adsorbed on silica gel and chromatographed through a Redi-Sep® pre-packed silica gel column (12 g), eluting with a gradient of 65% to 80% EtOAc in DCM, to provide 3-(1-chlorophthalazin-6-yl)-4-methyl-N-(1-methyl-1H-pyrazol-5-yl)benzamide (24).

Example 5b

Synthesis of 4-methyl-N-(1-methyl-1H-pyrazol-5-yl)-3-(1-o-tolylphthalazin-6-yl)benzamide (25)

A glass microwave reaction vessel was charged with 3-(1-chlorophthalazin-6-yl)-4-methyl-N-(1-methyl-1H-pyrazol-5-yl)benzamide (65 mg, 172 μmol), o-tolylboronic acid (28 mg, 206 μmol), potassium carbonate (31 μl 516 μmol), tetrakis(triphenylphosphine)palladium (20 mg, 17 μmol) and DME:water:ethanol (7:3:2, 2 mL). The reaction mixture was stirred and heated in a Smith Synthesizer® microwave reactor (Personal Chemistry, Inc., Upssala, Sweden) at 140° C. for 20 mins.

The reaction mixture was evaporated and residue dissolved in EtOAc (20 mL) and washed with water (2×20 mL) and dried over sodium sulfate and rotovaped to yield crude product 25. The crude product 25 was chromatographed through a Redi-Sep® pre-packed silica gel column (12 g), eluting with a gradient of 50% to 75% ethyl acetate in hexane, to provide 4-methyl-N-(1-methyl-1H-pyrazol-5-yl)-3-(1-o-tolylphthalazin-6-yl)benzamide (25). MS (ESI, pos. ion) m/z: (M+1) 434.2

Example 6

Method E

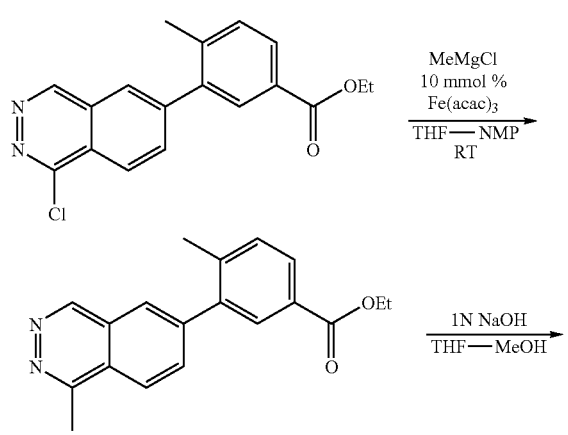

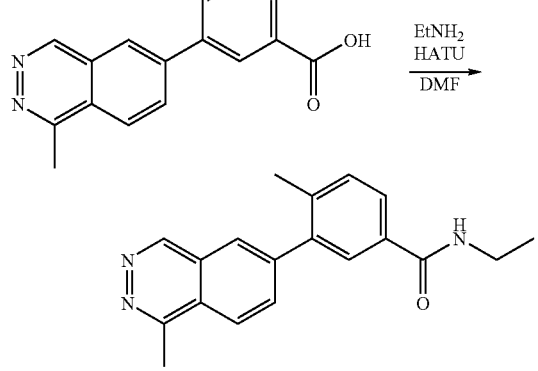

Synthesis of N-Ethyl-4-methyl-3-(1-methylphthalazin-6-yl)benzamide (26)

Step 1: Ethyl 4-methyl-3-(1-methylphthalazin-6-yl)benzoate

A 150-ml round-bottom flask under argon was charged with ethyl 3-(1-chlorophthalazin-6-yl)-4-methylbenzoate (358 mg, 1096 μmol), iron(III) acetylacetonate (38.7 mg, 109.6 □mol), THF (4200 μl), and 1-methyl-2-pyrrolidinone (420 μl). Methylmagnesium bromide (1.4M solution in toluene/tetrahydrofuran (75:25); 1174 μl, 1643 μmol) was then added via a syringe to the resulting orange red suspension, causing an immediate color change to brown, and finally to violet. The resulting mixture was stirred for 10 min, and the reaction (which remained a suspension) was diluted with EtOAc and carefully quenched with a few drops of 10% aqueous HCl solution. The mixture was washed with saturated aqueous NaHCO$_3$ solution and the organic layer was dried (MgSO$_4$), filtered, and concentrated in vacuo. Combi-Flash purification (20% to 90% EtOAc in Hexanes) afforded ethyl 4-methyl-3-(1-methylphthalazin-6-yl)benzoate as a light golden brown oil. MS (ES+): 307.1 (M+H)$^+$.

Step 2: 4-Methyl-3-(1-methylphthalazin-6-yl)benzoic acid

A solution of ethyl 4-methyl-3-(1-methylphthalazin-6-yl)benzoate (51.7 mg, 169 μmol) in tetrahydrofuran (800 μl) and methanol (400 μl) was added 1N aqueous sodium hydroxide solution (338 μl, 338 μmol) and stirred at RT for 18 h. The reaction was concentrated in vacuo and the residue was taken up in water and the pH was adjusted with 10% aqueous HCl solution to ~7. The aqueous mixture was extracted with 15% MeOH/CHCl$_3$ (3×) and the organic extracts were combined, dried (MgSO$_4$), filtered, and concentrated in vacuo to give 4-methyl-3-(1-methylphthalazin-6-yl)benzoic acid as a maize solid. MS (ES+): 279.1 (M+H)$^+$.

Step 3: N-Ethyl-4-methyl-3-(1-methylphthalazin-6-yl)benzamide (26)

Into a 15-ml round-bottom flask were added 4-methyl-3-(1-methylphthalazin-6-yl)benzoic acid (51 mg, 183 μmol), hatu (105 mg, 275 μmol), ethylamine (2M solution in THF (275 μl, 550 μmol), and chloroform (1000 μl). 0.5 ml of N,N-Dimethylformamide was next added to the mixture, and the resulting golden yellow solution was stirred at RT for 3 h, during which LC-MS indicated completion of reaction. The reaction mixture was diluted with EtOAc and washed with water and brine, dried over MgSO₄, filtered, and concentrated in vacuo. CombiFlash purification (1% to 5% MeOH/ CH₂Cl₂) afforded the title compound (26) as a tan amorphous solid. MS (ES+): 306.2 (M+H)⁺.

Example 7

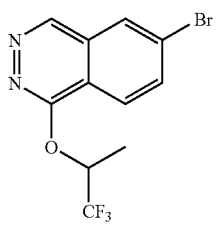

Synthesis of 6-Bromo-1-(1,1,1-trifluoropropan-2-yloxy)phthalazine

This compound was prepared according to the procedure described in Example 2b, but starting with 1,1,1-trifluoropropan-2-ol, sodium hydride and 6-bromo-1-chlorophthalazine. MS (ESI, pos. ion) m/z: 321.9 (M+1).

Examples 8

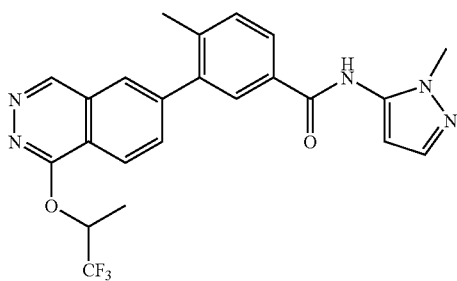

Synthesis of 4-Methyl-N-(1-methyl-1H-pyrazol-5-yl)-3-(1,1,1-trifluoropropan-2-yloxy)phthalazin-6-yl) benzamide (27)

The title compound (27) was prepared according to the procedure described in Example 2c, but starting with 6-bromo-1-(1,1,1-trifluoropropan-2-yloxy)phthalazine, tetrakis(triphenylphosphine)palladium and 4-methyl-N-(1-methyl-1H-pyrazol-5-yl)-3-(4,4,5,5-tetramethyl-1,3,2-dioxaborolan-2-yl)benzamid. MS (ESI, pos. ion) m/z: 456.1 (M+1).

Examples 9 and 10

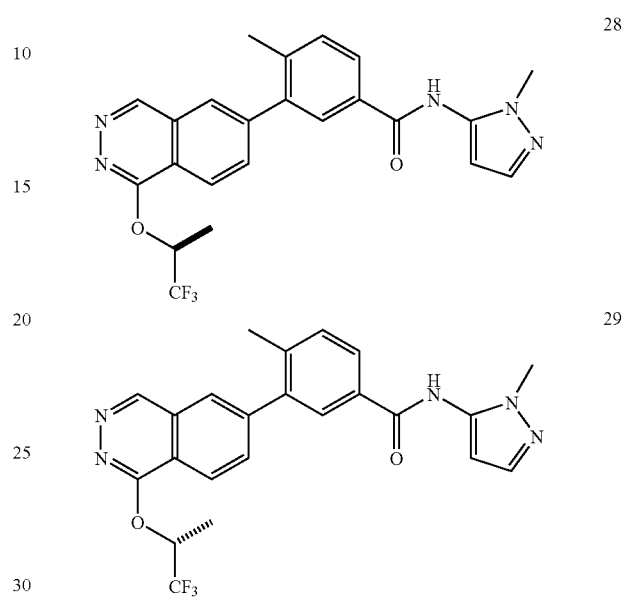

Synthesis of individual stereoisomers 28 and 29 of 4-Methyl-N-(1-methyl-1H-pyrazol-5-yl)-3-(1,1,1-trifluoropropan-2-yloxy)phthalazin-6-yl)benzamide (27)

4-Methyl-N-(1-methyl-1H-pyrazol-5-yl)-3-(1-(1,1,1-trifluoropropan-2-yloxy)phthalazin-6-yl)benzamide (27, 1.1 g) was subjected to the preparative SFC separation using a Chiralpak AD-H (150×4.6 mm, 5 □m) column with 75% liquid CO₂ and 25% isopropanol as the mobile phase to provide each of the following enantiomers: 4-methyl-N-(1-methyl-1H-pyrazol-5-yl)-3-(1-((S)-1,1,1-trifluoropropan-2-yloxy)phthalazin-6-yl)benzamide (28) and 4-methyl-N-(1-methyl-1H-pyrazol-5-yl)-3-(1-((R)-1,1,1-trifluoropropan-2-yloxy)phthalazin-6-yl)benzamide (29).

Example 11

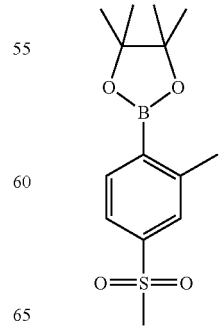

Synthesis of 4,4,5,5-tetramethyl-2-(2-methyl-4-(methylsulfonyl)phenyl)-1,3,2-dioxaborolane Step 1: A solution of 4-bromo-3-methylphenol (8.15 g, 43.6 mmol) in DMF (250 mL) at RT was treated with a suspension of NaH (1.25 g, 52.3 mmol) in 10 mL of DMF. After 15 minutes the solution was cooled to 0° C. and dimethylthiocarbamoyl chloride (8.08 g, 65.4 mmol) was added. The reaction mixture was warmed up to 80° C. and stirred for 45 minutes. After cooling to RT, the mixture was poured into water (1 L). The aqueous layer was extracted with EtOAc (3×200 mL). The combined organic layers were dried over anhydrous sodium sulfate, filtered and concentrated to give a yellow oil. The crude yellow oil material was purified by silica gel chromatography (5-50% EtOAc in hexanes) to afford 6.87 g of O-4-bromo-3-methylphenyl dimethylcarbamothioate as a clear, colorless oil. MS$^+$=276.0 (M+H)

Step 2: A solution of O-4-bromo-3-methylphenyl dimethylcarbamothioate (4.18 g, 15.2 mmol) in 120 mL of mineral oil was heated at 280° C. for 6 hours. After cooling to RT, the mineral oil was extracted with MeOH (2×300 mL) and the combined methanol layers were concentrated. The oil was purified by silica gel chromatography by eluting with hexanes and then flushing the column with dichloromethane to give S-4-bromo-3-methylphenyl dimethylcarbamothioate (3.23 g) as a clear oil. MS$^+$=276.0 (M+H)

Step 3: A mixture of S-4-bromo-3-methylphenyl dimethylcarbamothioate (4.56 g, 16.6 mmol) and potassium hydroxide (3.27 g, 58.2 mmol) in MeOH was heated at 90° C. for 1 hour. The mixture was cooled to RT and concentrated. The residue was redissolved in DCM and aqueous sodium bicarbonate (sat.) and the layers were separated. The organic layer was dried over sodium sulfate, filtered and concentrated. The crude material was purified by silica gel chromatography (100% hexanes) to afford 2.84 g of 4-bromo-3-methylbenzenethiol as a pale yellow oil.

Step 4: To a solution of 4-bromo-3-methylbenzenethiol (5.47 g, 26.9 mmol) in DMF (25 mL) was added NaH (0.743 g, 32.3 mmol) at RT. After 15 minutes at RT, the solution was cooled to 0° C. and iodomethane (2.02 ml, 32.3 mmol) was added. The cooling bath was removed and the mixture was allowed to warm up to RT. After 1 hour, water was added and the mixture was extracted with EtOAc (3×). The combined organic layers were dried over anhydrous sodium sulfate, filtered and concentrated to give 5.81 g of (4-bromo-3-methylphenyl)(methyl)sulfane as a pale yellow oil.

Step 5: To a heterogenous solution of (4-bromo-3-methylphenyl)(methyl)sulfane (2.17 g, 9.99 mmol) in 55 mL of 10/1 MeOH/water at 0° C. was added oxone (6.14 g, 9.99 mmol). The solution was allowed to warm up to RT and stirred overnight. Saturated sodium sulfite (aq.) was added and the mixture was extracted with DCM (3×). The combined organic layers were washed with water and NaCl (sat.), dried over sodium sulfate, filtered and concentrated to afford 2.30 g of 1-bromo-2-methyl-4-(methylsulfonyl)benzene 2.30 g as a white solid.

Step 6: A solution of 1-bromo-2-methyl-4-(methylsulfonyl)benzene (0.693 g, 2.78 mmol), bis(pinacolato)diboron (1.06 g, 4.17 mmol), dichloro[1,1'-bis(diphenylphosphino)ferrocene]palladium (II) dichloromethane adduct (0.204 g, 0.278 mmol) and potassium acetate (1.37 g, 13.9 mmol) in 14 mL of DMF was stirred and heated at 80° C. for 16 hours. Then the reaction mixture was cooled to RT and concentrated. The crude material was taken up in EtOAc and 2M HCl and filtered. The layers were separated and the aqueous layer was extracted with EtOAc and the combined organic layers were washed with NaCl (sat.), dried over sodium sulfate, filtered and concentrated to give 1.55 g of a brown oil. The crude material was purified by silica gel chromatography (3/1 Hex/EtOAc) to afford 480 mg of 4,4,5,5-tetramethyl-2-(2-methyl-4-(methylsulfonyl)phenyl)-1,3,2-dioxaborolane as a white solid. MS$^+$=297.1 (M+H)

Example 12

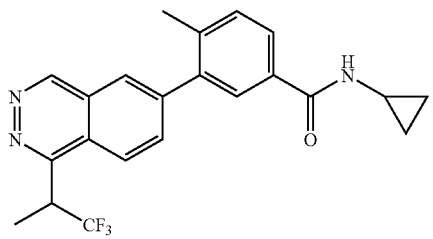

Synthesis of (+/−)N-Cyclopropyl-4-methyl-3-(1-(1,1,1-trifluoropropan-2-yl)phthalazin-6-yl)benzamide Step 1: Synthesis of Methyl 4-methyl-3-(1-(1,1,1-trifluoroprop-2-en-2-yl)phthalazin-6-yl)benzoate Methyl 3-(1-chlorophthalazin-6-yl)-4-methylbenzoate (563 mg, 1800 μmol), 4,4,6-trimethyl-2-(1,1,1-trifluoroprop-2-en-2-yl)-1,3,2-dioxaborinane (799 mg, 3600 μmol), tetrakis(triphenylphosphine)palladium (208 mg, 180 μmol), ethyl alcohol (200 proof; 2000 μl), 1,2-dimethoxyethane (8000 μl), and potassium carbonate (2M aqueous solution; 2700 μl, 5400 μmol) were combined in a sealed tube and heated at 80° C. for 2 h, during which LC-MS indicated 100% conversion. The cooled reaction was diluted with CH$_2$Cl$_2$ and washed with saturated aqueous NaHCO$_3$ solution and brine. The organic layer was dried (MgSO$_4$), filtered, and concentrated in vacuo. CombiFlash purification (20% to 80% EtOAc/Hexanes) afforded methyl 4-methyl-3-(1-(1,1,1-trifluoroprop-2-en-2-yl)phthalazin-6-yl)benzoate (210 mg, 31% yield) as a golden yellow foam. MS (ES+): 373.2 (M+H)$^+$.

Step 2: Synthesis of (+/−)Methyl 4-methyl-3-(1-(1,1,1-trifluoropropan-2-yl)phthalazin-6-yl)benzoate A solution of methyl 4-methyl-3-(1-(1,1,1-trifluoroprop-2-en-2-yl)phthalazin-6-yl)benzoate (200 mg, 537 μmol) in methanol (3000 μl) was added palladium (10 wt. % on activated carbon; 22.9 mg, 215 μmol) and hydrogenated (double-walled balloon pressure) at room temperature for 20 h, during which LC-MS indicated complete conversion. The reaction was filtered via a pad of Celite®, and the filtrate was concentrated in vacuo and purified by CombiFlash (20% to 80% EtOAc/Hexanes) to afford methyl 4-methyl-3-(1-(1,1,1-trifluoropropan-2-yl)phthalazin-6-yl)benzoate (91.1 mg, 45.3% yield) as a golden yellow foam. MS (ES+): 375.2 (M+H)$^+$.

Step 3: Synthesis of (+/−)4-Methyl-3-(1-(1,1,1-trifluoropropan-2-yl)phthalazin-6-yl)benzoic acid A solution of methyl 4-methyl-3-(1-(1,1,1-trifluoropropan-2-yl)phthalazin-6-yl)benzoate (91 mg, 243 μmol) in THF (1200 μl) and methanol (600 μl) was added NAOH (1N aqueous solution; 1215 μl, 1215 μmol) and stirred at 50° C. for 2 h, during which LC-MS indicated completion of reaction. After concentrating in vacuo, the slurry was diluted with water and the pH was adjusted with 10% aqueous HCl solution to ~7, resulting in the precipitation of 4-methyl-3-(1-(1,1,1-trifluoropropan-2-yl)phthalazin-6-yl)benzoic acid (86 mg, 98% yield) as a yellow solid. MS (ES+): 361.2 (M+H)$^+$.

Step 4: Synthesis of (+/−) N-Cyclopropyl-4-methyl-3-(1-(1,1,1-trifluoropropan-2-yl)phthalazin-6-yl) benzamide A solution of 4-methyl-3-(1-(1,1,1-trifluoropropan-2-yl)phthalazin-6-yl)benzoic acid (86 mg, 239 μmol) in N,N-dimethylformamide (1000 μl) were added HATU (136 mg, 358 μmol) and cyclopropylamine (8 μl, 2387 μmol). The resulting mixture was stirred at RT for 20 h, during which LC-MS indicated conversion to the desired product. The reaction was diluted with EtOAc and washed with water and brine. The organic layer was dried (MgSO$_4$), filtered, and concentrated in vacuo. Preparative HPLC purification (Shimadzu) afforded the title compound as a white amorphous solid. MS (ES+): 400.4 (M+H)$^+$.

The following Examples in Table I will further assist in understanding the scope of the invention. However, the following list of compounds is not intended in any manner to limit the scope of the invention. Such compounds are merely exemplary of the present invention. Each compound was named according to that naming convention, which is generally associated with ISIS and/or ChemDraw software. The mass spectral data is recorded M+H$^+$, which is the positive ion as measured by an electrospray ionization method, and the method by which each compound was made is in accordance with those methods A-E of Examples 2-6.

TABLE 1

| Example No | Compound Name | (MS(M + H+) | Method |
|---|---|---|---|
| 13 | N-3-isoxazolyl-4-methyl-3-(1-((1-methylethyl)amino)-6-phthalazinyl)benzamide | 388.2 | B |
| 14 | N-3-isoxazolyl-4-methyl-3-(1-((1-methylethyl)oxy)-6-phthalazinyl)benzamide | 389.2 | B |
| 15 | 4-methyl-3-(1-((3S)-3-methyl-4-morpholinyl)-6-phthalazinyl)-N-(1-methyl-1H-pyrazol-5-yl)benzamide | 443 | B |
| 16 | N-(1-ethyl-1H-pyrazol-5-yl)-4-methyl-3-(1-(3S)-3-methyl-4-morpholinyl)-6-phthalazinyl)benzamide | 457 | B |
| 17 | 4-methyl-3-(1-((1-methylethyl)amino)-6-phthalazinyl)-N-(1-methyl-1H-pyrazol-5-yl)benzamide | 401.1 | B |
| 18 | 4-methyl-3-(1-((1-methylethyl)amino)-6-phthalazinyl)-N-1,3-thiazol-2-ylbenzamide | 404 | B |
| 19 | N-(1-ethyl-1H-pyrazol-5-yl)-4-methyl-3-(1-((1-methylethyl)oxy)-6-phthalazinyl)benzamide | 416 | A |
| 20 | 4-methyl-3-(1-((1-methylethyl)oxy)-6-phthalazinyl)-N-(1-methyl-1H-pyrazol-5-yl)benzamide | 402 | A |
| 21 | N-cyclopropyl-3-(1-(ethyloxy)-6-phthalazinyl)-4-methylbenzamide | 348.2 | A |
| 22 | 4-chloro-N-(1-methylethyl)-3-(1-((1-methylethyl)amino)-6-phthalazinyl)benzamide | 383.2 | C |
| 23 | 4-chloro-N-cyclopropyl-3-(1-((1-methylethyl)amino)-6-phthalazinyl)benzamide | 381.2 | C |
| 24 | 4-methyl-3-(1-((1-methylethyl)amino)-6-phthalazinyl)-N-5-pyrimidinylbenzamide | 399.2 | B |
| 25 | 4-chloro-3-(1-((1-methylethyl)oxy)-6-phthalazinyl)benzamide | 342.1 | C |
| 26 | 4-chloro-N-(1-methylethyl)3-(1-((1-methylethyl)oxy)-6-phthalazinyl)benzamide | 384.2 | C |
| 27 | 4-methyl-N-(1-methylethyl)-3-(1-((2,2,2-trifluoro-1-methylethyl)oxy)-6-phthalazinyl)benzamide | 418.1 | A |
| 28 | 4-methyl-N-(1-methylethyl)-3-(1-(2-methylpropyl)-6-phthalazinyl)benzamide | 362.3 | E |
| 29 | 4-methyl-3-(1-((1-methylethyl)amino)-6-phthalazinyl)-N-(2,2,2-trifluoroethyl)benzamide | 403.3 | B |
| 30 | 4-methyl-N-(1-methylethyl)-3-(1-(2-methylphenyl)-6-phthalazinyl)benzamide | 396.2 | D |
| 31 | N-cyclopropyl-4-methyl-3-(1-((2,2,2-trifluoro-1-methylethyl)oxy)-6-phthalazinyl)benzamide | 416.1 | A |
| 32 | 3-(1-((2R)-2-(1,1-dimethylethyl)-1-pyrrolidinyl)-6-phthalazinyl)-4-methyl-N-(1-methylethyl)benzamide | 431.3 | B |

TABLE 1-continued

| Example No | Compound Name | (MS(M + H+) | Method |
|---|---|---|---|
| 33 | 3-(1-((2S)-2-(1,1-dimethylethyl)-1-pyrrolidinyl)-6-phthalazinyl)-4-methyl-N-(1-methylethyl)benzamide | 431.3 | B |
| 34 | 3-(1-((2R)-2-(1,1-dimethylethyl)-1-pyrrolidinyl)-6-phthalazinyl)-4-methylbenzamide | 389.2 | B |
| 35 | 3-(1-((2S)-2-(1,1-dimethylethyl)-1-pyrrolidinyl)-6-phthalazinyl)-4-methylbenzamide | 389.2 | B |
| 36 | 4-methyl-N-(1-methylethyl)-3-(1-((2S)-2-methyl-1-pyrrolidinyl)-6-phthalazinyl)benzamide | 389.2 | B |
| 37 | 4-methyl-N-(1-methylethyl)-3-(1-((2R)-2-methyl-1-pyrrolidinyl)-6-phthalazinyl)benzamide | 389.2 | B |
| 38 | 4-methyl-N-(4-methyl-1,3-oxazol-2-yl)-3-(1-((2,2,2-trifluoro-1-methylethyl)oxy)-6-phthalazinyl)benzamide | 457.1 | A |
| 39 | 4-methyl-N-(1-methylethyl)-3-(1-(1-methylethyl)-6-phthalazinyl)benzamide | 348.3 | E |
| 40 | 4-methyl-N-(1-methylethyl)-3-(1-(((1S)-2,2,2-trifluoro-1-methylethyl)oxy)-6-phthalazinyl)benzamide | 418.1 | A |
| 41 | 4-methyl-N-(1-methylethyl)-3-(1-(((1R)-2,2,2-trifluoro-1-methylethyl)oxy)-6-phthalazinyl)benzamide | 418.1 | A |
| 42 | 4-methyl-3-(1-(((1S)-2,2,2-trifluoro-1-methylethyl)oxy)-6-phthalazinyl)benzamide | 376.2 | A |
| 43 | 4-methyl-3-(1-(((1R)-2,2,2-trifluoro-1-methylethyl)oxy)-6-phthalazinyl)benzamide | 376.2 | A |
| 44 | N-(1,1-dimethylethyl)-4-methyl-3-(1-(((1S)-2,2,2-trifluoro-1-methylethyl)oxy)-6-phthalazinyl)benzamide | 432.4 | A |
| 45 | 4-methyl-N-(1-methyl-1H-pyrazol-3-yl)-3-(1-(((1R)-2,2,2-trifluoro-1-methylethyl)oxy)-6-phthalazinyl)benzamide | 456 | A |
| 46 | 4-methyl-3-(1-((2S)-2-(trifluoromethyl)-1-pyrrolidinyl)-6-phthalazinyl)benzamide | 401.1 | B |
| 47 | 4-methyl-N-(1-methylcyclopropyl)-3-(1-((1-methylethyl)amino)-6-phthalazinyl)benzamide | 375.2 | A |
| 48 | 3-(1-((2-fluoro-1-(fluoromethyl)ethyl)oxy)-6-phthalazinyl)-4-methyl-N-(1-methyl-1H-pyrazol-5-yl)benzamide | 438.1 | A |
| 49 | N-cyclopropyl-3-(1-((2-fluoro-1-(fluoromethyl)ethyl)oxy)-6-phthalazinyl)-4-methylbenzamide | 398.1 | A |
| 50 | 3-(1-hydroxy-6-phthalazinyl)-4-methyl-N-(1-methyl-1H-pyrazol-5-yl)benzamide | 360 | D |
| 51 | 4-methyl-3-(1-(1-methylpropyl)-6-phthalazinyl)benzamide | 320.2 | E |
| 52 | 4-methyl-3-(1-(1-methylethyl)-6-phthalazinyl)-N-(2,2,2-trifluoroethyl)benzamide | 388.2 | E |
| 53 | N-cyclopropyl-4-methyl-3-(1-(((1S)-2,2,2-trifluoro-1-methylethyl)oxy)-6-phthalazinyl)benzamide | 416.1 | A |
| 54 | N-cyclopropyl-4-methyl-3-(1-(((1R)-2,2,2-trifluoro-1-methylethyl)oxy)-6-phthalazinyl)benzamide | 416.1 | A |
| 55 | 3-(1-chloro-6-phthalazinyl)-4-methyl-N-(1-methyl-1H-pyrazol-5-yl)benzamide | 378 | D |
| 56 | 3-(1-(4-fluorophenyl)-6-phthalazinyl)-4-methyl-N-(1-methyl-1H-pyrazol-5-yl)benzamide | 438 | D |
| 57 | 4-methyl-3-(1-(1-methylethyl)-6-phthalazinyl)benzamide | 306.2 | E |
| 58 | 4-methyl-3-(1-(2-methylphenyl)-6-phthalazinyl)-N-(2,2,2-trifluoroethyl)benzamide | 436.2 | D |
| 59 | 4-methyl-N-(1-methylcyclopropyl)-3-(1-(((1S)-2,2,2-trifluoro-1-methylethyl)oxy)-6-phthalazinyl)benzamide | 430.2 | A |

TABLE 1-continued

| Example No | Compound Name | (MS(M + H+) | Method |
|---|---|---|---|
| 60 | 4-methyl-N-(1-methylcyclopropyl)-3-(1-(((1R)-2,2,2-trifluoro-1-methylethyl)oxy)-6-phthalazinyl)benzamide | 430.2 | A |
| 61 | 3-(1-(1,1-dimethylethyl)-6-phthalazinyl)-4-methyl-N-(1-methylethyl)benzamide | 362.2 | E |
| 62 | 3-(1-(4-fluoro-2-methylphenyl)-6-phthalazinyl)-4-methyl-N-(1-methyl-1H-pyrazol-3-yl)benzamide | 452 | D |
| 63 | 4-methyl-3-(1-(2-methylphenyl)-6-phthalazinyl)-N-(1-methyl-1H-pyrazol-3-yl)benzamide | 434 | D |
| 64 | 3-(1-(4-fluoro-2-methylphenyl)-6-phthalazinyl)-4-methyl-N-(2,2,2-trifluoroethyl)benzamide | 454.1 | D |
| 65 | 3-(1-(4-fluoro-2-methylphenyl)-6-phthalazinyl)-4-methyl-N-(1-methylcyclopropyl)benzamide | 426.2 | D |
| 66 | 4-methyl-N-(1-methylcyclopropyl)-3-(1-((2S)-2-methyl-1-pyrrolidinyl)-6-phthalazinyl)benzamide | 401.2 | B |
| 67 | 4-methyl-N-(1-methylcyclopropyl)-3-(1-(((1S)-2,2,2-trifluoro-1-methylethyl)oxy)-6-phthalazinyl)benzamide | 430.3 | A |
| 68 | 4-methyl-N-(1-methylcyclopropyl)-3-(1-(((1R)-2,2,2-trifluoro-1-methylethyl)oxy)-6-phthalazinyl)benzamide | 430.2 | A |
| 69 | 4-methyl-N-(1-methylcyclopropyl)-3-(1-(1-methylethyl)-6-phthalazinyl)benzamide | 360.2 | E |
| 70 | N-cyclopropyl-3-(1-(1,1-dimethylethyl)-6-phthalazinyl)-4-methylbenzamide | 360.3 | E |
| 71 | 4-methyl-N-(1-methyl-1H-pyrazol-3-yl)-3-(1-(((1R)-2,2,2-trifluoro-1-methylethyl)oxy)-6-phthalazinyl)benzamide | 456 | A |
| 72 | 4-methyl-N-(1-methyl-1H-pyrazol-3-yl)-3-(1-(((1S)-2,2,2-trifluoro-1-methylethyl)oxy)-6-phthalazinyl)benzamide | 456 | A |
| 73 | 4-methyl-N-(2,2,2-trifluoroethyl)-3-(1-(((1R)-2,2,2-trifluoro-1-methylethyl)oxy)-6-phthalazinyl)benzamide | 458.1 | A |
| 74 | 4-methyl-N-(2,2,2-trifluoroethyl)-3-(1-(((1S)-2,2,2-trifluoro-1-methylethyl)oxy)-6-phthalazinyl)benzamide | 458.1 | A |
| 75 | N-cyclopropyl-3-(1-(2,2-dimethylpropyl)-6-phthalazinyl)-4-methylbenzamide | 374.4 | E |
| 76 | 3-(1-(2,2-dimethylpropyl)-6-phthalazinyl)-4-methyl-N-(1-methylcyclopropyl)benzamide | 388.4 | E |
| 77 | 3-(1-(2,2-dimethylpropyl)-6-phthalazinyl)-4-methyl-N-(2,2,2-trifluoroethyl)benzamide | 416.4 | E |
| 78 | 4-methyl-N-(2,2,2-trifluoroethyl)-3-(1-(((1R)-2,2,2-trifluoro-1-methylethyl)oxy)-6-phthalazinyl)benzamide | 458.1 | A |
| 79 | 4-methyl-N-(2,2,2-trifluoroethyl)-3-(1-(((1S)-2,2,2-trifluoro-1-methylethyl)oxy)-6-phthalazinyl)benzamide | 458.1 | A |
| 80 | 3-(1-(1,1-dimethylethyl)-6-phthalazinyl)-4-methyl-N-(1-methyl-1H-pyrazol-5-yl)benzamide | 400.4 | E |
| 81 | 3-(1-(1,1-dimethylethyl)-6-phthalazinyl)-4-methyl-N-(2,2,2-trifluoroethyl)benzamide | 402.4 | E |
| 82 | 4-methyl-N-1,3,4-thiadiazol-2-yl-3-(1-(((1R)-2,2,2-trifluoro-1-methylethyl)oxy)-6-phthalazinyl)benzamide | 460 | A |
| 83 | 4-methyl-N-1,3,4-thiadiazol-2-yl-3-(1-(((1S)-2,2,2-trifluoro-1-methylethyl)oxy)-6-phthalazinyl)benzamide | 460 | A |
| 84 | 4-methyl-N-1,3-thiazol-2-yl-3-(1-(((1S)-2,2,2-trifluoro-1-methylethyl)oxy)-6-phthalazinyl)benzamide | 459 | A |
| 85 | 4-methyl-N-1,3-thiazol-2-yl-3-(1-(((1R)-2,2,2-trifluoro-1-methylethyl)oxy)-6-phthalazinyl)benzamide | 459 | A |
| 86 | 4-methyl-3-(1-(2-methyl-4-(methylsulfonyl)phenyl)-6-phthalazinyl)- | 512.2 | D |

TABLE 1-continued

| Example No | Compound Name | (MS(M + H+) | Method |
|---|---|---|---|
| 87 | N-(1-methyl-1H-pyrazol-5-yl)benzamide 3-(1-(1,1-dimethylethyl)-6-phthalazinyl)-4-methyl-N-(1-methylcyclopropyl)benzamide | 374.4 | E |
| 88 | N-cyclopropyl-4-methyl-3-(1-((1S)-2,2,2-trifluoro-1-methylethyl)-6-phthalazinyl)benzamide | 400.4 | D |
| 89 | N-cyclopropyl-4-methyl-3 -(1-((1R)-2,2,2-trifluoro-1-methylethyl)-6-phthalazinyl)benzamide | 400.4 | D |
| 90 | N-cyclopropyl-4-methyl-3-(1-(1-(trifluoromethyl)ethenyl)-6-phthalazinyl)benzamide | 398.1 | D |
| 91 | 4-methyl-N-(1-methyl-1H-pyrazol-5-yl)-3-(1-(1-(trifluoromethyl)ethenyl)-6-phthalazinyl)benzamide | 438.2 | D |
| 92 | 4-methyl-N-(1-methyl-1H-pyrazol-5-yl)-3-(1-((1R)-2,2,2-trifluoro-1-methylethyl)-6-phthalazinyl)benzamide | 440.1 | D |
| 93 | 4-methyl-N-(1-methyl-1H-pyrazol-5-yl)-3-(1-((1S)-2,2,2-trifluoro-1-methylethyl)-6-phthalazinyl)benzamide | | |
| 94 | 4-methyl-N-(1-methyl-1H-pyrazol-5-yl)-3-(1-((1R)-2,2,2-trifluoro-1-methylethyl)-6-phthalazinyl)benzamide | 440.1 | E |
| 95 | 4-methyl-N-(1-methyl-1H-pyrazol-5-yl)-3-(1-((1S)-2,2,2-trifluoro-1-methylethyl)-6-phthalazinyl)benzamide | 440.1 | E |

The following compounds in Tables 2 and 3 are additional representative examples of Formula I, as provided by the present invention.

TABLE 2

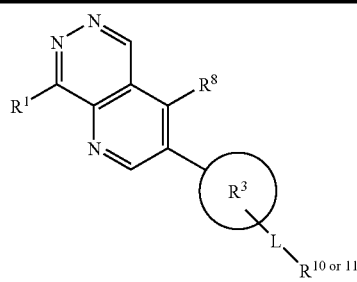

| Ex. No. | $R^1$ | $R^3$ | $R^5$ | L | $R^{10}$ or $R^{11}$ |
|---|---|---|---|---|---|
| 95 | 1-morpholinyl | 4-$CH_3$-phenyl | H | m-C(O)NH— | 5-pyrazolyl or 1,3,4-thiadiazol-2-yl |
| 96 | 1-piperazinyl | 4-$CH_3$-phenyl | H | m-C(O)NH— | 5-pyrazolyl or 1,3,4-thiadiazol-2-yl |
| 97 | 1-piperidinyl | phenyl | H | m-C(O)NH— | 3-pyrazolyl or 1,3,4-thiadiazol-2-yl |
| 98 | cyclohexyl-N— | 6-$CH_3$-phenyl | H | m-NHC(O)NH— | 3-pyrazolyl or 1,3,4-thiadiazol-2-yl |
| 99 | morpholine-$(CH_2)_2$—N— | 4-$OCH_3$-phenyl | H | m-C(O)NH— | 5-pyrazolyl or 1,3,4-thiadiazol-2-yl |
| 100 | $(CH_3)_2$N—$(CH_2)_2$—N— | 4-$OCH_3$-phenyl | H | m-C(O)NH— | 5-pyrazolyl or 1,3,4-thiadiazol-2-yl |
| 101 | $(C_2H_5)_2$N—$(CH_2)_2$—N— | phenyl | H | m-NHC(O)NH— | 3-pyrazolyl or 1,3,4-thiadiazol-2-yl |
| 102 | 3-OH-1-pyrrolidinyl | 6-$OCH_3$—phenyl | H | m-C(O)NH— | 5-pyrazolyl or 1,3,4-thiadiazol-2-yl |
| 103 | 3-amino-1-pyrrolidinyl | 6-$OCH_3$-phenyl | H | m-C(O)NH— | 5-pyrazolyl or 1,3,4-thiadiazol-2-yl |
| 104 | 4-amino-1-piperidinyl | 4-F-phenyl | H | m-C(O)NH— | 5-pyrazolyl or 1,3,4-thiadiazol-2-yl |
| 105 | 3-amino-1-piperidinyl | 4-Cl-phenyl | H | m-C(O)NH— | 3-pyrazolyl or 1,3,4-thiadiazol-2-yl |

TABLE 2-continued

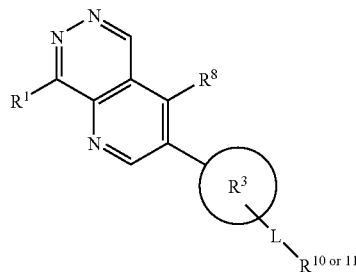

| Ex. No. | R$^1$ | R$^3$ | R$^5$ | L | R$^{10}$ or R$^{11}$ |
|---|---|---|---|---|---|
| 106 | 4N—CH$_3$-1-piperizinyl | 4-F-phenyl | H | m-C(O)NH— | 5-pyrazolyl or 1,3,4-thiadiazol-2-yl |
| 107 | 2-Cl-phenyl | phenyl | H | m-NHC(O)— | 5-pyrazolyl or 1,3,4-thiadiazol-2-yl |
| 108 | 2-CH$_3$-phenyl | 6-F-phenyl | H | m-NHC(O)NH— | 5-pyrazolyl or 1,3,4-thiadiazol-2-yl 1 |
| 109 | 4-CH$_3$-phenyl | 2-thiophene | H | m-C(O)NH— | 5-pyrazolyl or 1,3,4-thiadiazol-2-yl |
| 110 | 4-Cl-phenyl | 3-thiophene | H | m-C(O)NH— | 5-pyrazolyl or 1,3,4-thiadiazol-2-yl |
| 111 | 3-Cl-phenyl | 2-pyridine | H | m-C(O)NH— | 5-pyrazolyl or 1,3,4-thiadiazol-2-yl |
| 112 | 2,2,2-trifluoro-1-methyl-ethoxyl | 3-pyridine | H | m-C(O)NH— | 5-pyrazolyl or 1,3,4-thiadiazol-2-yl |
| 113 | Ethoxyl | 6-CH$_3$-phenyl | H | m-NHC(O)NH— | 5-pyrazolyl or 1,3,4-thiadiazol-2-yl |
| 114 | methoxyl | 4-CH$_3$-phenyl | H | m-NHC(O)— | 5-pyrazolyl or 1,3,4-thiadiazol-2-yl |
| 115 | isopropoxyl | 4-Cl-phenyl | H | m-C(O)NH— | 5-pyrazolyl or 1,3,4-thiadiazol-2-yl |
| 116 | 2-t-butyl-pyrrolidinyl | 4-CH$_3$-phenyl | H | m-C(O)NH— | 5-pyrazolyl or 1,3,4-thiadiazol-2-yl |
| 117 | 2-methylpyrrolidinyl | 4-CH$_3$-phenyl | H | m-C(O)NH— | 3-pyrazolyl or 1,3,4-thiadiazol-2-yl |
| 118 | 2-isopropyl-pyrrolidinyl | phenyl | H | m-C(O)NH— | 5-pyrazolyl or 1,3,4-thiadiazol-2-yl |
| 119 | 2-ethylpyrrolidinyl | 6-CH$_3$-phenyl | H | m-C(O)NH— | 5-pyrazolyl or 1,3,4-thiadiazol-2-yl |
| 120 | 2,2,2-trifluoro-1-methyl-ethoxyl | 4-OCH$_3$-phenyl | H | m-NHC(O)NH— | 5-pyrazolyl or 1,3,4-thiadiazol-2-yl |
| 121 | Ethoxyl | 4-OCH$_3$—phenyl | H | m-C(O)NH— | 3-pyrazolyl or 1,3,4-thiadiazol-2-yl |
| 122 | methoxyl | phenyl | H | m-C(O)NH— | 5-pyrazolyl or 1,3,4-thiadiazol-2-yl |
| 123 | 2-t-butyl-pyrrolidinyl | 6-OCH$_3$-phenyl | H | m-NHC(O)— | 3-pyrazolyl or 1,3,4-thiadiazol-2-yl |
| 124 | 2-methylpyrrolidinyl | 6-OCH$_3$—phenyl | H | m-C(O)NH— | 5-pyrazolyl or 1,3,4-thiadiazol-2-yl |
| 125 | 2-isopropyl-pyrrolidinyl | 4-F-phenyl | H | m-C(O)NH— | 5-pyrazolyl or 1,3,4-thiadiazol-2-yl |
| 126 | 2,2,2-trifluoro-1-methyl-ethoxyl | 6-F-phenyl | H | m-C(O)NH— | ethyl |
| 127 | Ethoxyl | 4-F-phenyl | H | m-C(O)NH— | cyclopropyl |
| 128 | methoxyl | phenyl | H | m-C(O)NH— | cyclopropyl |
| 129 | isopropoxyl | 6-F-phenyl | H | m-C(O)NH— | ethyl |
| 130 | 2,2,2-trifluoro-1-methyl-ethoxyl | 2-thiophene | H | m-C(O)NH— | ethyl |
| 131 | Ethoxyl | 3-thiophene | H | m-C(O)NH— | isopropyl |
| 132 | methoxyl | 2-pyridine | H | m-C(O)NH— | ethyl |
| 133 | isopropoxyl | 3-pyridine | H | m-C(O)NH— | cyclopropyl |
| 134 | 2,2,2-trifluoro-1-methyl-ethoxyl | 4-CH$_3$-phenyl | H | m-C(O)NH— | cyclopropyl |
| 135 | Ethoxyl | 4-CH$_3$-phenyl | H | m-C(O)NH— | cyclopropyl |
| 136 | methoxyl | phenyl | H | m-C(O)NH— | ethyl |
| 137 | isopropoxyl | 6-CH$_3$-phenyl | H | m-C(O)NH— | propyl |
| 138 | 2,2,2-trifluoro-1-methyl-ethoxyl | 4-CH$_3$-phenyl | H | m-C(O)NH— | isopropyl |
| 139 | Ethoxyl | phenyl | H | m-C(O)NH— | propyl |
| 140 | methoxyl | 6-CH$_3$-phenyl | H | m-C(O)NH— | isopropyl |

TABLE 2-continued

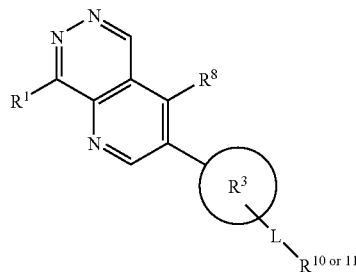

| Ex. No. | R¹ | R³ | R⁵ | L | R¹⁰ or R¹¹ |
|---|---|---|---|---|---|
| 141 | isopropoxyl | 4-OCH₃-phenyl | H | m-C(O)NH— | propyl |
| 142 | 2-t-butyl-pyrrolidinyl | 4-OCH₃-phenyl | H | m-C(O)NH— | propyl |
| 143 | 2-methylpyrrolidinyl | phenyl | H | m-C(O)NH— | cyclopropyl |
| 144 | 2-isopropyl-pyrrolidinyl | 6-OCH₃-phenyl | H | m-C(O)NH— | cyclopropyl |
| 145 | 2-ethylpyrrolidinyl | 6-OCH₃-phenyl | H | m-C(O)NH— | cyclopropyl |
| 146 | 2-t-butyl-pyrrolidinyl | 4-F-phenyl | H | m-C(O)NH— | propyl |
| 147 | 2-methylpyrrolidinyl | 6-Cl-phenyl | H | m-C(O)NH— | propyl |
| 148 | 2-isopropyl-pyrrolidinyl | 4-Cl-phenyl | H | m-C(O)NH— | propyl |
| 149 | 2-ethylpyrrolidinyl | phenyl | H | m-C(O)NH— | propyl |
| 150 | 2-t-butyl-pyrrolidinyl | 6-F-phenyl | H | m-C(O)NH— | pcyclopropyl |
| 151 | 2-methylpyrrolidinyl | 2-thiophene | H | m-C(O)NH— | propyl |
| 152 | 2-isopropyl-pyrrolidinyl | 3-thiophene | H | m-C(O)NH— | propyl |
| 153 | 2-ethylpyrrolidinyl | 2-pyridine | H | m-C(O)NH— | propyl |
| 154 | 2-t-butyl-pyrrolidinyl | 3-pyridine | H | m-C(O)NH— | propyl |
| 155 | 2-methylpyrrolidinyl | 6-CH₃-phenyl | H | m-C(O)NH— | cyclopropyl |
| 156 | 2-isopropyl-pyrrolidinyl | 4-CH₃-phenyl | H | m-C(O)NH— | cyclopropyl |
| 157 | 2-ethylpyrrolidinyl | phenyl | H | m-C(O)NH— | cyclopropyl |
| 158 | 2,2,2-trifluoro-1-methyl-ethoxy | H | CH₃ | m-C(O)NH— | methylcyclopropyl |

TABLE 3

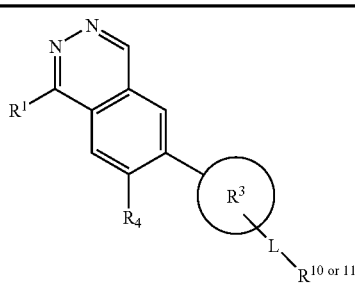

| Ex. No. | R¹ | R³ | R⁴ | L | R¹⁰ or R¹¹ |
|---|---|---|---|---|---|
| 159 | 2,2,2-trifluoro-1-methyl-ethoxyl | 4-CH₃-phenyl | H | m-C(O)NH— | 5-pyrazolyl or 1,3,4-thiadiazol-2-yl |
| 160 | Ethoxyl | 4-Cl-phenyl | H | m-C(O)NH— | 5-pyrazolyl or 1,3,4-thiadiazol-2-yl |
| 161 | 2,2,2-trifluoro-1-methyl-ethyl | 6-OCH₃-phenyl | H | m-C(O)NH— | 3-pyrazolyl or 1,3,4-thiadiazol-2-yl |
| 162 | isopropoxyl | 6-OCH₃-phenyl | H | m-C(O)NH— | 3-pyrazolyl or 1,3,4-thiadiazol-2-yl |
| 163 | 2-t-butyl-pyrrolidinyl | 4-F-phenyl | H | m-C(O)NH— | 5-pyrazolyl or 1,3,4-thiadiazol-2-yl |
| 164 | 2-methylpyrrolidinyl | 4-Cl-phenyl | H | m-NHC(O) | 5-pyrazolyl or 1,3,4-thiadiazol-2-yl |
| 165 | 2-isopropyl-pyrrolidinyl | 4-F-phenyl | H | m-NHC(O)NH— | 3-pyrazolyl or 1,3,4-thiadiazol-2-yl |
| 166 | 2-ethylpyrrolidinyl | phenyl | H | m-C(O)NH— | 5-pyrazolyl or 1,3,4-thiadiazol-2-yl |

TABLE 3-continued

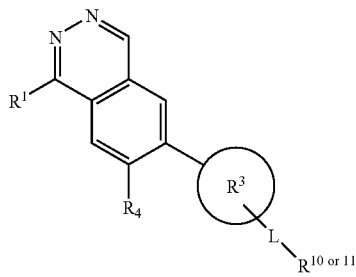

| Ex. No. | R¹ | R³ | R⁴ | L | R¹⁰ or R¹¹ |
|---|---|---|---|---|---|
| 167 | 2,2,2-trifluoro-1-methyl-ethoxyl | 6-F-phenyl | H | m-C(O)NH— | 5-pyrazolyl or 1,3,4-thiadiazol-2-yl |
| 168 | Ethoxyl | 2-thiophene | H | m-C(O)NH— | 3-pyrazolyl or 1,3,4-thiadiazol-2-yl |
| 169 | 2,2,2-trifluoro-1-methyl-ethyl | 3-thiophene | H | m-C(O)NH— | 3-pyrazolyl or 1,3,4-thiadiazol-2-yl |
| 170 | 2-t-butyl-pyrrolidinyl | 2-pyridine | H | m-NHC(O)NH— | 5-pyrazolyl or 1,3,4-thiadiazol-2-yl |
| 171 | 2-methylpyrrolidinyl | 3-pyridine | H | m-NHC(O)— | 5-pyrazolyl or 1,3,4-thiadiazol-2-yl |
| 172 | 2-isopropyl-pyrrolidinyl | 6-CH₃-phenyl | H | m-C(O)NH— | 3-pyrazolyl or 1,3,4-thiadiazol-2-yl |
| 173 | 2,2,2-trifluoro-1-methyl-ethoxyl | 4-CH₃-phenyl | H | m-C(O)NH— | 5-pyrazolyl or 1,3,4-thiadiazol-2-yl |
| 174 | Ethoxyl | 4-Cl-phenyl | H | m-C(O)NH— | 5-pyrazolyl or 1,3,4-thiadiazol-2-yl |
| 175 | 2,2,2-trifluoro-1-methyl-ethyl | 4-CH₃-phenyl | H | m-C(O)NH— | 3-pyrazolyl or 1,3,4-thiadiazol-2-yl |
| 176 | isopropoxyl | 4-CH₃-phenyl | H | m-C(O)NH— | 3-pyrazolyl or 1,3,4-thiadiazol-2-yl |
| 177 | 2,2,2-trifluoro-1-methyl-ethoxyl | phenyl | H | m-NHC(O)NH— | 5-pyrazolyl or 1,3,4-thiadiazol-2-yl |
| 178 | Ethoxyl | 6-CH₃-phenyl | H | m-C(O)NH— | 5-pyrazolyl or 1,3,4-thiadiazol-2-yl |
| 179 | methoxyl | 4-OCH₃-phenyl | H | m-C(O)NH— | 3-pyrazolyl or 1,3,4-thiadiazol-2-yl |
| 180 | isopropoxyl | 4-OCH₃-phenyl | H | m-NHC(O)— | 3-pyrazolyl or 1,3,4-thiadiazol-2-yl |
| 181 | 2,2,2-trifluoro-1-methyl-ethoxyl | phenyl | H | m-C(O)NH— | 5-pyrazolyl or 1,3,4-thiadiazol-2-yl |
| 182 | Ethoxyl | 6-OCH₃-phenyl | H | m-C(O)NH— | 5-pyrazolyl or 1,3,4-thiadiazol-2-yl |
| 183 | 2,2,2-trifluoro-1-methyl-ethyl | 6-OCH₃-phenyl | H | m-C(O)NH— | 3-pyrazolyl or 1,3,4-thiadiazol-2-yl |
| 184 | isopropoxyl | 4-F-phenyl | H | m-C(O)NH— | ethyl |
| 185 | 2,2,2-trifluoro-1-methyl-ethoxyl | 6-F-phenyl | H | m-C(O)NH— | tetrahydropyrrolyl |
| 186 | Ethoxyl | 4-F-phenyl | H | m-C(O)NH— | isopropyl |
| 187 | methoxyl | phenyl | H | m-C(O)NH— | methyl |
| 188 | isopropoxyl | 6-F-phenyl | H | m-C(O)NH— | butyl |
| 189 | 2-t-butyl-pyrrolidinyl | 2-thiophene | H | m-C(O)NH— | pentyl |
| 190 | 2-methylpyrrolidinyl | 3-thiophene | H | m-C(O)NH— | tetrahydropyrrolyl |
| 191 | 2,2,2-trifluoro-1-methyl-ethyl | 2-pyridine | H | m-C(O)NH— | ethyl |
| 192 | 2-ethylpyrrolidinyl | 3-pyridine | H | m-C(O)NH— | tetrahydropyrrolyl |
| 193 | 2,2,2-trifluoro-1-methyl-ethyl | 4-CH₃-phenyl | H | m-C(O)NH— | isopropyl |
| 194 | 2-methylpyrrolidinyl | 4-CH₃-phenyl | H | m-C(O)NH— | methyl |
| 195 | 2-isopropyl-pyrrolidinyl | phenyl | H | m-C(O)NH— | butyl |
| 196 | 2-ethylpyrrolidinyl | 6-CH₃-phenyl | H | m-C(O)NH— | ethyl |
| 197 | 2-t-butyl-pyrrolidinyl | 4-CH₃-phenyl | H | m-NHC(O)— | isopropyl |
| 198 | 2-methylpyrrolidinyl | phenyl | H | m-NHC(O)NH— | methyl |
| 199 | 2-isopropyl-pyrrolidinyl | 6-CH₃-phenyl | H | m-C(O)NH— | ethyl |

TABLE 3-continued

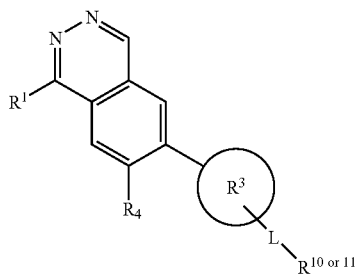

| Ex. No. | R¹ | R³ | R⁴ | L | R¹⁰ or R¹¹ |
|---|---|---|---|---|---|
| 200 | 2-ethylpyrrolidinyl | 4-OCH₃-phenyl | H | m-C(O)NH— | ethyl |
| 201 | 2-t-butyl-pyrrolidinyl | 4-OCH₃-phenyl | H | m-C(O)NH— | tetrahydropyrrolyl |
| 202 | 2,2,2-trifluoro-1-methyl-ethyl | phenyl | H | m-C(O)NH— | propyl |
| 203 | 2-isopropyl-pyrrolidinyl | 6-OCH₃-phenyl | H | m-NHC(O)NH— | isopropyl |
| 204 | 2-ethylpyrrolidinyl | 6-OCH₃-phenyl | H | m-NHC(O)— | methyl |
| 205 | 2,2,2-trifluoro-1-methyl-ethoxy | 4-F-phenyl | H | m-C(O)NH— | butyl |
| 206 | 2,2,2-trifluoro-1-methyl-ethoxyl | 6-Cl-phenyl | H | m-C(O)NH— | isopropyl |
| 207 | Ethoxyl | 4-Cl-phenyl | H | m-C(O)NH— | propyl |
| 208 | methoxyl | phenyl | H | m-C(O)NH— | propyl |
| 209 | isopropoxyl | 6-F-phenyl | H | m-C(O)NH— | isopropyl |
| 210 | 2-t-butyl-pyrrolidinyl | 2-thiophene | H | m-NHC(O)NH— | methyl |
| 211 | 2-methylpyrrolidinyl | 3-thiophene | H | m-C(O)NH— | butyl |
| 212 | 2-isopropyl-pyrrolidinyl | 2-pyridine | H | m-C(O)NH— | propyl |
| 213 | 2-ethylpyrrolidinyl | 3-pyridine | H | m-NHC(O)— | 3-pyrazolyl or 1,3,4-thiadiazol-2-yl |
| 214 | 2,2,2-trifluoro-1-methyl-ethoxyl | 6-CH₃-phenyl | H | m-C(O)NH— | 3-pyrazolyl or 1,3,4-thiadiazol-2-yl |
| 215 | Ethoxyl | 4-CH₃-phenyl | H | m-C(O)NH— | 5-pyrazolyl or 1,3,4-thiadiazol-2-yl |
| 216 | 2,2,2-trifluoro-1-methyl-ethyl | phenyl | H | m-C(O)NH— | 5-pyrazolyl or 1,3,4-thiadiazol-2-yl |
| 217 | 2,2,2-trifluoro-1-methyl-ethyl | H | H | m-C(O)NH— | 3-pyrazolyl or 1,3,4-thiadiazol-2-yl |
| 218 | 2-methylpyrrolidinyl | 6-OCH₃-phenyl | H | m-C(O)NH— | 3-pyrazolyl or 1,3,4-thiadiazol-2-yl |
| 219 | 2-isopropyl-pyrrolidinyl | 6-OCH₃-phenyl | H | m-C(O)NH— | 3-pyrazolyl or 1,3,4-thiadiazol-2-yl |
| 220 | 2,2,2-trifluoro-1-methyl-ethoxyl | 4-F-phenyl | H | m-C(O)NH— | cyclopropyl |
| 221 | Ethoxyl | 4-Cl-phenyl | H | m-C(O)NH— | cyclopropyl |
| 222 | 2,2,2-trifluoro-1-methyl-ethyl | 4-F-phenyl | H | m-C(O)NH— | cyclopropyl |

Example 223 (Method F)

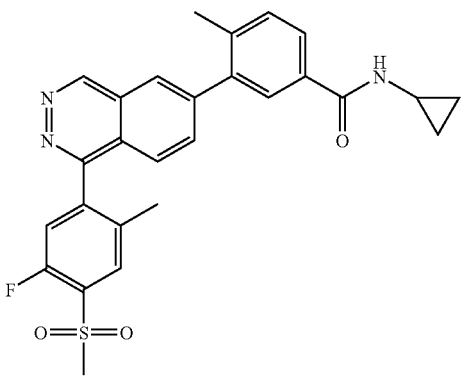

Synthesis of N-Cyclopropyl-3-(1-(5-fluoro-2-methyl-4-(methylsulfonyl)phenyl)phthalazin-6-yl)-4-methylbenzamide

Step 1: 4-Bromo-2-fluoro-5-methylphenol

A solution of 2-fluoro-5-methylphenol (8.66 mL, 79.28 mmol) in 250 mL of ACN at 0° C. was treated with NBS (14.82 g, 83.25 mmol). The mixture was stirred for 1 hr at 0° C. and then concentrated. The crude material was passed through a small column of silica gel and rinsed with DCM to give 16.14 g of a yellow solid. This material was further purified by silica gel column chromatography (5% EtOAc in hexanes) to afford 4-bromo-2-fluoro-5-methylphenol (13.76 g, 84.6% yield) as a white solid. MS (ESI, pos. ion) m/z: 205.9 (M+1).

Step 2: 4-Bromo-2-fluoro-5-methylbenzenethiol

A solution of 4-bromo-2-fluoro-5-methylphenol (13.76 g, 67.11 mmol) in 300 mL of DMF was treated with NaH (60% wt. dispersion in mineral oil, 1.85 g, 80.54 mmol) at RT. The solution was cooled to 0° C. and dimethylthiocarbamoyl chloride (12.44 g, 100.7 mmol) was added. The mixture was heated at 80° C. for 2 h. After cooling to RT, the mixture was poured into water and extracted with EtOAc (3×). The combined organic layers were dried over anhydrous sodium sulfate, filtered and concentrated to give 40 g of yellow oil. The yellow oil was loaded on a silica gel column (eluted with 0-25% EtOAc in hexanes) to afford O-4-bromo-2-fluoro-5-methylphenyl dimethylcarbamothioate (16.88 g, 86.1% yield) as a white solid.

To a solution of O-4-bromo-2-fluoro-5-methylphenyl dimethylcarbamothioate (12.20 g, 41.8 mmol) in 200 mL of MeOH was added potassium hydroxide (8.20 g, 146 mmol). The reaction mixture was heated to reflux for 1 h and then cooled to RT and concentrated. The residue was taken up in dichloromethane and aqueous sodium bicarbonate (sat.) and the layers were separated. The organic layer was dried over sodium sulfate, filtered and concentrated to give 9.44 g of an orange oil. The crude product was purified by silica gel chromatography to afford 4-bromo-2-fluoro-5-methylbenzenethiol (6.89 g, 74.6% yield) as a colorless oil.

Step 3: (4-Bromo-2-fluoro-5-methylphenyl)(methyl)sulfane

A solution of 4-bromo-2-fluoro-5-methylbenzenethiol (2.28 g, 10.3 mmol) in 25 mL of DMF at RT was treated with NaH (0.284 g, 12.4 mmol). After 15 minutes the solution was cooled to 0° C. and iodomethane (0.772 mL, 12.4 mmol) was added. The reaction mixture was allowed to warm up to RT and stirred overnight. The reaction mixture was poured into water and extracted with EtOAc (3×). The combined organic layers were dried over anhydrous sodium sulfate, filtered and concentrated to give the title compound (2.40 g, 99% yield) as an orange oil. The crude material was used in the next step without further purification.

Step 4: 1-Bromo-5-fluoro-2-methyl-4-(methylsulfonyl)benzene

A heterogenous solution of (4-bromo-2-fluoro-5-methylphenyl)(methyl)sulfane (0.592 g, 2.52 mmol) in 12 mL of 10/1/1 MeOH/chloroform/water at RT was treated with oxone (3.10 g, 5.04 mmol). The heterogenous solution was stirred for 3 days at RT. Aqueous sodium sulfite (sat.) was added and the mixture was extracted with DCM (3×). The combined organic layers were dried over anhydrous sodium sulfate, filtered and concentrated to give 660 mg of a clear oil. The crude material was purified by ISCO (40 g column, 5-25% EtOAc in hexanes) to afford the title compound (0.517 g, 76.9% yield) as a white solid. MS (ESI, pos. ion) m/z: 268.9 (M+1).

Step 5: 2-(5-Fluoro-2-methyl-4-(methylsulfonyl)phenyl)-4,4,5,5-tetramethyl-1,3,2-dioxaborolane A mixture of 1-bromo-5-fluoro-2-methyl-4-(methylsulfonyl)benzene (511 mg, 1.91 mmol), 4,4,5,5-tetramethyl-2-(4,4,5,5-tetramethyl-1,3,2-dioxaborolan-2-yl)-1,3,2-dioxaborolane (729 mg, 2.87 mmol), dichloro[1,1'-bis(diphenylphosphino)ferrocene]palladium (II) dichloromethane adduct (14 mg, 0.19 mmol) and potassium acetate (939 mg, 9.57 mmol) in 10 mL of DMF was heated to 80° C. overnight. After cooling to RT, the reaction mixture was concentrated. The residue was taken up in EtOAc and 2M HCl, filtered and separated. The organic layer was dried over sodium sulfate, filtered and concentrated to give 1.05 g of brown oil. The crude material was purified by ISCO (40 g column, 0-25% EtOAc in hexanes) to give the title compound (417 mg, 69% yield) as a white solid. MS (ESI, pos. ion) m/z: 337.0 (M+Na)

Step 6: N-Cyclopropyl-3-(1-(5-fluoro-2-methyl-4-(methylsulfonyl)phenyl)phthalazin-6-yl)-4-methylbenzamide In a glass tube was placed 3-(1-chlorophthalazin-6-yl)-N-cyclopropyl-4-methylbenzamide (0.100 g, 0.30 mmol), 2-(5-fluoro-2-methyl-4-(methylsulfonyl)phenyl)-4,4,5,5-tetramethyl-1,3,2-dioxaborolane (0.12 g, 0.38 mmol), tetrakis(triphenylphosphine)palladium (0.034 g, 0.030 mmol) and 2 M potassium carbonate (0.44 mL, 0.89 mmol) in 2.0 mL of 4/1=DME/EtOH. The mixture was heated in the microwave at 140° C. for 20 min. Water was then added and the mixture was extracted with EtOAc (3×). The combined organic layers were dried over anhydrous sodium sulfate, filtered and concentrated to give 250 mg of a brown foam. The brown foam was dissolved in 2.0 mL of MeOH and purified by a reversed phase HPLC (using 5-95% of [0.1% TFA in ACN] in [0.1% of TFA in water]). The desired fractions were collected, the solvents were removed under reduced pressure. The residue was treated with 1 N NaOH and extracted with EtOAc (2×). The combined EtOAc layers were dried over sodium sulfate and concentrated to afford N-cyclopropyl-3-(1-(5-fluoro-2- methyl-4-(methylsulfonyl)phenyl)phthalazin-6-yl)-4-methylbenzamide as a white solid. MS (ESI, pos. ion) m/z: 490.0 (M+1).

Example 224

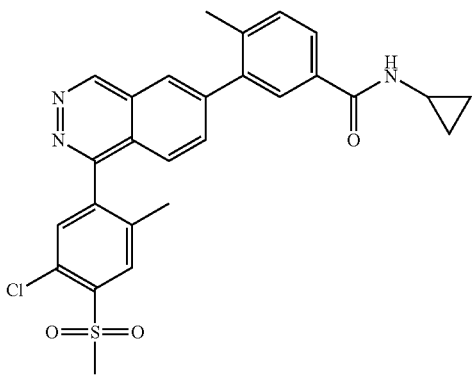

Synthesis of 3-(1-(5-chloro-2-methyl-4-(methylsulfonyl)phenyl)phthalazin-6-yl)-N-cyclopropyl-4-methylbenzamide Step 1: 2-(5-Chloro-2-methyl-4-(methylsulfonyl)phenyl)-4,4,5,5-tetramethyl-1,3,2-dioxaborolane The title compound was prepared by a method analogous to that described for 2-(5-fluoro-2-methyl-4-(methylsulfonyl)phenyl)-4,4,5,5-tetramethyl-1,3,2-dioxaborolane (Steps 1-5 of Example 223), using 2-chloro-5-methylphenol as the starting material. MS (ESI, pos. ion) m/z: 353.0 (M+Na).

Step 2: 3-(1-(5-chloro-2-methyl-4-(methylsulfonyl)phenyl)phthalazin-6-yl)-N-cyclopropyl-4-methylbenzamide This material was prepared according to the procedure similar to that described in Method A-Example 3a, using 3-(1-chlorophthalazin-6-yl)-N-cyclopropyl-4-methylbenzamide and 2-(5-chloro-2-methyl-4-(methylsulfonyl)phenyl)-4,4,5,5-tetramethyl-1,3,2-dioxaborolane. MS (ESI, pos. ion) m/z: 506.9 (M+1).

Example 225 (Method G)

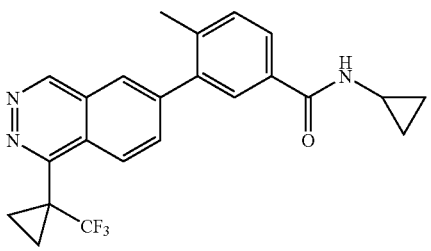

Synthesis of N-Cyclopropyl-4-methyl-3-(1-(1-(trifluoromethyl)cyclopropyl)phthalazin-6-yl)benzamide Preparation of (4-Chloro-2-methylphenyl)(1-(trifluoromethyl)cyclopropyl)methanone Step 1: Trifluoromethyl cyclopropane carboxylic acid (500 mg, 3.24 mmol) was added to a freshly prepared solution of Weinreb amine (3.90 mmol) prepared by treating N-methoxymethanamine HCl salt with $EtN-iPr_2$ (3.90 mmol) in $CH_2Cl_2$ at −40° C. and stirring for 5 min. DCC (801 mg, 3.90 mmol) in 5.0 mL of DCM was then added slowly over 3 min while cooling the solution at 0° C. The reaction mixture was stirred at RT for 48 h. It was then filtered through a plug of silica gel washing with $Et_2O$. The volatiles were removed and the residue was purified on an ISCO 12 g column (20-70% EtOAc:Hexanes) to yield N-methoxy-N-methyl-1-(trifluoromethyl)cyclopropanecarboxamide (456 mg, 71% yield) as a clear colorless oil. A reference for this procedure could be found in: *J. Org. Chem.* 2005, 70, pages 5721-5724.

Step 2: At 0° C., a solution of 4-chloro-1-iodo-2-methylbenzene (642 mg, 2.53 mmol) in 5 mL of pentane was treated with t-BuLi (1.68 mL of 1.7 M in pentane solution, 2.86 mmol) slowly, and stirred for 30 min. The resulting yellow mixture was cooled to −60° C., and a solution of N-methoxy-N-methyl-1-(trifluoromethyl)cyclopropanecarboxamide (346 mg, 1.75 mmol) in 3.0 mL of THF was added via syringe. The reaction mixture was slowly warmed to RT in 1 h, then partitioned between a mixture of sat. ammonium chloride and EtOAc. The organic layer was separated, dried and concentrated. Purification of the residue on the ISCO (12 g column, 0-10% EtOAc:Hexanes) provided the title compound (384 mg, 83%) as a colorless amorphous solid. MS (ESI, pos. ion) m/z: 263.1 (M+1).

Step 3: 6-Chloro-1-(1-(trifluoromethyl)cyclopropyl)phthalazine

A mixture of (4-chloro-2-methylphenyl)(1-(trifluoromethyl)cyclopropyl)methanone (384 mg, 1.46 mmol) in 20.0 mL of carbon tetrachloride was treated with NBS (624 mg, 3.5 mmol) and benzoyl peroxide (74 mg). The mixture was heated at 83° C. in an oil bath for 16 h. After cooling to RT, it was filtered through a sintered glass frit and rinsed with 5 mL of carbon tetrachloride affording a yellow, viscous oil (726 mg). The oil was then treated with 4.0 mL hydrazine hydrate and stirred in an oil bath at 37° C. for 3 h. It was then diluted with water and extracted 3×20 mL of $CH_2Cl_2$. The combined organic solution was dried over $MgSO_4$, filtered and concentrated. Purification of the residue by ISCO (12 g column, 25-50% EtOAc in Hexanes) afforded 6-chloro-1-(1-(trifluoromethyl)cyclopropyl)phthalazine (136 mg, 34% over 2 steps) as a light yellow amorphous solid. MS (ESI, pos. ion) m/z: 273.0 (M+1).

Preparation of N-Cyclopropyl-4-methyl-3-(1-(1-(trifluoromethyl)cyclopropyl)phthalazin-6-yl)benzamide A mixture of 6-chloro-1-(1-(trifluoromethyl)cyclopropyl)phthalazine (20 mg, 73 mmol), N-cyclopropyl-4-methyl-3-(4,4,5,5-tetramethyl-1,3,2-dioxaborolan-2-yl)benzamide (27 mg, 88 μmol), $Pd_2(dba)_3$ (2.0 mg, 2.2 μmol), potassium phosphate (47 mg, 220 μmol) and X-Phos (2.0 mg) in 1.0 mL of dioxane and 0.5 mL water in a sealed glass tube was heated in a microwave for 20 min at 135° C. The mixture was partitioned between 1.0 N NaOH (1.0 mL) and EtOAc (5.0 mL).

The organic layer was separated, dried and concentrated. Purification on an ISCO (4.0 g column, 60-100% EtOAc:Hexanes) provided the title compound as a yellow amorphous solid. MS (ESI, pos. ion) m/z: 412.1 (M+1).

Example 226

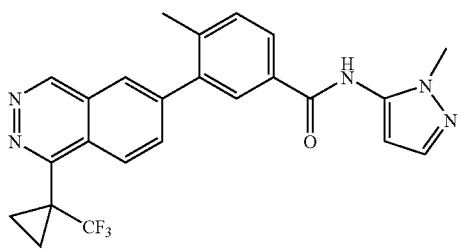

Synthesis of 4-Methyl-N-(1-methyl-1H-pyrazol-5-yl)-3-(1-(1-(trifluoromethyl)cyclopropyl)phthalazin-6-yl)benzamide The title compound was prepared according to a procedure analogous to that described in Example 225, using 4-methyl-N-(1-methyl-1H-pyrazol-5-yl)-3-(4,4,5,5-tetramethyl-1,3,2-dioxaborolan-2-yl)benzamide and 6-chloro-1-(1-(trifluoromethyl)cyclopropyl)phthalazine as the starting materials. MS (ESI, pos. ion) m/z: 452.2 (M+1).

Examples 227a and 227b

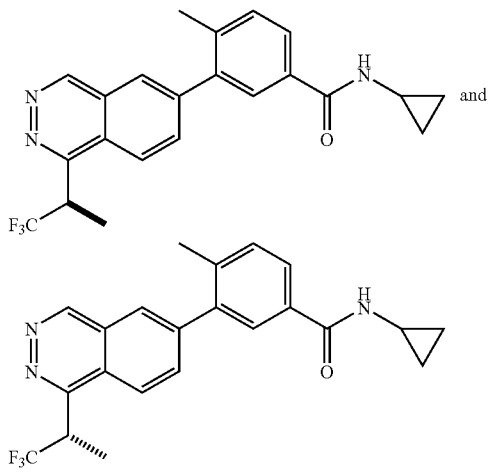

Synthesis of N-Cyclopropyl-4-methyl-3-(1-((R)-1,1,1-trifluoropropan-2-yl)phthalazin-6-yl)benzamide (Example 227a) and N-Cyclopropyl-4-methyl-3-(1-((S)-1,1,1-trifluoropropan-2-yl)phthalazin-6-yl)benzamide (Example 227b)

Step 1: Methyl 3-(1-chlorophthalazin-6-yl)-4-methylbenzoate

In a 500 mL RBF was added methanol (200 mL, 54 mmol) followed by oxalyl chloride (5.0 ml, 54 mmol) drop wise while cooling with an ice bath. It was stirred for 5 min. and 3-(1-hydroxyphthalazin-6-yl)-4-methylbenzoic acid (15.00 g, 54 mmol) was then added in portions over 2 min. The reaction was fitted with a reflux condenser and heated to 85° C. in an oil bath for 2 h. The reaction mixture was concentrated on the rotovap then under high vacuum overnight. The resulting white fluffy solid in 260 mL of anhydrous CH$_3$CN was treated with POCl$_3$ (9.9 mL, 107 mmol), and heated to 70° C. in an oil bath for 4 h. The reaction mixture was cooled to RT and filtered through a sintered glass frit to remove the suspended solid, and rinsed with 50 mL of CH$_3$CN. The filtrate was concentrated to give a yellow oil. The oil was dissolved in 250 mL CH$_2$Cl$_2$, washed with a saturated solution of NaHCO$_3$ followed by brine. The organic solution was dried over MgSO$_4$, filtered and concentrated to give methyl 3-(1-chlorophthalazin-6-yl)-4-methylbenzoate (14.54 g, 87% yield) as a tan crystalline. This crude material was used in the next step without further purification. MS (ESI, pos. ion) m/z: 313.1 (M+1).

Step 2: Methyl 4-methyl-3-(1-(1,1,1-trifluoroprop-2-en-2-yl)phthalazin-6-yl)benzoate A mixture of methyl 3-(1-chlorophthalazin-6-yl)-4-methylbenzoate (1.0 g, 3.2 mmol), 4,4,6-trimethyl-2-(1,1,1-trifluoroprop-2-en-2-yl)-1,3,2-dioxaborinane (0.99 g, 4.48 mmol), tetrakis(triphenylphosphine)palladium (185 mg, 0.16 mmol), and sodium carbonate monohydrate (1.2 g, 9.59 mmol) in dioxane/H$_2$O (3:1, 12 mL) was heated in a microwave reactor at 100° C. for 80 min. The reaction mixture was partitioned between EtOAc (30 mL) and H$_2$O (30 mL); the layers were separated, and the aqueous layer was extracted with EtOAc (2×30 mL). The combined organic layers were dried (MgSO$_4$) and concentrated under reduced pressure. The resulting dark oil was dissolved in 2% Et$_3$N in EtOAc, evaporated onto some silica gel, and purified by flash chromatography (Biotage Si 40+S, 20-60% of 2% Et$_3$N in EtOAc/hexanes) to provide methyl 4-methyl-3-(1-(1,1,1-trifluoroprop-2-en-2-yl)phthalazin-6-yl)benzoate (833 mg, 70% yield) as a brown solid. MS (ESI, pos. ion) m/z: 373.2 (M+1).

Step 3: Methyl 4-methyl-3-(1-(1,1,1-trifluoropropan-2-yl)phthalazin-6-yl)benzoate (7a) and methyl 3-(1-(1,1-difluoropropan-2-yl)phthalazin-6-yl)-4-methylbenzoate A mixture of methyl 4-methyl-3-(1-(1,1,1-trifluoroprop-2-en-2-yl)phthalazin-6-yl)benzoate (2.45 g, 6.58 mmol) and palladium (10 wt. % on activated carbon, 700 mg, 0.66 mmol) in THF (65 mL) was stirred under an atmosphere of hydrogen at RT for 5 h. The mixture was filtered through a Celite pad and rinsed with EtOAc (100 mL). 5 M aqueous potassium permanganate (2.63 mL, 13.16 mmol) was added and the biphasic mixture was stirred at RT for 15 min. The mixture was diluted with H$_2$O (100 mL), and the layers were separated. The aqueous layer was extracted with EtOAc (2×100 mL), and the combined organic layers were washed with 2 N aqueous Na$_2$SO$_3$ (100 mL), dried (MgSO$_4$), and concentrated under reduced pressure. The resulting yellow oil was dissolved in CH$_2$Cl$_2$, evaporated onto silica gel, and purified by flash chromatography (Biotage Si 40+M, 20% to 60% EtOAc/hexane) to provide a light yellow foam (1.84 g) as a mixture of methyl 4-methyl-3-(1-(1,1,1-trifluoropropan-2-yl)phthalazin-6-yl)benzoate (about 96%) and methyl 3-(1-(1,1-difluoropropan-2-yl)phthalazin-6-yl)-4-methylbenzoate (about 4%). This mixture was used in the next step without further purification. MS (ESI, pos. ion) m/z: 373.2 (M+1) for methyl 4-methyl-3-(1-(1,1,1-trifluoropropan-2-yl)phthalazin-6-yl)benzoate; MS (ESI, pos. ion) m/z: 357.1 (M+1) for methyl 3-(1-(1,1-difluoropropan-2-yl)phthalazin-6-yl)-4-methylbenzoate.

Step 4: N-Cyclopropyl-4-methyl-3-(1-((R)-1,1,1-trifluoropropan-2-yl)phthalazin-6-yl)benzamide (Example 227a), N-Cyclopropyl-4-methyl-3-(1-((S)-1,1,1-trifluoropropan-2-yl)phthalazin-6-yl)benzamide and N-cyclopropyl-3-(1-(1,1-difluoropropan-2-yl)phthalazin-6-yl)-4-methylbenzamide (Example 227b)

Trimethylaluminum (11.89 mL of 2.0 M solution in hexane, 23.78 mmol) was added to a solution of cyclopropylamine (1.65 ml, 23.78 mmol) in CH$_2$Cl$_2$ (20 mL) at 0° C. and the mixture was stirred at RT for 0.5 h. A solution of methyl 4-methyl-3-(1-(1,1,1-trifluoropropan-2-yl)phthalazin-6-yl)benzoate (2.96 g, 7.93 mmol, with about 4% of methyl 3-(1-(1,1-difluoropropan-2-yl)phthalazin-6-yl)-4-methylbenzoate) in CH$_2$Cl$_2$ (10 mL) was added via cannula and the mixture was heated under reflux for 20 h. The mixture was poured into a saturated aqueous sodium potassium tartrate (250 mL). EtOAc (250 mL) was added, and the resulting biphasic mixture was rigorously stirred for 3 h. The layers were separated, and the aqueous layer was extracted with EtOAc (2×200 mL). The combined organic layers were dried (MgSO$_4$) and concentrated under reduced pressure. The resulting yellow oil was dissolved in CH$_2$Cl$_2$, evaporated onto some silica gel, and purified by flash chromatography (Biotage Si 40+M, 3% to 8% MeOH/CH$_2$Cl$_2$) to provide 3.03 g of a white foam, as a mixture of the racemic N-cyclopropyl-4-methyl-3-(1-(1,1,1-trifluoropropan-2-yl)phthalazin-6-yl)benzamide (about 96%) and N-cyclopropyl-3-(1-(1,1-difluoropropan-2-yl)phthalazin-6-yl)-4-methylbenzamide (about 4%).

The above obtained white foam was purified on a preparative HPLC (conditions see below) to provide the following three compounds:
1) MS (ESI, pos. ion) m/z: 400.4 (M+1). N-cyclopropyl-4-methyl-3-(1-((R)-1,1,1-trifluoropropan-2-yl)phthalazin-6-yl)benzamide (1.26 g), as an off white amorphous solid;
2) MS (ESI, pos. ion) m/z: 400.4 (M+1). N-cyclopropyl-4-methyl-3-(1-((S)-1,1,1-trifluoropropan-2-yl)phthalazin-6-yl)benzamide (1.02 g), as an off white amorphous solid; and Example 228

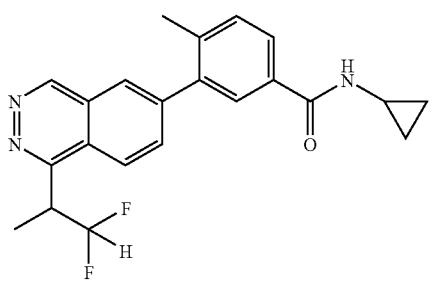

3) MS (ESI, pos. ion) m/z: 382.0 (M+1). N-cyclopropyl-3-(1-(1,1-difluoropropan-2-yl)phthalazin-6-yl)-4-methylbenzamide (16 mg), as an off white amorphous solid.
Preparative HPLC Method:

Column: MODCOL Spring Load Column, 4"×35 cm containing ~2000 g of Whelk-O, SS, 10u, as chiral stationary phase
Mobile Phase: Acetonitrile/MtBE/15/85 (pre-mixed in A line)
Flow Rate: 400 ml/min
Back Pressure: ~700 PSI
Sample Preparation: Dissolved in mobile phase at 50 mg/ml
Wavelength: 250 nm Examples 229 and 230

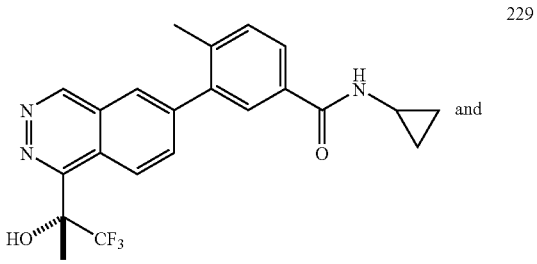

229

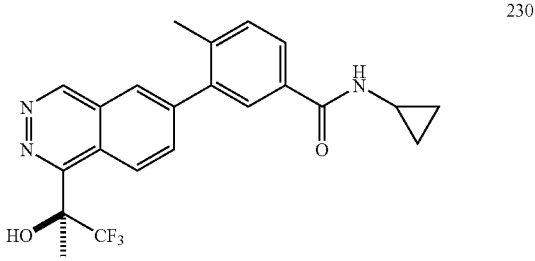

230

Synthesis of N-Cyclopropyl-4-methyl-3-(1-((R)-1,1,1-trifluoro-2-hydroxypropan-2-yl)phthalazin-6-yl)benzamide (Example 229) and N-cyclopropyl-4-methyl-3-(1-((S)-1,1,1-trifluoro-2-hydroxypropan-2-yl)phthalazin-6-yl)benzamide (Example 230)

Step 1: 1-(6-Chlorophthalazin-1-yl)ethanone

In a glass tube, a mixture of 1,6-dichlorophthalazine (1.18 g, 5.93 mmol) in 7.0 mL of DMF was treated with copper(I) iodide (113 mg, 0.59 mmol), tetrakistriphenylphosphine palladium (343 mg, 0.29 mmol) followed by tributyl(1-ethoxyvinyl)stannane (2.10 mL, 6.23 mmol). The glass tube was sealed and heated at 100° C. for 25 min in a microwave. The mixture was loaded on a silica gel column, eluting with 50-100% EtOAc in Hexanes, to provide 6-chloro-1-(1-ethoxyvinyl) phthalazine as a brown oil. MS (ESI, pos. ion) m/z: 235.1 (M+1).

The above obtained brown oil in 5 mL of THF and 2N HCl (7.4 mL) was heated at 50° C. in an oil bath for 1.5 h. The reaction mixture was diluted with EtOAc and basified with sat. NaHCO₃. The organic solution was washed with brine, dried over MgSO₄, and concentrated. The crude material was purified on an ISCO (40 g column, 30-100% EtOAc:Hexanes) to afford 1-(6-chlorophthalazin-1-yl)ethanone (844 mg, 69% yield) as a yellow amorphous solid. MS (ESI, pos. ion) m/z: 207.0 (M+1).

Preparation of N-Cyclopropyl-4-methyl-3-(1-((R)-1,1,1-trifluoro-2-hydroxypropan-2-yl)phthalazin-6-yl)benzamide (Ex. 229) and N-cyclopropyl-4-methyl-3-(1-((S)-1,1,1-trifluoro-2-hydroxypropan-2-yl)phthalazin-6-yl)benzamide (Ex. 230)

Step 1: A mixture of 1-(6-chlorophthalazin-1-yl)ethanone (476 mg, 2.30 mmol) in 5 mL of THF at 0° C. was treated with trimethyl(trifluoromethyl)silane (0.44 mL, 3.0 mmol) followed by TBAF (58 µL, 58 µmol). The resulting clear orange solution was allowed to stir at RT for 15 min, then treated with sat NH₄Cl and extracted with 2×15 mL EtOAc. The combined EtOAc layers were washed with brine, dried over MgSO₄, and concentrated to afford 700 mg of a brown amorphous solid as a mixture of the tertiary alcohol and its silyl ether. The crude material was used in the next step without further purification.

Step 2: The mixture obtained in step 1, N-cyclopropyl-4-methyl-3-(4,4,5,5-tetramethyl-1,3,2-dioxaborolan-2-yl)benzamide (680 mg, 2.25 mmol), potassium phosphate (1.20 g, 5.64 mmol), tris(dibenzylideneacetone)dipalladium (63 mg, 0.069 mmol) and X-Phos (66 mg, 0.138 mmol) in 6.0 mL of dioxane and 2.5 mL of water were placed in a sealed glass tube and heated at 122° C. for 25 min in a microwave. The reaction mixture was partitioned between 1 N NaOH and EtOAc. The EtOAc layer was separated, dried and concentrated. Purification on a 40 g ISCO column (50-100% EtOAc in Hexanes) provided racemic N-cyclopropyl-4-methyl-3-(1-(1,1,1-trifluoro-2-hydroxypropan-2-yl)phthalazin-6-yl)benzamide (815 mg, 86.9% yield) as a yellow amorphous solid. MS (ESI, pos. ion) m/z: 416.1 (M+1).

The racemic mixture was subjected to Preparative SFC separation using following conditions to give the chiral compounds:

Ex 229) N-cyclopropyl-4-methyl-3-(1-((R)-1,1,1-trifluoro-2-hydroxypropan-2-yl)phthalazin-6-yl)benzamide as a yellow amorphous solid. MS (ESI, pos. ion) m/z: 416.1 (M+1); and Ex 230) N-cyclopropyl-4-methyl-3-(1-((S)-1,1,1-trifluoro-2-hydroxypropan-2-yl)phthalazin-6-yl)benzamide as a yellow amorphous solid. MS (ESI, pos. ion) m/z: 416.1 (M+1).

Preparative SFC Method:
Berger Multigram II SFC
Column: Chiralpak AD-H (250×21 mm, 5 mm)
Mobile Phase:
  A: Liquid CO₂
  B: Methanol
Isocratic: 74:26 (A:B)
Flow Rate: 65 mL/min
Column/Oven Temperature: 40° C.
Outlet Pressure: 100 bar Example 231

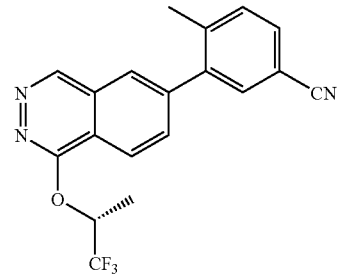

Synthesis of 4-Methyl-3-(1-((R)-1,1,1-trifluoropropan-2-yloxy)phthalazin-6-yl)benzonitrile Step 1: 4-Methyl-3-(1-(1,1,1-trifluoropropan-2-yloxy)phthalazin-6-yl)benzenamine The title compound was prepared according to a procedure similar to that described in Example 225, using 6-chloro-1-(1,1,1-trifluoropropan-2-yloxy)phthalazine and 4-methyl-3-(4,4,5,5-tetramethyl-1,3,2-dioxaborolan-2-yl)benzenamine as starting materials. MS (ESI, pos. ion) m/z: 348.1 (M+1). The racemic material was subjected to Preparative SFC separation using a chiral column to afford its (R)- and (S)-enantiomers.

Step 2: 6-(5-Iodo-2-methylphenyl)-1-((R)-1,1,1-trifluoropropan-2-yloxy)phthalazine To a suspension of 4-methyl-3-(1-((R)-1,1,1-trifluoropropan-2-yloxy)phthalazin-6-yl)benzenamine (1.49 g, 4.30 mmol) in 14 mL of 6N HCl at 0° C. was added sodium nitrite (593 mg, 8.59 mmol) in 8 mL of water drop wise. After 20 min at 0° C., a solution of potassium iodide (2.14 g, 12.89 mmol) in 6 mL of water was added slowly. After the brown heterogeneous mixture was stirred at RT for 1 h, it was extracted twice with DCM. The combined DCM layers were washed with 1 N NaOH followed by sat. sodium thiosulfate, dried and concentrated. The brown residue was purified on an ISCO 40 g column (25-55% EtAc in Hexanes) to provide 6-(5-iodo-2-methylphenyl)-1-((R)-1,1,1-trifluoropropan-2-yloxy)phthalazine (73% yield, 1.44 g) as an off-white amorphous solid. MS (ESI, pos. ion) m/z: 459.0 (M+1).

Step 3: 4-Methyl-3-(1-((R)-1,1,1-trifluoropropan-2-yloxy)phthalazin-6-yl)benzonitrile A mixture of 6-(5-iodo-2-methylphenyl)-1-((R)-1,1,1-trifluoropropan-2-yloxy)phthalazine (100 mg, 0.22 mmol) and copper cyanide (98 mg, 1.09 mmol) in 1.0 mL of DMF in a sealed glass tube was heated at 120° C. in a microwave synthesizer for 20 min. The cooled reaction was diluted with CH₂Cl₂ and washed with water and brine. The organic layer was dried (MgSO₄), filtered, and concentrated. Purification on a silica gel column (20-50% of EtOAc in Hexanes)

afforded 4-methyl-3-(1-((R)-1,1,1-trifluoropropan-2-yloxy)phthalazin-6-yl)benzonitrile as a white solid. MS (ESI, pos. ion) m/z: 358.4 (M+1).

Example 232

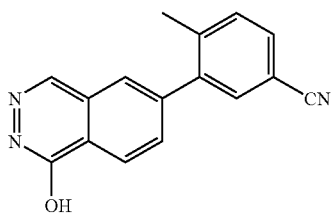

Synthesis of 3-(1-Hydroxyphthalazin-6-yl)-4-methylbenzonitrile

A mixture of 4-methyl-3-(1-((R)-1,1,1-trifluoropropan-2-yloxy)phthalazin-6-yl)benzonitrile (98.9 mg, 277 µmol) and 20% sulfuric acid (1 mL) in a sealed tube was heated at 150° C. in a oil bath for 30 min. The reaction mixture was cooled, then diluted with water and neutralized (to pH~7) with saturated aqueous $NaHCO_3$ solution. The mixture was extracted with 10% $MeOH/CHCl_3$ (3×5 mL) and the combined organic extracts were dried ($MgSO_4$), filtered, and concentrated in vacuo. Purification on a silica gel column (1-10% MeOH in $CH_2Cl_2$) afforded 3-(1-hydroxypbthalazin-6-yl)-4-methylbenzonitrile (28.5 mg, 39% yield) as a white crystalline solid. MS (ESI, pos. ion) m/z: 262.4 (M+1).

Example 233

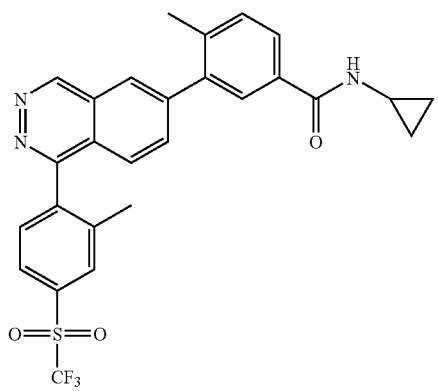

Synthesis of N-Cyclopropyl-4-methyl-3-(1-(2-methyl-4-(trifluoromethylsulfonyl)phenyl)phthalazin-6-yl)benzamide Step 1: Methyl 4-methyl-3-(1-(2-methyl-4-(trifluoromethylsulfonyl)phenyl)phthalazin-6-yl)benzoate was prepared according to the procedure described in Example 223, using 4,4,5,5-tetramethyl-2-(2-methyl-4-(trifluoromethylsulfonyl)phenyl)-1,3,2-dioxaborolane and methyl 3-(1-chlorophthalazin-6-yl)-4-methylbenzoate as starting materials. MS (ESI, pos. ion) m/z: 500.9 (M+1).

Step 2: To a solution of methyl 4-methyl-3-(1-(2-methyl-4-(trifluoromethylsulfonyl)phenyl)phthalazin-6-yl)benzoate (120 mg, 0.24 mmol) in 3 mL of 2/1 THF/MeOH was added NaOH (30 mg, 0.72 mmol) at RT. After 8 h, the mixture was acidified with 2M HCl and extracted with DCM (3×). The combined DCM layers were washed with brine, dried and concentrated to afford the 4-methyl-3-(1-(2-methyl-4-(trifluoromethylsulfonyl)phenyl)phthalazin-6-yl)benzoic acid (82 mg) as a tan solid. The crude acid was used in the next step. MS (ESI, pos. ion) m/z: 486.9 (M+1).

Step 3: A solution of the above obtained 4-methyl-3-(1-(2-methyl-4-(trifluoromethylsulfonyl)phenyl)phthalazin-6-yl)benzoic acid (82 mg, 0.17 mmol) in 2 mL of DMF at RT was treated with HATU (96 mg, 0.25 mmol) and cyclopropylamine (0.12 mL, 1.7 mmol). The reaction mixture was stirred overnight. Water was then added and the mixture was extracted with EtOAc (3×). The combined organic layers were dried over anhydrous sodium sulfate, filtered and concentrated. The brown residue was loaded on an ISCO 12 g column (0-5% (2M ammonia in MeOH) in dichloromethane) to afford the title compound (50 mg, 56% yield) as an off-white solid. MS (ESI, pos. ion) m/z: 525.9 (M+1).

Example 234

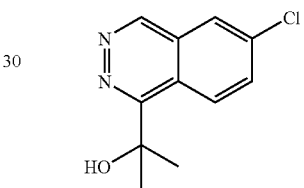

Synthesis of 2-(6-Chlorophthalazin-1-yl)propan-2-ol

A solution of 1-(6-chlorophthalazin-1-yl)ethanone (350 mg, 1.69 mmol) in 20 mL of THF at 0° C. was treated with 0.8 mL MeMgBr (3.16 M in $Et_2O$) and stirred at 0° C. for 1 h. The mixture was quenched with saturated $NH_4Cl$, and extracted 2×20 mL EtOAc. The combined EtOAc layers were dried over $MgSO_4$, filtered and concentrated. Purification on an ISCO (12 g column, 15-50% EtOAc:Hexanes) afforded 2-(6-chlorophthalazin-1-yl)propan-2-ol (172 mg, 46% yield) as a pale yellow amorphous solid. MS (ESI, pos. ion) m/z: 223.1 (M+1).

Example 235

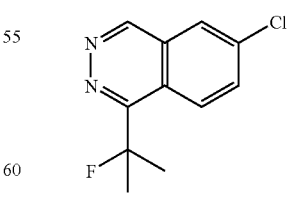

A mixture of 2-(6-chlorophthalazin-1-yl)propan-2-ol (154 mg, 0.69 mmol) in 5 mL of DCM at −78° C. was treated with DAST (0.11 mL, 0.76 mmol) slowly. It was warmed slowly to room temperature overnight, then quenched with saturated $NaHCO_3$ solution and extracted with $CH_2Cl_2$. The DCM layer was dried over MgSO$_4$, filtered and concentrated. Purification on an ISCO (12 g column, 10-35% EtOAc:Hexanes) afforded 6-chloro-1-(2-fluoropropan-2-yl)phthalazine (84 mg, 54% yield) as a pale yellow, viscous oil. MS (ESI, pos. ion) m/z: 225.1 (M+1).

Example 236

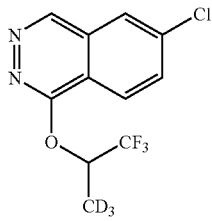

Synthesis of 6-chloro-1-(1,1,1-trifluoro-trideuteratedpropan-2-yloxy)phthalazine Step 1: A solution of CD$_3$CHO (1.00 g, 21.2 mmol), trimethyl(trifluoromethyl)silane (3.23 mL, 21.9 mmol) in 3.0 mL of DME at 0° C. was treated with cesium fluoride (32.3 mg, 0.212 mmol). After the reaction mixture was slowly warmed to RT in 4 h, it was quenched with 5.0 mL of 1 N HCl, and extracted with 2×10 mL of MTBE. The combined organic solution was washed with 10 mL of sat. NaHCO$_3$ followed by brine, and dried over MgSO$_4$. $^{19}$F-NMR of the crude product in MTBE indicated only one fluorine containing compound. It was used as a solution in MTBE for the next step. A reference for this procedure could be found in Shreeve, J. M. et al. *J. Org. Chem.* 1999, 64, 2873-2876.

Step 2: In a 100 mL RBF was added 1,6-dichlorophthalazine (750 mg, 3.78 mmol), the above obtained CD$_3$CH(OH)CF$_3$ (2.49 g, 21.3 mmol) in MTBE (ca. 20 mL), followed by aliquat 100-s (0.45 mmol, 0.23 mL of a 50% solution in water) and 10 N NaOH (1.1 mL). The reaction flask was fitted with a reflux condenser and heated in an oil bath at 50° C. for 4 h. The reaction mixture was partitioned between EtOAc (100 mL) and water (10 mL). The EtOAc layer was washed with brine, dried over MgSO$_4$, filtered and concentrated. Purification on the ISCO (40 g column, 30-50% EtOAc: Hexanes) afforded 6-chloro-1-(1,1,1-trifluoro-trideuteratedpropan-2-yloxy)phthalazine (850 mg, 81% yield) as an off-white amorphous solid. MS (ESI, pos. ion) m/z: 280.4 (M+1).

TABLE 4

| Example No. | Compound Name (IUPAC) | Mass Spec (M + H+) | Method | AA5225_IC50_IP (Avg) | AA2734_IC50_IP (Avg) |
|---|---|---|---|---|---|
| 223 | N-cyclopropyl-3-(1-(5-fluoro-2-methyl-4-(methylsulfonyl)phenyl)-6-phthalazinyl)-4-methylbenzamide | 490 | F | 0.000854 | 0.001218 |
| 225 | N-cyclopropyl-4-methyl-3-(1-(1-(trifluoromethyl)cyclopropyl)-6-phthalazinyl)benzamide | 412.1 | G | 0.000968 | 0.000148 |
| 224 | 3-(1-(5-chloro-2-methyl-4-(methylsulfonyl)phenyl)-6-phthalazinyl)-N-cyclopropyl-4-methylbenzamide | 506.9 | F | 0.00089 | 0.003684 |
| 237 | 4-methyl-3-(1-((2,2,2-trifluoro-1-methylethyl)oxy)-6-phthalazinyl)aniline | 348.1 | F | | |
| 238 | 4-methyl-3-(1-(((1R)-2,2,2-trifluoro-1-methylethyl)oxy)-6-phthalazinyl)aniline | 348.1 | G | | |
| 239 | 4-methyl-3-(1-(((1S)-2,2,2-trifluoro-1-methylethyl)oxy)-6-phthalazinyl)aniline | 348.1 | G | | |
| 231 | 4-methyl-3-(1-(((1R)-2,2,2-trifluoro-1-methylethyl)oxy)-6-phthalazinyl)benzonitrile | 358.4 | | 0.080811 | 0.033332 |
| 226 | 4-methyl-N-(1-methyl-1H-pyrazol-5-yl)-3-(1-(1-(trifluoromethyl)cyclopropyl)-6-phthalazinyl)benzamide | 452.2 | F | 0.001121 | 0.000173 |
| 240 | 4-methyl-N-(1-methyl-1H-pyrazol-5-yl)-3-(1-((1R)-2,2,2-trifluoro-1-methylethyl)-6-phthalazinyl)benzamide | 440.1 | H | | |
| 241 | 4-methyl-N-(1-methyl-1H-pyrazol-5-yl)-3-(1-((1R)-2,2,2-trifluoro-1-methylethyl)-6-phthalazinyl)benzamide | 440.1 | H | | |
| 242 | 4-methyl-N-(1-methyl-1H-pyrazol-5-yl)-3-(1-((1S)-2,2,2-trifluoro-1-methylethyl)-6-phthalazinyl)benzamide | 440.1 | H | | |
| 227a | N-cyclopropyl-4-methyl-3-(1-((1R)-2,2,2-trifluoro-1-methylethyl)-6-phthalazinyl)benzamide | 400.4 | H | 0.001084 | 0.000455 |
| 227b | N-cyclopropyl-4-methyl-3-(1-((1S)-2,2,2-trifluoro-1-methylethyl)-6-phthalazinyl)benzamide | 400.4 | H | 0.001608 | 0.00033 |

TABLE 4-continued

| Example No. | Compound Name (IUPAC) | Mass Spec (M + H+) | Method | AA5225_IC50_IP (Avg) | AA2734_IC50_IP (Avg) |
|---|---|---|---|---|---|
| 232 | 3-(1-hydroxy-6-phthalazinyl)-4-methylbenzonitrile | 262.4 | | 0.001332 | 0.000252 |
| 243 | 4-methyl-N-(1-methyl-1H-pyrazol-5-yl)-3-(1-(2,2,2-trifluoro-1-hydroxy-1-methylethyl)-6-phthalazinyl)benzamide | 456.3 | G | 0.001332 | 0.000252 |
| 244 | N-cyclopropyl-4-methyl-3-(1-(2,2,2-trifluoro-1-hydroxy-1-methylethyl)-6-phthalazinyl)benzamide | 416.1 | G | 0.000952 | 0.000434 |
| 245 | 4-methyl-3-(1-(((1S)-2,2,2-trifluoro-1-methylethyl)oxy)-6-phthalazinyl)benzoic acid | 377 | | | |
| 246 | 4-methyl-3-(1-(((1R)-2,2,2-trifluoro-1-methylethyl)oxy)-6-phthalazinyl)benzoic acid | 377 | | | |
| 247 | 3-(1-(1-hydroxy-1-methylethyl)-6-phthalazinyl)-4-methylbenzoic acid | 323.2 | G | 1 | 2.5 |
| 248 | N-cyclopropyl-3-(1-(1-hydroxy-1-methylethyl)-6-phthalazinyl)-4-methylbenzamide | 362.4 | G | 0.000812 | 0.000826 |
| 230 | N-cyclopropyl-4-methyl-3-(1-((1S)-2,2,2-trifluoro-1-hydroxy-1-methylethyl)-6-phthalazinyl)benzamide | 416.1 | G | 0.000643 | 0.000364 |
| 229 | N-cyclopropyl-4-methyl-3-(1-((1R)-2,2,2-trifluoro-1-hydroxy-1-methylethyl)-6-phthalazinyl)benzamide | 416.1 | G | 0.000599 | 0.000383 |
| 249 | 3-(1-(1-fluoro-1-methylethyl)-6-phthalazinyl)-4-methyl-N-(1-methyl-1H-pyrazol-5-yl)benzamide | 404.1 | G | 0.001142 | 0.000334 |
| 250 | 4-methyl-N-(1-methyl-1H-pyrazol-5-yl)-3-(1-((1S)-2,2,2-trifluoro-1-hydroxy-1-methylethyl)-6-phthalazinyl)benzamide | 456.3 | G | 0.000954 | 0.000296 |
| 251 | 4-methyl-N-(1-methyl-1H-pyrazol-5-yl)-3-(1-((1R)-2,2,2-trifluoro-1-hydroxy-1-methylethyl)-6-phthalazinyl)benzamide | 456.3 | G | 0.000913 | 0.0002 |
| 252 | N-cyclopropyl-3-(1-(1-fluoro-1-methylethyl)-6-phthalazinyl)-4-methylbenzamide | 364.2 | G | 0.000745 | 0.000242 |
| 253 | N-cyclopropyl-3-fluoro-5-(1-(1-fluoro-1-methylethyl)-6-phthalazinyl)-4-methylbenzamide | 382.1 | G | 0.000696 | 0.000168 |
| 233 | N-cyclopropyl-4-methyl-3-(1-(2-methyl-4-((trifluoromethyl)sulfonyl)phenyl)-6-phthalazinyl)benzamide | 525.9 | F | 0.00062 | 0.002887 |
| 254 | N-cyclopropyl-3-fluoro-4-methyl-5-(1-(((1R)-2,2,2-trifluoro-1-methylethyl)oxy)-6-phthalazinyl)benzamide | 434.1 | See A-1141-USP P80-82 for compound 28 & 29 | 0.000769 | 0.000501 |
| 255 | N-cyclopropyl-3-fluoro-4-methyl-5-(1-(((1S)-2,2,2-trifluoro-1-methylethyl)oxy)-6-phthalazinyl)benzamide | 434.1 | See A-1141-USP P80-82 for compound 28 & 29 | 0.000592 | 0.000307 |
| 256 | N-cyclopropyl-3-(1-((1S)-2,2-difluoro-1-methylethyl)-6-phthalazinyl)-4-methylbenzamide | 382 | H | 0.001029 | 0.00018 |
| 257 | N-ethyl-4-methyl-3-(1-(((1S)-2,2,2-trifluoro-1-methylethyl)oxy)-6-phthalazinyl)benzamide | 404.1 | ? | 0.001016 | 0.000813 |
| 258 | N,4-dimethyl-3-(1-(((1S)-2,2,2-trifluoro-1-methylethyl)oxy)-6-phthalazinyl)benzamide | 390.1 | ? | | 0.00175 |
| 259 | N-cyclopropyl-4-methyl-3-(1-((2,2,2-trifluoro-1-methylethyl)oxy)-6-phthalazinyl)benzamide-d 3 | 419 | G | 0.000991 | 0.001697 |
| 260 | 6-(5-amino-2-methylphenyl)-1-phthalazinol | 251.9 | G | | |

TABLE 4-continued

| Example No. | Compound Name (IUPAC) | Mass Spec (M + H+) | Method | AA5225_IC50_IP (Avg) | AA2734_IC50_IP (Avg) |
|---|---|---|---|---|---|
| 261 | 1,1-dimethylethyl(3-(1-hydroxy-6-phthalazinyl)-4-methylphenyl)carbamate | 351.9 | G | | |

The invention further provides methods or processes to make the compounds of Formulas I-IV. For example, and in one embodiment, the invention provides a method of making a compound according to Formula I, the method comprising the step of reacting a compound 7,

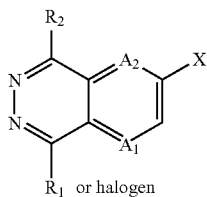

wherein $A^1$, $A^2$, $R^1$ and $R^2$ are as defined in Formula I herein and X is a halogen, with a boronic acid having a general formula

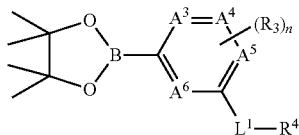

wherein $A^3$, $A^4$, $A^5$, $A^6$, $L^1$ and $R^4$ are defined herein in Formula I, to make a compound of Formula I.

In another embodiment, the invention provides a method of making a compound according to Formula II, the method comprising the step of reacting a compound 8,

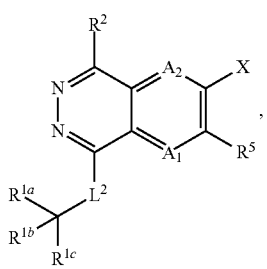

wherein $A^1$, $A^2$, $L^2$, $R^{1a}$, $R^{1b}$, $R^{1d}$, $R^2$ and $R^5$ are as defined herein in Formula II and X is a halogen, with a boronic acid having a general formula

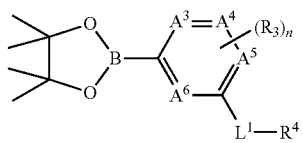

wherein $A^3$, $A^4$, $A^5$, $A^6$, $L^1$ and $R^4$ are defined herein in Formula II, to make a compound of Formula II.

Methods to make compounds of Formulas I-IV, within the scope of the present invention are described in co-pending U.S. patent application Ser. No. 11/367,123, which disclosure is herein incorporated by reference in its entirety.

While the examples described above provide processes for synthesizing compounds of Formulas I-IV, it should be appreciated that other methods may be utilized to prepare such compounds. Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, $4^{th}$ edition, Volume 15/1, Georg Thieme Verlag, Stuttgart (1974), in H.-D. Jakubke and H. Jescheit, Aminosäiuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., ethyl acetate; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

In synthesizing a compound of formulas I, II, III and IV according to a desired procedure, the steps may be performed in an order suitable to prepare the compound, including a procedure described herein or by an alternate order of steps described herein, and may be preceded, or followed, by additional protection/deprotection steps as necessary. The procedures may further use appropriate reaction conditions, including inert solvents, additional reagents, such as bases (e.g., LDA, DEA, pyridine, K$_2$CO$_3$, and the like), catalysts, and salt forms of the above. The intermediates may be isolated or carried on in situ, with or without purification. Purification methods are known in the art include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

In one embodiment, the present invention provides a method of making a compound of Formula I or II, the method comprising the step of reacting a compound 7,

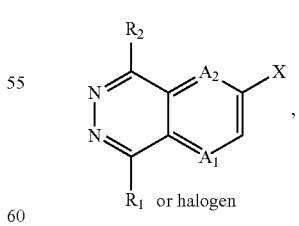

wherein A$^1$, A$^2$, R$^1$ and R$^2$ are as defined herein in Formulas I or II and X is a halogen, with a boronic acid having a general formula (RO)$_2$B-optionally substituted aryl/heteroaryl, B ring as defined herein, and R is H or an optionally substituted ethyl group forming a cyclic borolane reagent, to make a compound of Formula I or II. In another embodiment, a compound of Formula II can be made by a method or comprising the step of reacting a compound 8,

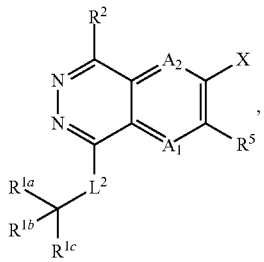

wherein $A^1$, $A^2$, $L^2$, $R^{1a}$, $R^{1b}$, $R^{1c}$, $R^2$ and $R^5$ are as defined herein in Formula II and X is a halogen, with a boronic acid having a general formula

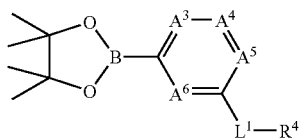

wherein $A^3$, $A^4$, $A^5$, $A^6$, $L^1$, and $R^4$ are as defined herein bin Formula II, to make a compound of Formula II.

Compounds of the present invention can possess, in general, one or more asymmetric carbon atoms and are thus capable of existing in the form of optical isomers including, without limitation, racemates and racemic mixtures, scalemic mixtures, single enantiomers, individual diastereomers and diastereomeric mixtures. All such isomeric forms of these compounds are expressly included in the present invention.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

These detailed descriptions fall within the scope, and serve to exemplify, the above-described General Synthetic Procedures which form part of the invention. These detailed descriptions are presented for illustrative purposes only and are not intended as a restriction on the scope of the invention.

Although the pharmacological properties of the compounds of the invention (Formulas I-IV) vary with structural change, in general, activity possessed by compounds of Formulas I, II, III and IV may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to inhibit the activity of various kinase enzymes, including, without limitation, p38 receptor kinase at doses less than 25 µM.

Biological Evaluation

The following assays were used to characterize the ability of compounds of the invention to inhibit the production of TNF-α and interleukin cytokines, including IL-1, IL-1-β, Il-6 and IL-8. The second assay can be used to measure the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a cyclooxygenase enzyme (COX-1 and COX-2) inhibition activity in vitro assay, can be used to characterize the ability of compounds of the invention to inhibit COX-1 and/or COX-2.

Lipopolysaccharide-Activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2 \times 10^6$/mL in DMEM supplemented to contain 2% FCS, 10 mM, 0.3 mg/mL glutamate, 100 U/mL penicillin G and 100 mg/mL streptomycin sulfate (complete media). Cells were plated into Falcon flat bottom, 96 well culture plates (200 μL/well) and cultured overnight at 37° C. and 6% $CO_2$. Non-adherent cells were removed by washing with 200 μl/well of fresh medium. Wells containing adherent cells (~70% monocytes) were replenished with 100 μL of fresh medium.

Preparation of Test Compound Stock Solutions

Test compounds were dissolved in DMZ. Compound stock solutions were prepared to an initial concentration of 10-50 μM. Stocks were diluted initially to 20-200 μM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 μL complete medium. Monocytes were cultured with test compounds for 60 min at which time 25 μL of complete medium containing 30 ng/mL lipopolysaccharide from E. coli K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 μL/well of 3 μg/mL murine anti-human TNF-α MAb (R&D Systems #MAB210). Wells were then blocked for 1 h at room temperature with 200 μL/well of $CaCl_2$-free ELISA buffer supplemented to contain 20 mg/mL BSA (standard ELISA buffer: 20 mM, 150 mM NaCl, 2 mM $CaCl_2$, 0.15 mM thimerosal, pH 7.4). Plates were washed and replenished with 100 μL of test supernatants (diluted 1:3) or standards. Standards consisted of eleven 1.5-fold serial dilutions from a stock of 1 ng/mL recombinant human TNF (R&D Systems). Plates were incubated at room temperature for 1 h on orbital shaker (300 rpm), washed and replenished with 100 μL/well of 0.5 μg/mL goat anti-human TNF-α (R&D systems #AB-210-NA) biotinylated at a 4:1 ratio. Plates were incubated for 40 min, washed and replenished with 100 μL/well of alkaline phosphatase-conjugated streptavidin (Jackson ImmunoResearch #016-050-084) at 0.02 μg/mL. Plates were incubated 30 min, washed and replenished with 200 μL/well of 1 mg/mL of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production. Of the compounds tested, Examples 2-5, 8-10, 12-13, 15-43, 45-54, 56-59, 61-73, 75-78, 83-88, 90, 94-95, 223-227b, 229-230, 233-236, 238-239, 241-244 and 248-259 exhibited activities in the whole blood monocyte assay (LPS induced TNF release) with $IC_{50}$ values of 1 μM or less. Examples 2-5, 8-10, 12-13, 15-43, 45-54, 56-59, 61-72, 75-78, 83-88, 90, 94-95, 223-227b, 229-230, 233-236, 238, 241-244 and 248-259 exhibited activities in the whole blood monocyte assay (LPS induced TNF release) with $IC_{50}$ values of 250 nM or less. Examples 2-5, 8-10, 12-13, 15-21, 23-24, 27-32, 34-39, 41, 43, 45-47, 52, 54, 56-59, 61-72, 75-78, 83-88, 90, 94-95, 223-227b, 229-230, 233-236, 241-244 and 248-259 exhibited activities in the whole blood monocyte assay (LPS induced TNF release) with $IC_{50}$ values of 100 nM or less. Examples 3, 5, 13, 15, 16, 29, 31-32, 35, 37, 39, 46-47, 51, 52, 54, 56-57, 61-63, 66, 69-70, 72, 75-76, 86-88, 94-95, 223, 225-227a, 227b, 229-230, 234-236, 241-244, 248-253 and 255-256 exhibited activities in the whole blood monocyte assay (LPS induced TNF release) with $IC_{50}$ values of 10 nM or less.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. The compounds of the invention are useful in the methods of treating disease states in which TNF-α, IL-1β, IL-6, and IL-8 play a role to the full extent of the definition of TNF-α-mediated diseases described herein.

Lipopolysaccharide-Activated THP1 Cell TNF Production Assay

THP1 cells are resuspended in fresh THP1 media (RPMI 1640, 10% heat-inactivated FBS, 1XPGS, 1XNEAA, plus 30 μM βME) at a concentration of 1E6/mL. One hundred microliters of cells per well are plated in a polystyrene 96-well tissue culture. One microgram per mL of bacterial LPS is prepared in THP1 media and is transferred to the wells. Test compounds are dissolved in 100% DMSO and are serially diluted 3-fold in a polypropylene 96-well microtiter plate (drug plate). HI control and LO control wells contain only DMSO. One microliter of test compound from the drug plate followed by 10 μL of LPS are transferred to the cell plate. The treated cells are induced to synthesize and secrete TNF-α at 37° C. for 3 h. Forty microliters of conditioned media are transferred to a 96-well polypropylene plate containing 110 μL of ECL buffer (50 mM Tris-HCl pH 8.0, 100 mM NaCl, 0.05% Tween 20, 0.05% $NaN_3$ and 1% FBS) supplemented with 0.44 nM MAB610 monoclonal Ab (R&D Systems), 0.34 nM ruthenylated AF210NA polyclonal Ab (R&D Systems) and 44 μg/mL sheep anti-mouse M280 Dynabeads (Dynal). After a 2 h incubation at room temperature with shaking, the reaction is read on the ECL M8 Instrument (IGEN Inc.). A low voltage is applied to the ruthenylated TNF-α immune complexes, which in the presence of TPA (the active component in Origlo), results in a cyclical redox reaction generating light at 620 nM. The amount of secreted TNF-α in the presence of compound compared with that in the presence of DMSO vehicle alone (HI control) is calculated using the formula: % control (POC)=(cpd−average LO)/(average HI−average LO)*100. Data (consisting of POC and inhibitor concentration in μM) is fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

Of the compounds tested, Examples 2-6, 8-10, 12-49, 51-78, 81-95, 223-227b, 229-236, 243-244 and 248-259 exhibited activities in the lipopolysaccharide-activated THP1 Cell TNF production assay with $IC_{50}$ values of 1 μM or less. Of the compounds tested, Examples 2-6, 8-10, 12-49, 51-54, 56-78, 81-95, 223-227b, 229-236, 243-244 and 248-259 exhibited activities in the lipopolysaccharide-activated THP1

Cell TNF production assay with $IC_{50}$ values of 250 nM or less. Of the compounds tested, Examples 2-6, 8-10, 12-47, 49, 51-54, 56-78, 81-95, 223-227b, 229-236, 243-244 and 248-259 exhibited activities in the lipopolysaccharide-activated THP1 Cell TNF production assay with $IC_{50}$ values of 100 nM or less. Of the compounds tested, Examples 2-6, 8-10, 12-43, 45-47, 51-54, 56-78, 81-95, 223-227b, 229-230, 232-236, 243-244 and 248-259 exhibited activities in the lipopolysaccharide-activated THP1 Cell TNF production assay with $IC_{50}$ values of 25 μM or less. Of the compounds tested, Examples 2, 3, 5, 8-10, 12-21, 23, 25, 27-40, 42-43, 45-47, 51-54, 56-78, 81-95, 223-227b, 229-230, 232-236, 243-244 and 248-259 exhibited activities in the lipopolysaccharide-activated THP1 Cell TNF production assay with $IC_{50}$ values of 10 nM or less.

Inhibition of LPS-Induced TNF-α Production in Mice

Male DBA/1LACJ mice are dosed with vehicle or test compounds in a vehicle (the vehicle consisting of 0.5% tragacanth in 0.03 N HCl) 30 min prior to lipopolysaccharide (2 mg/Kg, I.V.) injection. Ninety minutes after LPS injection, blood is collected and the serum is analyzed by ELISA for TNF-α levels.

Compounds of the invention may be shown to have anti-inflammatory properties in animal models of inflammation, including carageenan paw edema, collagen induced arthritis and adjuvant arthritis, such as the carageenan paw edema model (C. A. Winter et al., Proc. Soc. Exp. Biol. Med., 111: 544 (1962); K. F. Swingle, in R. A. Scherrer and M. W. Whitehouse, Eds., Anti-inflammatory Agents, Chemistry and Pharmacology, 13(II):33, Academic, New York (1974) and collagen induced arthritis (D. E. Trentham et al., J. Exp. Med., 146:857 (1977); J. S. Courtenay, Nature (New Biol.), 283:666 (1980)).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/mL ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per mL DMSO and store aliquots at −20° C.; (d) 250 μM human glucagon (Peninsula): solubilize 0.5 mg vial in 575 μl 0.1N acetic acid (1 μL yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μL 10% BSA (heat-inactivated) and 990 μL Assay Buffer; (g) $^{125}$I-Glucagon (NEN, receptor-grade, 2200 Ci/mmol): dilute to 50,000 cpm/25 μL in assay buffer with BSA (about 50 pM final concentration in assay).

Harvesting of CHO/hGLUR Cells for Assay

1. Remove media from confluent flask then rinse once each with PBS (Ca, Mg- free) and Enzyme-free Dissociation Fluid (Specialty Media, Inc.).

2. Add 10 mL Enzyme-free Dissoc. Fluid and hold for about 4 min at 37° C.

3. Gently tap cells free, triturate, take aliquot for counting and centrifuge remainder for 5 min at 1000 rpm.

4. Resuspend pellet in Assay Buffer at 75000 cells per 100 μL.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of $I^{125}$-glucagon binding in the presence of compounds of Formula I. The reagents are combined as follows:

|  | Compound/Vehicle | 250 μM Glucagon | $^{125}$I-Glucagon | CHO/hGLUR Cells |
|---|---|---|---|---|
| Total Binding + | —/5 μl | — | 25 μL | 100 μL |
| Compound | 5 μl/— | — | 25 μL | 100 μL |
| Nonspecific Binding | —/5 μl | 1 μl | 25 μL | 100 μL |

The mixture is incubated for 60 min at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1b/mL, and the cells incubated for 18-22 h. Following replacement of media with 190 mL MEM, 10 mL of test compound diluted in HBS is added to achieve the desired concentration and the cells incubated for 4 h. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen

404110). A standard curve of PGE$_2$ is used for calibration, and commercially available COX-1 and COX-2 inhibitors are included as standard controls. Various compounds of the invention may be shown to inhibit the COX-1 and/or COX-2 activity.

Compounds of the present invention have unexpected and surprising pharmacokinetic (pK) and pharmacodynamic (PD) properties. For example, advantageous pK properties include improved half lives, reduced clearance, and improved oral or interperatoneal (IP) bioavailability of the active compound in various species, including rodent, dog and primates. Such properties are important considerations for clinical development and commercial treatment of illnesses and conditions related to and/or resulting from abnormal activity of the p38 enzyme.

Indications

The compounds of the invention are useful for, but not limited to, the prevention or treatment of inflammation, pro-inflammatory cytokine levels including, without limitation, TNF, IL-1, IL-2, IL-6 and/or IL-8, and diseases associated therewith. The compounds of the invention have kinase modulatory activity in general, and p38 kinase modulatory activity in particular. In one embodiment of the invention, there is provided a method of treating a disorder related to the activity of p38 enzyme in a subject, the method comprising administering to the subject an effective dosage amount of a compound of a compound of Formulas I, II, III or IV.

Accordingly, the compounds of the invention would be useful in therapy as anti-inflammatory agents in treating inflammation, or to treat, reduce or minimize deleterious effects of p38. Based on the ability to modulate pro-inflammatory cytokine production, the compounds of the invention are also useful in treatment and therapy of cytokine-mediated diseases. Particularly, these compounds can be used for the treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection, or any combination thereof, in a subject.

The compounds can also be used to treat other forms of inflammation, such as synovial inflammation. For example, synovitis, including any of the particular forms of synovitis, in particular bursal synovitis and purulent synovitis, can be treated as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further applicable to the treatment of inflammation, e.g. inflammatory disease or condition, of connective tissues including dermatomyositis and myositis.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration.

The compounds of the invention are also useful in the treatment of diabetic conditions such as diabetic retinopathy and microangiopathy.

The compounds of the present invention are also useful for treating ankylosing spondylitis, inflammatory bowel disease, inflammatory pain, ulcerative colitis, asthma, chronic obstructive pulmonary disease, myelodysplastic syndrome, endotoxic shock, chronic hepatitis C or a combination thereof.

The present invention also provides methods for the treatment of protein tyrosine kinase-associated disorders, comprising the step of administering to a subject in need thereof at least one compound of the Formula I, II, III or of Formula IV in an amount effective therefore. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides for a method for treating the aforementioned disorders such as atopic dermatitis by administration of a therapeutically effective amount of a compound of the present invention, which is an inhibitor of protein tyrosine kinase, to a patient, whether or not in need of such treatment.

In yet another embodiment, the compounds are useful for decreasing the level of, or lowering plasma concentrations of, one or more of TNF-α, IL-1β, IL-6 and IL-8 in a subject, generally a mammal and typically a human.

In yet another embodiment, the compounds are useful for treating a pain disorder in a subject, which is typically a human by administering to the subject an effective dosage amount of a compound according to formulas I-IV.

In yet another embodiment, the compounds are useful for treating diabetes in a subject, which is typically a human, by administering to the subject an effective dosage amount of a compound according to formulas I-IV, to produce a glucagon antagonist effect.

In yet another embodiment, the compounds are useful for decreasing prostaglandin production in a subject, which is typically a human, by administering to the subject an effective dosage amount of a compound according to formulas I-IV.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in heed of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating TNF-α, IL-1, IL-6, and IL-8 mediated diseases, cancer, and/or hyperglycemia with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg, and even more advantageously between about 0.25 and about 1 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I-IV with a pharmaceutically acceptable carrier to manufacture the medicament.

In yet another embodiment, there is provided a method of manufacturing a medicament for the treatment of inflammation, the method comprising combining an amount of a compound according to Formulas I-IV with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of TNF-α, IL-1, IL-6, and IL-8 mediated diseases, cancer, and/or hyperglycemia.

If formulated as a fixed dose, such combination products employ the compounds of this invention within the accepted dosage ranges. Compounds of Formulas I-IV may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The compounds of the invention may also be used in co-therapies with anti-neoplastic agents such as other kinase inhibitors, including CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

What is claimed is:

1. A compound, or a stereoisomer or pharmaceutically acceptable salt thereof, selected from:
4-methyl-N-(1-methyl-1H-pyrazol-5-yl)-3-(1-((2,2,2-trifluoro-1-methylethyl)oxy)-6-phthalazinyl)benzamide;
4-methyl-N-(1-methyl-1H-pyrazol-5-yl)-3-(1-(((1S)-2,2,2-trifluoro-1-methylethyl)oxy)-6-phthalazinyl)benzamide;
4-methyl-N-(1-methyl-1H-pyrazol-5-yl)-3-(1-(((1R)-2,2,2-trifluoro-1-methylethyl)oxy)-6-phthalazinyl)benzamide;
4-methyl-N-(1-methyl-1H-pyrazol-3-yl)-3-(1-(((1R)-2,2,2-trifluoro-1-methylethyl)oxy)-6-phthalazinyl)benzamide;
4-methyl-N-(1-methyl-1H-pyrazol-3-yl)-3-(1-(((1S)-2,2,2-trifluoro-1-methylethyl)oxy)-6-phthalazinyl)benzamide;
N-cyclopropyl-4-methyl-3-(1-(2,2,2-trifluoro-1-methylethyl)oxy)-6-phthalazinyl)benzamide;
N-cyclopropyl-4-methyl-3-(1-(((1S)-2,2,2-trifluoro-1-methylethyl)oxy)-6-phthalazinyl)benzamide;
N-cyclopropyl-4-methyl-3-(1-(((1R)-2,2,2-trifluoro-1-methylethyl)oxy)-6-phthalazinyl)benzamide;
4-methyl-N-(4-methyl-1,3-oxazol-2-yl)-3-(1-((2,2,2-trifluoro-1-methylethyl)oxy)-6-phthalazinyl)benzamide;
4-methyl-N-(1-methylethyl)-3-(1-(((1S)-2,2,2-trifluoro-1-methylethyl)oxy)-6-phthalazinyl)benzamide;
4-methyl-N-(1-methylethyl)-3-(1-(((1R)-2,2,2-trifluoro-1-methylethyl)oxy)-6-phthalazinyl)benzamide;
3-(1-((2-fluoro-1-(fluoromethyl)ethyl)oxy)-6-phthalazinyl)-4-methyl-N-(1-methyl-1H-pyrazol-5-yl)benzamide;
N-cyclopropyl-3-(1-((2-fluoro-1-(fluoromethyl)ethyl)oxy)-6-phthalazinyl)-4-methylbenzamide;
4-methyl-3-(1-(1-methylethyl)-6-phthalazinyl)-N-(2,2,2-trifluoroethyl)benzamide;
4-methyl-N-(1-methylcyclopropyl)-3-(1-(((1S)-2,2,2-trifluoro-1-methylethyl)oxy)-6-phthalazinyl)benzamide;
4-methyl-N-(1-methylcyclopropyl)-3-(1-(((1R)-2,2,2-trifluoro-1-methylethyl)oxy)-6-phthalazinyl)benzamide;
4-methyl-N-1,3,4-thiadiazol-2-yl-3-(1-(((1R)-2,2,2-trifluoro-1-methylethyl)oxy)-6-phthalazinyl)benzamide;
4-methyl-N-1,3,4-thiadiazol-2-yl-3-(1-(((1S)-2,2,2-trifluoro-1-methylethyl)oxy)-6-phthalazinyl)benzamide;
N-cyclopropyl-4-methyl-3-(1-((1S)-2,2,2-trifluoro-1-methylethyl)-6-phthalazinyl)benzamide;
N-cyclopropyl-4-methyl-3-(1-((1S)-2,2,2-trifluoro-1-methylethyl)-6-phthalazinyl)benzamide;
4-methyl-N-(1-methyl-1H-pyrazol-5-yl)-3-(1-((1R)-2,2,2-trifluoro-1-methylethyl)-6-phthalazinyl)benzamide;
4-methyl-N-(1-methyl-1H-pyrazol-5-yl)-3-(1-((1S)-2,2,2-trifluoro-1-methylethyl)-6-phthalazinyl)benzamide;
4-methyl-N-(1-methyl-1H-pyrazol-5-yl)-3-(1-(2,2,2-trifluoro-1-hydroxy-1-methylethyl)-6-phthalazinyl)benzamide;
4-methyl-N-(1-methyl-1H-pyrazol-5-yl)-3-(1-(R)-2,2,2-trifluoro-1-methylethyl)-6-phthalazinyl)benzamide;
4-methyl-N-(1-methyl-1H-pyrazol-5-yl)-3-(1-(S)-2,2,2-trifluoro-1-methylethyl)-6-phthalazinyl)benzamide;
N-cyclopropyl-4-methyl-3-(1-(2,2,2-trifluoro-1-hydroxy-1-methylethyl)-6-phthalazinyl)benzamide;
3-(1-(1-fluoro-1-methylethyl)-6-phthalazinyl)-4-methyl-N-(1-methyl-1H-pyrazol-5-yl)benzamide;
4-methyl-N-(1-methyl-1H-pyrazol-5-yl)-3-(1-((1R)-2,2,2-trifluoro-1-hydroxy-1-methylethyl)-6-phthalazinyl)benzamide;
N-ethyl-4-methyl-3-(1-(((1S)-2,2,2-trifluoro-1-methylethyl)oxy)-6-phthalazinyl)benzamide; and
N,4-dimethyl-3-(1-(((1S)-2,2,2-trifluoro-1-methylethyl)oxy)-6-phthalazinyl)benzamide.

2. A pharmaceutical composition comprising a pharmaceutically acceptable excipient and a compound, or a stereoisomer or pharmaceutically acceptable salt thereof, according to claim 1.

3. A compound, or a stereoisomer or pharmaceutically acceptable salt thereof, having a Formula IV

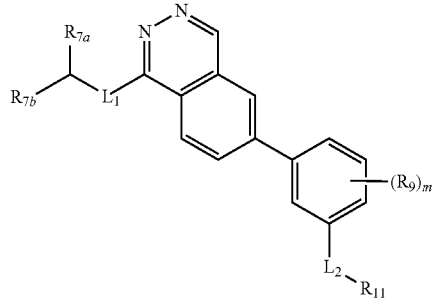

wherein
$L^1$ is —O— or a single bond;
$L^2$ is —C(O)NH—, —NHC(O)—, —NHC(O)NH—, —S(O)$_2$NH—, —NHS(O)$_2$NH— or —NHS(O)$_2$—;
$R^{7a}$ is H or $C_{1-10}$-alkyl;
$R^{7b}$ is $C_{1-10}$-alkyl or $CF_3$, provided the $C_{1-10}$-alkyl is substituted with at least one fluorine;
each $R^9$, independently, is halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamino, isopropylamino, dipropylamino, diisopropylamino methylamine, or acetyl;
$R^{11}$ is a phenyl, naphthyl, pyridyl, pyrimidyl, quinolinyl, isoquinolinyl, quinazolinyl, thienyl, furyl, pyrrolyl, pyrazolyl, imidazolyl, triazolyl, thiazolyl, thiadiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-5 substituents of halo, haloalkyl, CN, OH, NO$_2$, NH$_2$, OH, oxo, methyl, methoxyl, ethyl, ethoxyl, propyl, propoxyl, isopropyl, cyclopropyl, butyl, isobutyl, tert-butyl, pentyl, hexyl, methylamino, dimethylamino, ethylamino, diethylamino, isopropylamino, acetyl, benzyl, or phenyl; and
m is 0, 1, 2 or 3.

4. A compound, or a stereoisomer or pharmaceutically acceptable salt thereof, selected from:

N-3-isoxazolyl-4-methyl-3-(1-((1-methylethyl)oxy)-6-phthalazinyl)benzamide;
4-methyl-3-(1-((3S)-3-methyl-4-morpholinyl)-6-phthalazinyl)-N-(1-methyl-1H-pyrazol-5-yl)benzamide;
N-(1-ethyl-1H-pyrazol-5-yl)-4-methyl-3-(1-((3S)-3-methyl-4-morpholinyl)-6-phthalazinyl)benzamide;
4-methyl-3-(1-((1-methylethyl)amino)-6-phthalazinyl)-N-(1-methyl-1H-pyrazol-5-yl)benzamide;
N-(1-ethyl-1H-pyrazol-5-yl)-4-methyl-3-(1-((1-methylethyl)amino)-6-phthalazinyl)benzamide;
N-(1-ethyl-1H-pyrazol-5-yl)-4-methyl-3-(1-((1-methylethyl)oxy)-6-phthalazinyl)benzamide;
4-methyl-3-(1-((1-methylethyl)oxy)-6-phthalazinyl)-N-(1-methyl-1H-pyrazol-5-yl)benzamide;
N-cyclopropyl-3-(1-(ethyloxy)-6-phthalazinyl)-4-methylbenzamide;
4-methyl-N-(1-methyl-1H-pyrazol-5-yl)-3-(1-((2,2,2-trifluoro-1-methylethyl)oxy)-6-phthalazinyl)benzamide;
4-chloro-3-(1-((1-methylethyl)oxy)-6-phthalazinyl)benzamide;
4-chloro-N-(1-methylethyl)-3-(1-((1-methylethyl)oxy)-6-phthalazinyl)benzamide;
4-methyl-N-(1-methylethyl)-3-(1-((2,2,2-trifluoro-1-methylethyl)oxy)-6-phthalazinyl)benzamide;
4-methyl-N-(1-methylethyl)-3-(1-(2-methylpropyl)-6-phthalazinyl)benzamide;
4-methyl-N-(1-methyl-1H-pyrazol-5-yl)-3-(1-((2,2,2-trifluoroethyl)oxy)-6-phthalazinyl)benzamide; 4-methyl-N-(1-methyl-1H-pyrazol-5-yl)-3-(1-(((1S)-2,2,2-trifluoro-1-methylethyl)oxy)-6-phthalazinyl)benzamide;
4-methyl-N-(1-methyl-1H-pyrazol-5-yl)-3-(1-(((1R)-2,2,2-trifluoro-1-methylethyl)oxy)-6-phthalazinyl)benzamide;
N-cyclopropyl-4-methyl-3-(1-(2,2,2-trifluoro-1-methylethyl)oxy)-6-phthalazinyl)benzamide;
3-(1-((2R)-2-(1,1-dimethylethyl)-1-pyrrolidinyl)-6-phthalazinyl)-4-methyl-N-(1-methylethyl)benzamide;
3-(1-((2S)-2-(1,1-dimethylethyl)-1-pyrrolidinyl)-6-phthalazinyl)-4-methyl-N-(1-methylethyl)benzamide;
3-(1-((2R)-2-(1,1-dimethylethyl)-1-pyrrolidinyl)-6-phthalazinyl)-4-methylbenzamide;
3-(1-((2S)-2-(1,1-dimethylethyl)-1-pyrrolidinyl)-6-phthalazinyl)-4-methylbenzamide;
4-methyl-N-(1-methylethyl)-3-(1-((2S)-2-methyl-1-pyrrolidinyl)-6-phthalazinyl)benzamide;
4-methyl-N-(1-methylethyl)-3-(1-((2R)-2-methyl-1-pyrrolidinyl)-6-phthalazinyl)benzamide;
4-methyl-N-(4-methyl-1,3-oxazol-2-yl)-3-(1-((2,2,2-trifluoro-1-methylethyl)oxy)-6-phthalazinyl)benzamide;
4-methyl-N-(1-methylethyl)-3-(1-(((1S)-2,2,2-trifluoro-1-methylethyl)oxy)-6-phthalazinyl)benzamide;
4-methyl-N-(1-methylethyl)-3-(1-(((1R)-2,2,2-trifluoro-1-methylethyl)oxy)-6-phthalazinyl)benzamide;
4-methyl-3-(1-(((1S)-2,2,2-trifluoro-1-methylethyl)oxy)-6-phthalazinyl)benzamide;
4-methyl-3-(1-(((1R)-2,2,2-trifluoro-1-methylethyl)oxy)-6-phthalazinyl)benzamide;
N-(1,1-dimethylethyl)-4-methyl-3-(1-(((1S)-2,2,2-trifluoro-1-methylethyl)oxy)-6-phthalazinyl)benzamide;
4-methyl-N-(1-methyl-1H-pyrazol-3-yl)-3-(1-(((1R)-2,2,2-trifluoro-1-methylethyl)oxy)-6-phthalazinyl)benzamide;
4-methyl-3-(1-((2S)-2-(trifluoromethyl)-1-pyrrolidinyl)-6-phthalazinyl)benzamide;
3-(1-((2-fluoro-1-(fluoromethyl)ethyl)oxy)-6-phthalazinyl)-4-methyl-N-(1-methyl-1H-pyrazol-5-yl)benzamide;
N-cyclopropyl-3-(1-((2-fluoro-1-(fluoromethyl)ethyl)oxy)-6-phthalazinyl)-4-methylbenzamide;
3-(1-hydroxy-6-phthalazinyl)-4-methyl-N-(1-methyl-1H-pyrazol-5-yl)benzamide;
4-methyl-3-(1-(1-methylpropyl)-6-phthalazinyl)benzamide; 4-methyl-3-(1-(1-methylethyl)-6-phthalazinyl)-N-(2,2,2-trifluoroethyl)benzamide;
N-cyclopropyl-4-methyl-3-(1-(((1S)-2,2,2-trifluoro-1-methylethyl)oxy)-6-phthalazinyl)benzamide;
N-cyclopropyl-4-methyl-3-(1-(((1R)-2,2,2-trifluoro-1-methylethyl)oxy)-6-phthalazinyl)benzamide;
3-(1-chloro-6-phthalazinyl)-4-methyl-N-(1-methyl-1H-pyrazol-5-yl)benzamide;
4-methyl-3-(1-(2-methylphenyl)-6-phthalazinyl)-N-(1-methyl-1H-pyrazol-5-yl)benzamide;
3-(1-(4-fluorophenyl)-6-phthalazinyl)-4-methyl-N-(1-methyl-1H-pyrazol-5-yl)benzamide
4-methyl-3-(1-(1-methylethyl)-6-phthalazinyl)benzamide;
4-methyl-N-(1-methylcyclopropyl)-3-(1-(((1S)-2,2,2-trifluoro-1-methylethyl)oxy)-6-phthalazinyl)benzamide;
3-(1-(1,1-dimethylethyl)-6-phthalazinyl)-4-methyl-N-(1-methylethyl)benzamide;
3-(1-(4-fluoro-2-methylphenyl)-6-phthalazinyl)-4-methyl-N-(1-methyl-1H-pyrazol-3-yl)benzamide;
4-methyl-3-(1-(2-methylphenyl)-6-phthalazinyl)-N-(1-methyl-1H-pyrazol-3-yl)benzamide;
4-methyl-N-(1-methylcyclopropyl)-3-(1-((2S)-2-methyl-1-pyrrolidinyl)-6-phthalazinyl)benzamide;
4-methyl-N-(1-methylcyclopropyl)-3-(1-(((1S)-2,2,2-trifluoro-1-methylethyl)oxy)-6-phthalazinyl)benzamide;
4-methyl-N-(1-methylcyclopropyl)-3-(1-(((1R)-2,2,2-trifluoro-1-methylethyl)oxy)-6-phthalazinyl)benzamide;
4-methyl-N-(1-methylcyclopropyl)-3-(1-(1-methylethyl)-6-phthalazinyl)benzamide;
N-cyclopropyl-3-(1-(1,1-dimethylethyl)-6-phthalazinyl)-4-methylbenzamide;
4-methyl-N-(1-methyl-1H-pyrazol-3-yl)-3-(1-(((1R)-2,2,2-trifluoro-1-methylethyl)oxy)-6-phthalazinyl)benzamide;
4-methyl-N-(1-methyl-1H-pyrazol-3-yl)-3-(1-(((1S)-2,2,2-trifluoro-1-methylethyl)oxy)-6-phthalazinyl)benzamide;
4-methyl-N-(2,2,2-trifluoroethyl)-3-(1-(((1R)-2,2,2-trifluoro-1-methylethyl)oxy)-6-phthalazinyl)benzamide;
4-methyl-N-(2,2,2-trifluoroethyl)-3-(1-(((1S)-2,2,2-trifluoro-1-methylethyl)oxy)-6-phthalazinyl)benzamide;
N-cyclopropyl-3-(1-(2,2-dimethylpropyl)-6-phthalazinyl)-4-methylbenzamide;
3-(1-(2,2-dimethylpropyl)-6-phthalazinyl)-4-methyl-N-(1-methylcyclopropyl)benzamide; 3-(1-(2,2-dimethylpropyl)-6-phthalazinyl)-4-methyl-N-(2,2,2-trifluoroethyl)benzamide;
4-methyl-N-(2,2,2-trifluoroethyl)-3-(1-(((1R)-2,2,2-trifluoro-1-methylethyl)oxy)-6-phthalazinyl)benzamide;
4-methyl-N-(2,2,2-trifluoroethyl)-3-(1-(((1S)-2,2,2-trifluoro-1-methylethyl)oxy)-6-phthalazinyl)benzamide;
3-(1-(1,1-dimethylethyl)-6-phthalazinyl)-4-methyl-N-(1-methyl-1H-pyrazol-5-yl)benzamide;
3-(1-(1,1-dimethylethyl)-6-phthalazinyl)-4-methyl-N-(2,2,2-trifluoroethyl)benzamide;
4-methyl-N-1,3,4-thiadiazol-2-yl-3-(1-(((1R)-2,2,2-trifluoro-1-methylethyl)oxy)-6-phthalazinyl)benzamide;

4-methyl-N-1,3,4-thiadiazol-2-yl-3-(1-(((1S)-2,2,2-trifluoro-1-methylethyl)oxy)-6-phthalazinyl)benzamide;
4-methyl-N-1,3-thiazol-2-yl-3-(1-(((1S)-2,2,2-trifluoro-1-methylethyl)oxy)-6-phthalazinyl)benzamide;
4-methyl-N-1,3-thiazol-2-yl-3-(1-(((1R)-2,2,2-trifluoro-1-methylethyl)oxy)-6-phthalazinyl)benzamide;
4-methyl-3-(1-(2-methyl-4-(methylsulfonyl)phenyl)-6-phthalazinyl)-N-(1-methyl-1H-pyrazol-5-yl)benzamide;
3-(1-(1,1-dimethylethyl)-6-phthalazinyl)-4-methyl-N-(1-methylcyclopropyl)benzamide;
N-cyclopropyl-4-methyl-3-(1-((1S)-2,2,2-trifluoro-1-methylethyl)-6-phthalazinyl)benzamide;
N-cyclopropyl-4-methyl-3-(1-((1S)-2,2,2-trifluoro-1-methylethyl)-6-phthalazinyl)benzamide;
N-cyclopropyl-4-methyl-3-(1-(1-(trifluoromethyl)ethenyl)-6-phthalazinyl)benzamide;
4-methyl-N-(1-methyl-1H-pyrazol-5-yl)-3-(1-(1-(trifluoromethyl)ethenyl)-6-phthalazinyl)benzamide;
4-methyl-N-(1-methyl-1H-pyrazol-5-yl)-3-(1-((1R)-2,2,2-trifluoro-1-methylethyl)-6-phthalazinyl)benzamide;
4-methyl-N-(1-methyl-1H-pyrazol-5-yl)-3-(1-((1S)-2,2,2-trifluoro-1-methylethyl)-6-phthalazinyl)benzamide;
4-methyl-N-(1-methyl-1H-pyrazol-5-yl)-3-(1-((1R)-2,2,2-trifluoro-1-methylethyl)-6-phthalazinyl)benzamide; and
and 4-methyl-N-(1-methyl-1H-pyrazol-5-yl)-3-(1-(((1S)-2,2,2-trifluoro-1-methylethyl)-6-phthalazinyl)benzamide.

5. A pharmaceutically acceptable salt form of the compound of claim 1.

6. A pharmaceutically acceptable salt form of the compound of claim 4.

7. A pharmaceutical composition comprising a pharmaceutically acceptable excipient and an effective dosage amount of a compound according to claim 4.

8. The compound of claim 4, or a stereoisomer or pharmaceutically acceptable salt thereof, that is N-cyclopropyl-4-methyl-3-(1-((2,2,2-trifluoro-1-methylethyl)oxy)-6-phthalazinyl)benzamide and has a chemical structure of

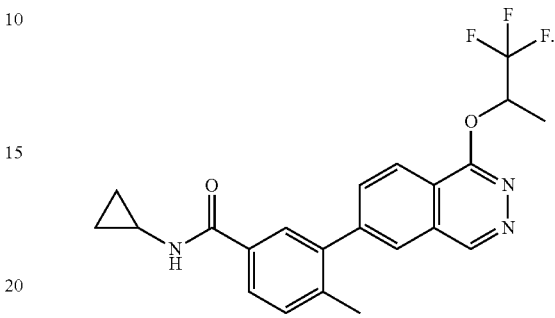

9. The compound of claim 8, or a stereoisomer or pharmaceutically acceptable salt thereof, that is N-cyclopropyl-4-methyl-3-(1-(((1S)-2,2,2-trifluoro-1-methylethyl)oxy)-6-phthalazinyl)benzamide.

10. The compound of claim 8, or a stereoisomer or pharmaceutically acceptable salt thereof, that is N-cyclopropyl-4-methyl-3-(1-(((1R)-2,2,2-trifluoro-1-methylethyl)oxy)-6-phthalazinyl)benzamide.

* * * * *